US008101197B2

(12) United States Patent
Buiser et al.

(10) Patent No.: US 8,101,197 B2
(45) Date of Patent: Jan. 24, 2012

(54) FORMING COILS

(75) Inventors: Marcia S. Buiser, Watertown, MA (US);
Elaine Lee, Sunnyvale, CA (US)

(73) Assignees: Stryker Corporation, Kalamazoo, MI
(US); Stryker NV Operations Limited,
Dublin (IE)

(*) Notice: Subject to any disclaimer, the term of this patent is extended or adjusted under 35 U.S.C. 154(b) by 590 days.

(21) Appl. No.: 11/311,617

(22) Filed: Dec. 19, 2005

(65) Prior Publication Data
US 2007/0141099 A1 Jun. 21, 2007

(51) Int. Cl.
*A61F 2/02* (2006.01)
*B05D 3/00* (2006.01)
(52) U.S. Cl. ........................... 424/422; 427/426
(58) Field of Classification Search .................. None
See application file for complete search history.

(56) References Cited

U.S. PATENT DOCUMENTS

| | | |
|---|---|---|
| 2,609,347 A | 9/1952 | Wilson |
| 3,663,470 A | 5/1972 | Nishimura et al. |
| 3,737,398 A | 6/1973 | Yamaguchi |
| 3,921,632 A | 11/1975 | Bardani |
| 3,957,933 A | 5/1976 | Egli et al. |
| 4,025,686 A | 5/1977 | Zion |
| 4,034,759 A | 7/1977 | Haerr |
| 4,055,377 A | 10/1977 | Erickson et al. |
| 4,076,640 A | 2/1978 | Forgensi et al. |
| 4,094,848 A | 6/1978 | Naito |
| 4,096,230 A | 6/1978 | Haerr |
| 4,098,728 A | 7/1978 | Rosenblatt |
| 4,110,529 A | 8/1978 | Stoy |
| 4,159,719 A | 7/1979 | Haerr |
| 4,191,672 A | 3/1980 | Salome et al. |
| 4,198,318 A | 4/1980 | Stowell et al. |
| 4,243,794 A | 1/1981 | White et al. |
| 4,246,208 A | 1/1981 | Dundas |
| 4,266,030 A | 5/1981 | Tschang et al. |
| 4,268,495 A | 5/1981 | Muxfeldt et al. |
| 4,271,281 A | 6/1981 | Kelley et al. |
| 4,402,319 A | 9/1983 | Handa et al. |
| 4,413,070 A | 11/1983 | Rembaum |
| 4,427,794 A | 1/1984 | Lange et al. |
| 4,428,869 A | 1/1984 | Munteanu et al. |
| 4,429,062 A | 1/1984 | Pasztor et al. |
| 4,442,843 A | 4/1984 | Rasor et al. |
| 4,444,961 A | 4/1984 | Timm |
| 4,452,773 A | 6/1984 | Molday |
| 4,456,693 A | 6/1984 | Welsh |
| 4,459,145 A | 7/1984 | Elsholz |
| 4,472,552 A | 9/1984 | Blouin |
| 4,477,255 A | 10/1984 | Pasztor et al. |
| 4,492,720 A | 1/1985 | Mosier |
| 4,522,953 A | 6/1985 | Barby et al. |
| 4,542,178 A | 9/1985 | Zimmermann et al. |
| 4,551,132 A | 11/1985 | Pasztor et al. |
| 4,551,436 A | 11/1985 | Johnson et al. |
| 4,573,967 A | 3/1986 | Hargrove et al. |
| 4,622,362 A | 11/1986 | Rembaum |
| 4,623,706 A | 11/1986 | Timm et al. |
| 4,640,807 A | 2/1987 | Afghan et al. |
| 4,657,756 A | 4/1987 | Rasor et al. |
| 4,661,137 A | 4/1987 | Garnier et al. |
| 4,663,358 A | 5/1987 | Hyon et al. |
| 4,671,954 A | 6/1987 | Goldberg et al. |
| 4,674,480 A | 6/1987 | Lemelson |
| 4,675,113 A | 6/1987 | Graves et al. |
| 4,678,710 A | 7/1987 | Sakimoto et al. |
| 4,678,814 A | 7/1987 | Rembaum |
| 4,680,320 A | 7/1987 | Uku et al. |
| 4,681,119 A | 7/1987 | Rasor et al. |
| 4,708,718 A | 11/1987 | Daniels |
| 4,742,086 A | 5/1988 | Masamizu et al. |
| 4,743,507 A | 5/1988 | Franses et al. |
| 4,772,635 A | 9/1988 | Mitschker et al. |
| 4,782,097 A | 11/1988 | Jain et al. |
| 4,789,501 A | 12/1988 | Day et al. |
| 4,793,980 A | 12/1988 | Torobin |
| 4,795,741 A | 1/1989 | Leshchiner et al. |
| 4,801,458 A | 1/1989 | Hidaka et al. |
| 4,804,366 A | 2/1989 | Zdeb et al. |
| 4,819,637 A | 4/1989 | Dormandy, Jr. et al. |
| 4,822,535 A | 4/1989 | Ekman et al. |
| 4,833,237 A | 5/1989 | Kawamura et al. |
| 4,850,978 A | 7/1989 | Dudar et al. |
| 4,859,711 A | 8/1989 | Jain et al. |
| 4,863,972 A | 9/1989 | Itagaki et al. |

(Continued)

FOREIGN PATENT DOCUMENTS

AU    A-76186/98    10/1998

(Continued)

OTHER PUBLICATIONS

U.S. Appl. No. 11/274,538, filed Nov. 15, 2005, Tenney et al.
Krysl et al., "Embolization Agents: A Review," *Techniques in Vascular and Interventional Radiology*, 3:158-161 (2003).
Lanzino et al., "Emerging Concepts in the Treatment of Intracranial Aneurysms: Stents, Coated Coils and Liquid Embolic Agents," *Neurosurgery*, 57:449-458 (2005).
Abbara et al., "Transcervical Expulsion of a Fibroid as a Result of Uterine Artery Embolization for Leiomyomata", JVIR, vol. 10, No. 4, pp. 409-411, 1999.
Abrahams, J.M. et al., "Topic Review: Surface Modifications Enhancing Biological Activity of Guglielmi Detachable Coils in Treating Intracranial Aneurysms", Surg. Neurol. 54:34-41, 2000.
Abrahams, J.M. et al., "Delivery of Human Vascular Endothelial Growth Factor with Platinum Coils Enhances Wall Thickening and Coil Impregnation in a Rat Aneurysm Model", AJNR Am. J. Neuroradiol. 22:1410-1417, Aug. 2001.

(Continued)

*Primary Examiner* — Shanon A Foley
(74) *Attorney, Agent, or Firm* — Vista IP Law Group LLP

(57) ABSTRACT

Coils, such as embolic coils, can include a substrate; and a porous material supported by the substrate. Related methods, devices, and compositions, can include: injecting a material into a container containing the coil; and forming the material into a coating that is supported by the coil and/or contacting the coil with a composition comprising a first polymer and a gelling precursor; and forming the composition into a coating that is supported by the coil.

14 Claims, 34 Drawing Sheets

U.S. PATENT DOCUMENTS

| | | | |
|---|---|---|---|
| 4,897,255 A | 1/1990 | Fritzberg et al. |
| 4,900,303 A | 2/1990 | Lemelson |
| 4,929,400 A | 5/1990 | Rembaum et al. |
| 4,933,372 A | 6/1990 | Feibush et al. |
| 4,946,899 A | 8/1990 | Kennedy et al. |
| 4,954,399 A | 9/1990 | Tani et al. |
| 4,981,625 A | 1/1991 | Rhim et al. |
| 4,990,340 A | 2/1991 | Hidaka et al. |
| 4,994,069 A | 2/1991 | Ritchart et al. |
| 4,999,188 A | 3/1991 | Solodovnik et al. |
| 5,007,940 A | 4/1991 | Berg |
| 5,011,677 A | 4/1991 | Day et al. |
| H915 H | 5/1991 | Gibbs |
| 5,015,423 A | 5/1991 | Eguchi et al. |
| 5,021,059 A | 6/1991 | Kensey et al. |
| 5,032,117 A | 7/1991 | Motta |
| 5,034,324 A | 7/1991 | Shinozaki et al. |
| 5,047,438 A | 9/1991 | Feibush et al. |
| 5,079,274 A | 1/1992 | Schneider et al. |
| 5,091,205 A | 2/1992 | Fan |
| 5,106,903 A | 4/1992 | Vanderhoff et al. |
| 5,108,407 A | 4/1992 | Geremia et al. |
| 5,114,421 A | 5/1992 | Polak |
| 5,116,387 A | 5/1992 | Berg |
| 5,120,349 A | 6/1992 | Stewart et al. |
| 5,125,892 A | 6/1992 | Drudik |
| 5,147,631 A | 9/1992 | Glajch et al. |
| 5,147,937 A | 9/1992 | Frazza et al. |
| 5,149,543 A | 9/1992 | Cohen et al. |
| 5,158,573 A | 10/1992 | Berg |
| 5,167,624 A | 12/1992 | Butler et al. |
| 5,171,214 A | 12/1992 | Kolber et al. |
| 5,171,217 A | 12/1992 | March et al. |
| 5,181,921 A | 1/1993 | Makita et al. |
| 5,190,760 A | 3/1993 | Baker |
| 5,190,766 A | 3/1993 | Ishihara |
| 5,192,301 A | 3/1993 | Kamiya et al. |
| 5,202,352 A | 4/1993 | Okada et al. |
| 5,216,096 A | 6/1993 | Hattori et al. |
| 5,226,911 A | 7/1993 | Chee et al. |
| 5,234,437 A | 8/1993 | Sepetka |
| 5,250,071 A | 10/1993 | Palermo |
| 5,253,991 A | 10/1993 | Yokota et al. |
| 5,256,146 A | 10/1993 | Ensminger et al. |
| 5,260,002 A | 11/1993 | Wang |
| 5,261,916 A | 11/1993 | Engelson |
| 5,262,176 A | 11/1993 | Palmacci et al. |
| 5,263,964 A | 11/1993 | Purdy |
| 5,263,992 A | 11/1993 | Guire |
| 5,288,763 A | 2/1994 | Li et al. |
| 5,290,310 A | 3/1994 | Makower et al. |
| 5,292,332 A | 3/1994 | Lee |
| 5,292,814 A | 3/1994 | Bayer et al. |
| 5,302,369 A | 4/1994 | Day et al. |
| 5,304,195 A | 4/1994 | Twyford, Jr. et al. |
| 5,312,415 A | 5/1994 | Palermo |
| 5,314,974 A | 5/1994 | Ito et al. |
| 5,316,774 A | 5/1994 | Eury et al. |
| RE34,640 E | 6/1994 | Kennedy et al. |
| 5,320,639 A | 6/1994 | Rudnick |
| 5,324,306 A | 6/1994 | Makower et al. |
| 5,328,936 A | 7/1994 | Leifholtz et al. |
| 5,334,216 A | 8/1994 | Vidal et al. |
| 5,336,263 A | 8/1994 | Ersek et al. |
| 5,342,394 A | 8/1994 | Matsuno et al. |
| 5,344,452 A | 9/1994 | Lemperle |
| 5,344,867 A | 9/1994 | Morgan et al. |
| 5,350,397 A | 9/1994 | Palermo et al. |
| 5,354,290 A | 10/1994 | Gross |
| 5,354,295 A | 10/1994 | Guglielmi et al. |
| 5,369,133 A | 11/1994 | Ihm et al. |
| 5,369,163 A | 11/1994 | Chiou et al. |
| 5,382,260 A | 1/1995 | Dormandy, Jr. et al. |
| 5,384,124 A | 1/1995 | Courteille et al. |
| 5,397,303 A | 3/1995 | Sancoff et al. |
| 5,398,851 A | 3/1995 | Sancoff et al. |
| 5,403,870 A | 4/1995 | Gross |
| 5,411,520 A | 5/1995 | Nash et al. |
| 5,417,982 A | 5/1995 | Modi |
| 5,431,174 A | 7/1995 | Knute |
| 5,435,645 A | 7/1995 | Faccioli et al. |
| 5,443,495 A | 8/1995 | Buscemi et al. |
| 5,456,693 A | 10/1995 | Conston et al. |
| 5,468,801 A | 11/1995 | Antonelli et al. |
| 5,469,854 A | 11/1995 | Unger et al. |
| 5,476,472 A | 12/1995 | Dormandy, Jr. et al. |
| 5,484,584 A | 1/1996 | Wallace et al. |
| 5,490,984 A | 2/1996 | Freed |
| 5,494,682 A | 2/1996 | Cohen et al. |
| 5,494,940 A | 2/1996 | Unger et al. |
| 5,512,604 A | 4/1996 | Demopolis |
| 5,514,090 A | 5/1996 | Kriesel et al. |
| 5,525,334 A | 6/1996 | Ito et al. |
| 5,534,589 A | 7/1996 | Hager et al. |
| 5,536,274 A | 7/1996 | Neuss |
| 5,540,680 A | 7/1996 | Guglielmi et al. |
| 5,541,031 A | 7/1996 | Yamashita et al. |
| 5,542,935 A | 8/1996 | Unger et al. |
| 5,553,741 A | 9/1996 | Sancoff et al. |
| 5,556,391 A | 9/1996 | Cercone et al. |
| 5,556,610 A | 9/1996 | Yan et al. |
| 5,558,255 A | 9/1996 | Sancoff et al. |
| 5,558,822 A | 9/1996 | Gitman et al. |
| 5,558,856 A | 9/1996 | Klaveness et al. |
| 5,559,266 A | 9/1996 | Klaveness et al. |
| 5,567,415 A | 10/1996 | Porter |
| 5,569,193 A | 10/1996 | Hofstetter et al. |
| 5,569,449 A | 10/1996 | Klaveness et al. |
| 5,569,468 A | 10/1996 | Modi |
| 5,571,182 A | 11/1996 | Ersek et al. |
| 5,580,575 A | 12/1996 | Unger et al. |
| 5,583,162 A | 12/1996 | Li et al. |
| 5,585,112 A | 12/1996 | Unger et al. |
| 5,595,821 A | 1/1997 | Hager et al. |
| 5,614,204 A | 3/1997 | Cochrum et al. |
| 5,622,657 A | 4/1997 | Takada et al. |
| 5,624,685 A | 4/1997 | Takahashi et al. |
| 5,635,215 A | 6/1997 | Boschetti et al. |
| 5,637,087 A | 6/1997 | O'Neil et al. |
| 5,639,710 A | 6/1997 | Lo et al. |
| 5,648,095 A | 7/1997 | Illum et al. |
| 5,648,100 A | 7/1997 | Boschetti et al. |
| 5,650,116 A | 7/1997 | Thompson |
| 5,651,990 A | 7/1997 | Takada et al. |
| 5,653,922 A | 8/1997 | Li et al. |
| 5,657,756 A | 8/1997 | Vrba |
| 5,681,576 A | 10/1997 | Henry |
| 5,695,480 A | 12/1997 | Evans et al. |
| 5,695,740 A | 12/1997 | Porter |
| 5,698,271 A | 12/1997 | Liberti et al. |
| 5,701,899 A | 12/1997 | Porter |
| 5,715,824 A | 2/1998 | Unger et al. |
| 5,716,981 A | 2/1998 | Hunter et al. |
| 5,718,884 A | 2/1998 | Klaveness et al. |
| 5,723,269 A | 3/1998 | Akagi et al. |
| 5,725,534 A | 3/1998 | Rasmussen |
| 5,733,925 A | 3/1998 | Kunz et al. |
| 5,741,331 A | 4/1998 | Pinchuk |
| 5,746,734 A | 5/1998 | Dormandy, Jr. et al. |
| 5,752,974 A | 5/1998 | Rhee et al. |
| 5,760,097 A | 6/1998 | Li et al. |
| 5,766,147 A | 6/1998 | Sancoff et al. |
| 5,770,222 A | 6/1998 | Unger et al. |
| 5,779,668 A | 7/1998 | Grabenkort |
| 5,785,642 A | 7/1998 | Wallace et al. |
| 5,785,682 A | 7/1998 | Grabenkort |
| 5,792,478 A | 8/1998 | Lawin et al. |
| 5,795,562 A | 8/1998 | Klaveness et al. |
| 5,797,953 A | 8/1998 | Tekulve |
| 5,800,453 A | 9/1998 | Gia |
| 5,800,454 A | 9/1998 | Jacobsen et al. |
| 5,800,455 A | 9/1998 | Palermo et al. |
| 5,807,323 A | 9/1998 | Kriesel et al. |
| 5,813,411 A | 9/1998 | Van Bladel et al. |
| 5,823,198 A | 10/1998 | Jones et al. |
| 5,827,502 A | 10/1998 | Klaveness et al. |
| 5,827,531 A | 10/1998 | Morrison et al. |

| | | | | | | |
|---|---|---|---|---|---|---|
| 5,830,178 | A | 11/1998 | Jones et al. | 6,306,427 B1 | 10/2001 | Annonier et al. |
| 5,833,361 | A | 11/1998 | Funk | 6,312,407 B1 | 11/2001 | Zadno-Azizi et al. |
| 5,840,387 | A | 11/1998 | Berlowitz-Tarrant et al. | 6,315,709 B1 | 11/2001 | Garibaldi et al. |
| 5,846,518 | A | 12/1998 | Yan et al. | 6,322,576 B1 | 11/2001 | Wallace et al. |
| 5,853,752 | A | 12/1998 | Unger et al. | 6,335,384 B1 | 1/2002 | Evans et al. |
| 5,855,615 | A | 1/1999 | Bley et al. | 6,344,182 B1 | 2/2002 | Sutton et al. |
| 5,863,957 | A | 1/1999 | Li et al. | 6,355,275 B1 | 3/2002 | Klein |
| 5,876,372 | A | 3/1999 | Grabenkort et al. | 6,368,658 B1 | 4/2002 | Schwarz et al. |
| 5,877,224 | A | 3/1999 | Brocchini et al. | 6,379,373 B1 | 4/2002 | Sawhney et al. |
| 5,885,216 | A | 3/1999 | Evans, III et al. | 6,388,043 B1 | 5/2002 | Langer et al. |
| 5,885,547 | A | 3/1999 | Gray | 6,394,965 B1 | 5/2002 | Klein |
| 5,888,546 | A | 3/1999 | Ji et al. | 6,423,332 B1 | 7/2002 | Huxel et al. |
| 5,891,130 | A | 4/1999 | Palermo et al. | 6,432,437 B1 | 8/2002 | Hubbard |
| 5,891,155 | A | 4/1999 | Irie | 6,436,112 B2 | 8/2002 | Wensel et al. |
| 5,894,022 | A | 4/1999 | Ji et al. | 6,443,941 B1 | 9/2002 | Slepian et al. |
| 5,895,385 | A | 4/1999 | Guglielmi et al. | 6,476,069 B2 | 11/2002 | Krall et al. |
| 5,895,398 | A | 4/1999 | Wensel et al. | 6,544,503 B1 | 4/2003 | Vanderhoff et al. |
| 5,895,411 | A | 4/1999 | Irie | 6,544,544 B2 | 4/2003 | Hunter et al. |
| 5,899,877 | A | 5/1999 | Leibitzki et al. | 6,545,097 B2 | 4/2003 | Pinchuk et al. |
| 5,902,832 | A | 5/1999 | Van Bladel et al. | 6,575,896 B2 | 6/2003 | Silverman et al. |
| 5,902,834 | A | 5/1999 | Porrvik | 6,589,230 B2 | 7/2003 | Gia et al. |
| 5,922,025 | A | 7/1999 | Hubbard | 6,602,261 B2 | 8/2003 | Greene, Jr. et al. |
| 5,922,304 | A | 7/1999 | Unger | 6,602,524 B2 | 8/2003 | Batich et al. |
| 5,925,059 | A | 7/1999 | Palermo et al. | 6,605,111 B2 | 8/2003 | Bose et al. |
| 5,928,626 | A | 7/1999 | Klaveness et al. | 6,629,947 B1 | 10/2003 | Sahatjian et al. |
| 5,935,553 | A | 8/1999 | Unger et al. | 6,632,531 B2 | 10/2003 | Blankenship |
| 5,951,160 | A | 9/1999 | Ronk | 6,635,069 B1 | 10/2003 | Teoh et al. |
| 5,957,848 | A | 9/1999 | Sutton et al. | 6,638,291 B1 | 10/2003 | Ferrera et al. |
| 5,959,073 | A | 9/1999 | Schlameus et al. | 6,652,883 B2 | 11/2003 | Goupil et al. |
| 6,003,566 | A | 12/1999 | Thibault et al. | 6,669,652 B2 | 12/2003 | Anderson et al. |
| 6,015,546 | A | 1/2000 | Sutton et al. | 6,680,046 B1 | 1/2004 | Boschetti |
| 6,027,472 | A | 2/2000 | Kriesel et al. | 6,699,222 B1 | 3/2004 | Jones et al. |
| 6,028,066 | A | 2/2000 | Unger | 6,969,480 B2 * | 11/2005 | Dalton et al. .................. 264/255 |
| 6,047,861 | A | 4/2000 | Vidal et al. | 7,053,134 B2 | 5/2006 | Baldwin et al. |
| 6,048,908 | A | 4/2000 | Kitagawa | 7,094,369 B2 | 8/2006 | Buiser et al. |
| 6,051,247 | A | 4/2000 | Hench et al. | 7,131,997 B2 | 11/2006 | Bourne et al. |
| 6,056,721 | A | 5/2000 | Shulze | 7,192,546 B2 * | 3/2007 | Franks et al. .................. 264/319 |
| 6,056,844 | A | 5/2000 | Guiles et al. | 2001/0001835 A1 | 5/2001 | Greene, Jr. et al. |
| 6,059,766 | A | 5/2000 | Greff | 2001/0016210 A1 | 8/2001 | Mathiowitz et al. |
| 6,063,068 | A | 5/2000 | Fowles et al. | 2001/0031978 A1 | 10/2001 | Kipke et al. |
| 6,071,495 | A | 6/2000 | Unger et al. | 2001/0036451 A1 | 11/2001 | Goupil et al. |
| 6,071,497 | A | 6/2000 | Steiner et al. | 2001/0051670 A1 | 12/2001 | Goupil et al. |
| 6,073,759 | A | 6/2000 | Lamborne et al. | 2002/0010481 A1 | 1/2002 | Jayaraman |
| 6,090,925 | A | 7/2000 | Woiszwillo et al. | 2002/0054912 A1 | 5/2002 | Kim et al. |
| 6,096,344 | A | 8/2000 | Liu et al. | 2002/0082499 A1 | 6/2002 | Jacobsen et al. |
| 6,099,546 | A | 8/2000 | Gia | 2002/0143348 A1 | 10/2002 | Wallace et al. |
| 6,099,864 | A | 8/2000 | Morrison et al. | 2002/0197208 A1 | 12/2002 | Ruys et al. |
| 6,100,306 | A | 8/2000 | Li et al. | 2003/0007928 A1 | 1/2003 | Gray |
| 6,117,142 | A | 9/2000 | Goodson et al. | 2003/0032935 A1 | 2/2003 | Damiano et al. |
| 6,139,963 | A | 10/2000 | Fujii et al. | 2003/0108614 A1 | 6/2003 | Volkonsky et al. |
| 6,149,623 | A | 11/2000 | Reynolds | 2003/0185895 A1 | 10/2003 | Lanphere et al. |
| 6,159,206 | A | 12/2000 | Ogawa | 2003/0185896 A1 | 10/2003 | Buiser et al. |
| 6,160,084 | A | 12/2000 | Langer et al. | 2003/0187320 A1 | 10/2003 | Freyman |
| 6,162,377 | A | 12/2000 | Ghosh et al. | 2003/0194390 A1 | 10/2003 | Krall et al. |
| 6,165,193 | A | 12/2000 | Greene, Jr. et al. | 2003/0206864 A1 | 11/2003 | Mangin |
| 6,179,817 | B1 | 1/2001 | Zhong | 2003/0215519 A1 | 11/2003 | Schwarz et al. |
| 6,190,373 | B1 | 2/2001 | Palermo et al. | 2003/0225365 A1 | 12/2003 | Greff et al. |
| 6,191,193 | B1 | 2/2001 | Lee et al. | 2004/0028655 A1 * | 2/2004 | Nelson et al. ................. 424/93.2 |
| RE37,117 | E | 3/2001 | Palermo | 2004/0076582 A1 | 4/2004 | DiMatteo et al. |
| 6,214,331 | B1 | 4/2001 | Vanderhoff et al. | 2004/0091543 A1 | 5/2004 | Bell et al. |
| 6,224,630 | B1 | 5/2001 | Bao et al. | 2004/0092883 A1 | 5/2004 | Casey, III et al. |
| 6,224,794 | B1 | 5/2001 | Amsden et al. | 2004/0093014 A1 | 5/2004 | Ho et al. |
| 6,231,586 | B1 | 5/2001 | Mariant | 2004/0096662 A1 * | 5/2004 | Lanphere et al. ............. 428/402 |
| 6,235,224 | B1 | 5/2001 | Mathiowitz et al. | 2004/0101564 A1 | 5/2004 | Rioux et al. |
| 6,238,403 | B1 | 5/2001 | Greene, Jr. et al. | 2004/0111044 A1 | 6/2004 | Davis et al. |
| 6,245,090 | B1 | 6/2001 | Gilson et al. | 2004/0161451 A1 | 8/2004 | Pierce et al. |
| 6,258,338 | B1 | 7/2001 | Gray | 2004/0181174 A2 | 9/2004 | Davis et al. |
| 6,261,585 | B1 | 7/2001 | Sefton et al. | 2004/0186377 A1 | 9/2004 | Zhong et al. |
| 6,264,861 | B1 | 7/2001 | Tavernier et al. | 2005/0025800 A1 | 2/2005 | Tan |
| 6,267,154 | B1 | 7/2001 | Felicelli et al. | 2005/0037047 A1 | 2/2005 | Song |
| 6,268,053 | B1 | 7/2001 | Woiszwillo et al. | 2005/0095428 A1 | 5/2005 | DiCarlo et al. |
| 6,277,392 | B1 | 8/2001 | Klein | 2005/0129775 A1 | 6/2005 | Lanphere et al. |
| 6,280,457 | B1 | 8/2001 | Wallace et al. | 2005/0133046 A1 | 6/2005 | Becker et al. |
| 6,291,605 | B1 | 9/2001 | Freeman et al. | 2005/0196449 A1 | 9/2005 | DiCarlo et al. |
| 6,296,604 | B1 | 10/2001 | Garibaldi et al. | 2005/0226935 A1 | 10/2005 | Kamath et al. |
| 6,296,622 | B1 | 10/2001 | Kurz et al. | 2005/0238870 A1 | 10/2005 | Buiser et al. |
| 6,296,632 | B1 | 10/2001 | Luscher et al. | 2005/0263916 A1 | 12/2005 | Lanphere et al. |
| 6,306,418 | B1 | 10/2001 | Bley | 2006/0045900 A1 | 3/2006 | Richard et al. |
| 6,306,419 | B1 | 10/2001 | Vachon et al. | 2006/0116711 A1 | 6/2006 | Elliott et al. |

| | | | |
|---|---|---|---|
| 2006/0173090 A1 | 8/2006 | Baldwin et al. | |
| 2006/0199009 A1 | 9/2006 | Anderson et al. | |
| 2006/0199010 A1 | 9/2006 | DiCarlo et al. | |
| 2006/0210710 A1 | 9/2006 | Buiser et al. | |
| 2006/0247610 A1 | 11/2006 | Lanphere et al. | |
| 2006/0292300 A1 | 12/2006 | Tan | |
| 2007/0001346 A1* | 1/2007 | Vyakarnam et al. | 264/413 |
| 2007/0004973 A1 | 1/2007 | Tan | |
| 2007/0059375 A1 | 3/2007 | Bourne et al. | |
| 2007/0083219 A1 | 4/2007 | Buiser et al. | |
| 2007/0083226 A1 | 4/2007 | Buiser et al. | |
| 2007/0142859 A1 | 6/2007 | Buiser et al. | |
| 2007/0142893 A1 | 6/2007 | Buiser et al. | |

FOREIGN PATENT DOCUMENTS

| | | |
|---|---|---|
| DE | 233 303 | 2/1986 |
| DE | 3834705 | 4/1990 |
| DE | 94 14 868.6 | 12/1994 |
| DE | 100 26 620 | 3/2002 |
| DE | 203 15 980 U1 | 3/2004 |
| EP | 0 067 459 | 12/1982 |
| EP | 0 122 624 | 10/1984 |
| EP | 0 123 235 | 10/1984 |
| EP | 0 402 031 | 12/1990 |
| EP | 0 422 258 | 4/1991 |
| EP | 0 458 079 | 11/1991 |
| EP | 0 458 745 | 11/1991 |
| EP | 0 470 569 | 2/1992 |
| EP | 0 547 530 | 6/1993 |
| EP | 0 600 529 | 6/1994 |
| EP | 0 623 012 | 11/1994 |
| EP | 0 706 376 | 4/1996 |
| EP | 0 730 847 | 9/1996 |
| EP | 0 744 940 | 12/1996 |
| EP | 0 764 047 | 3/1997 |
| EP | 0 797 988 | 10/1997 |
| EP | 0 820 726 | 1/1998 |
| EP | 0 865 773 | 9/1998 |
| EP | 0 993 337 | 4/2000 |
| EP | 1 547 530 | 6/2005 |
| EP | 1 621 148 | 2/2006 |
| EP | 1 621 149 | 2/2006 |
| EP | 1 738 695 | 1/2007 |
| FR | 2 641 692 | 7/1990 |
| FR | 2 644 056 | 9/1990 |
| JP | 59-196738 | 11/1984 |
| JP | 62-45637 | 2/1987 |
| JP | 4-74117 | 3/1992 |
| JP | 6-57012 | 3/1994 |
| JP | 9-110678 | 4/1997 |
| JP | 9-316271 | 12/1997 |
| JP | 10-130329 | 5/1998 |
| JP | 2000189511 | 7/2000 |
| JP | 2001079011 | 3/2001 |
| JP | 2002-017848 | 1/2002 |
| TW | 421658 | 2/2001 |
| WO | WO 91/12823 | 5/1991 |
| WO | WO 92/21327 | 12/1992 |
| WO | WO 93/19702 | 10/1993 |
| WO | WO 94/06503 | 3/1994 |
| WO | WO 94/10936 | 5/1994 |
| WO | WO 95/03036 | 2/1995 |
| WO | WO 95/22318 | 8/1995 |
| WO | WO 95/33553 | 12/1995 |
| WO | WO 96/22736 | 8/1996 |
| WO | WO 96/37165 | 11/1996 |
| WO | WO 96/39464 | 12/1996 |
| WO | WO 98/04616 | 2/1998 |
| WO | WO 98/10798 | 3/1998 |
| WO | WO 98/26737 | 6/1998 |
| WO | WO 98/47532 | 10/1998 |
| WO | WO 99/00187 | 1/1999 |
| WO | WO 99/12577 | 3/1999 |
| WO | WO 99/42038 | 8/1999 |
| WO | WO 99/43380 | 9/1999 |
| WO | WO 99/57176 | 11/1999 |
| WO | WO 00/23054 | 4/2000 |
| WO | WO 00/32112 | 6/2000 |
| WO | WO 00/40259 | 7/2000 |
| WO | WO 00/53105 | 9/2000 |
| WO | WO 00/71196 | 11/2000 |
| WO | WO 00/74633 | 12/2000 |
| WO | WO 01/66016 | 9/2001 |
| WO | WO 01/70291 | 9/2001 |
| WO | WO 01/72281 | 10/2001 |
| WO | WO 01/76845 | 10/2001 |
| WO | W0 01/93920 | 12/2001 |
| WO | WO 02/11696 | 2/2002 |
| WO | WO 02/096302 | 12/2002 |
| WO | WO 03/013552 | 2/2003 |
| WO | WO 03/051451 | 6/2003 |
| WO | WO 03/082359 | 10/2003 |
| WO | WO 2004/019999 | 3/2004 |
| WO | WO 2004/040972 | 5/2004 |
| WO | WO 2004/073688 | 9/2004 |
| WO | WO 2005/009253 | 2/2005 |

OTHER PUBLICATIONS

Ahuja, A.A., "Platinum Coil Coatings to Increase Thrombogenicity: A Preliminary Study in Rabbits", AJNR Am. J. Neuroradiol. 14:794-798; Jul./Aug. 1993.

Antibody Labeling, http://www.altcorp.com/AffmityLabeling/ablaeling.htm, pp. 1-6, May 20, 2003.

Bachtsi, A.R. et al., "An Experimental Investigation of Enzyme Release from Poly(vinyl alcohol) crosslinked Microspheres", J. Microencapsulation, vol. 12, No. 1, pp. 23-35; 1995.

Barr, J.D., et al., "Polyvinyl Alcohol Foam Particles Sizes and Concentrations Injectable through Microcatheters", JVIR, vol. 9, No. 1, pp. 113-118; 1998.

Barton, P. et al., "Embolization of Bone Metastases," Journal of Vascular and Interventional Radiology, 7(1):81-88 (Jan.-Feb. 1996).

Battinelli, L. et al., "New Class of Poly(vinyl alcohol) Polymrs as Column-Chromatography Stationary Phases for Candida Rugosa Lipase Isoforms Separation", J. Chromatogr A, vol. 753, No. 1, pp. 47-55; 1996.

Beaujeux, R. et al., "Trisacryl Gelatin Microspheres for Therapeutic Embolization, II: Preliminary Clinical Evaluation in Tumors and Arteriovenous Malformations," AJNR Am. J. Neuroradiol., 17:541-548, Mar. 1996.

Berenstein, A. et al., "Catheter and Material Selection for Transarterial Embolization: Technical Considerations. II. Materials.", Radiology, vol. 132, No. 3, pp. 631-639; 1979.

Berenstein, A. et al., "Microembolization Techniques of Vascular Occlusion: Radiologic, Patohologic, and Clinical Correlation", AJNR Am I Neuroradiol, vol. 2, No. 3, pp. 261-267; 1981.

Berkowitz, R.P. et al., "Vaginal Expulsion of Submucosal Fibroids After Uterine Artery Embolization", Journal of Reproductive Medicine, vol. 44, No. 4, pp. 373-376; Apr. 1999.

Bhattacharya et al., "Research & Aneurysms," Interventional Neuroradiology, 11(Suppl. 2):87-94 (Oct. 2005).

Boston Scientific Target, IDC™ Interlocking Coil, 1 page, (2007).

Bracard et al., "AVMs," Interventional Neuroradiology, 11(Suppl. 2):178-184 (Oct. 2005).

Bradley, E.A. et al., "Transcatheter Uterine Artery Embolisation to Treat Large Uterine Fibroids", British Journal of Obstetrics and Gynaecology, vol. 105, pp. 235-240; Feb. 1998.

Brockmann, J. et al., "Radiolabeling of p-Bz-DOTA-CD-11c antibody with 88Y: Conjugation, Labeling, Biodistribution studies", http://www.kernchemie.uni-mainz.de/downloads/jb2000/b14_brockmann.pdf , 2 pages, 2000.

Bruix, J. et al., "Transarterial Embolization Versus Symptomatic Treatment in Patients With Advanced Hepatocellular Carcinoma: Results of a Randomized, Controlled Trial in a Single Institution", Hepatology, Jun. 1998, vol. 27, No. 6, pp. 1578-1583, http://www.hepatitis-central.com/hcv/hcc/embolization/references.html.

Buhle, Jr. EL, "Re: Re: Hepatic Arterial Embolization", UCLA Medicine Online, Mar. 10, 1996, http://wvvw.meds.com/archive/mol-cancer/1996/msg00128.html, 2 pages.

Burczak, et al., "Long-term in vivo performance and biocompatibility of poly (vinyl alcohol) hydrogel macrocapsules for hybrid-type artificial pancreas", Biomaterials, vol. 17, No. 24, pp. 2351-2356, 1996.

Burczak, et al., "Polymeric materials for biomedical purposes obtained by radiation methods. V. hybrid artificial pancreas", Polim Med, vol. 245, No. 1-2, pp. 45-55, 1994 (English Summary included).

Capozza et al., "Endoscopic treatment of vesico-ureteric reflux and urinary incontinence: technical problems in the paediatric patient," British Journal of Urology, 75(4):538-542 (Apr. 1995).

Carroll, B.A. et al., "Microbubbles as Ultrasonic Contrast Agents", Investigative Radiology, vol. 14, No. 3, p. 374, Supplement to May-Jun. 1979.

Carroll, B.A. et al., "Gelatin Encapsulated Nitrogen Microbubbles as Ultrasonic Contrast Agents", Journal of Clinical and Laboratory Research, vol. 15, No. 1, pp. 260-266, Feb. 1980.

Carstensen, E.L. et al., "Determination of the Acoustic Properties of Blood and its Components", Journal of Acoustical Society of America, vol. 25, No. 2, pp. 286-289, Mar. 1953.

Cekirge et al., "Interlocking Detachable Coil Occlusion in the Endovascular Treatment of Intracranial Aneurysms: Preliminary Results," AJNR Am. J. Neuroradiol., 17:1651-1657 (Oct. 1996).

Choe, et al., "An experimental study of embolic effect according to infusion rate and concentration of suspension in transarterial particulate embolization", Invest Radiol, vol. 32, No. 5, pp. 260-270, 1997.

Chuang et al., "Experimental Canine Hepatic Artery Embolization with Polyvinyl Alcohol Foam Particles", Departments of Diagnostic Radiology and Veterinary Medicine, The University of Texas, M.D. Anderson Hospital and Tumor Institute at Houston, Texas, pp. 21-25, Oct. 1982.

Cirkel, U. et al., "Experience with Leuprorelin Acetate Depot in the Treatment of Fibroids: A German Multicentre Study", Clinical Therapeutics, vol. 14, Suppl. A, 1992.

Clarian Health Methodist—Indiana Lions Gamma Knife Center, "Arteriovenous Malformation,"http://www.clarian.com/tyhealth/gammaknife/cond_arter.asp, 4 pages, Last Updated on Mar. 20, 2000.

Collice et al., "Neurosurgery & Aneurysms," Interventional Neuroradiology, 11(Suppl. 2):226-231 (Oct. 2005).

Colombo M, "Treatment of Hepatocellular Carcinoma", Journal of Viral Hepatitis, 4(Suppl. 1):125-130 (1997), http://home.texoma.net/~moreland/stats/hcc-9.html.

Concentric Medical, Inc.— Product Information (3 pages), 2002.

"Contour® PVA Particles," Boston Scientific, http://www.bostonscientific.com, 2 pages (retrieved from the internet on Sep. 6, 2005).

"Contour SE™ Microspheres," Boston Scientific, http://www.bostonscientific.com, 4 pages (retrieved from the internet on Sep. 6, 2005).

Cotroneo et al., "Aneurysms," Interventional Neuroradioldgy, 11(Suppl. 2):212-216 (Oct. 2005).

Cruise et al., "In Vitro and In Vivo Characterization of a Hydrogel-Based Aneurysm Embolization System," Society for Biomaterials 28th Annual Meeting Transactions, p. 203 (2002).

Deasy, P. B., "Microencapsulation and Related Drug Processes", New York, NY, Marcel Dekker, Inc., 345 pages, 1984 (Table of Contents only).

de Gast, A.N. et al., "Transforming Growth Factor β-coated Platinum Coils for Endovascular Treatment of Aneurysms: An Animal Study", Neurosurgery, vol. 49, No. 3, pp. 690-696, Sep. 2001.

Derdeyn, et al., "Collagen-coated acrylic microspheres for embolotherapy: in vivo and in vitro characteristics", American Journal of Neuroradiology, vol. 18, No. 4, pp. 647-653, 1997.

Derdeyn, et al., "Polyvinyl alcohol particle size and suspension characteristics", American Journal of Neuroradiology, vol. 16, pp. 1335-1343, 1995.

DiLuccio et al., "Sustained-Release Oral Delivery of Theophylline by Use of Polyvinyl Alcohol and Polyvinyl Alcohol-Methyl Acrylate Polymers", Journal of Pharmaceutical Sciences, vol. 83, No. 1, pp. 104-106, Jan. 1994.

Ducati et al., "Aneurysms," Interventional Neuroradiology, 11(Suppl. 2):95-99 (Oct. 2005).

Duckwiler et al., "Catheters, embolic agents spark neurointervention," Diagnostic Imaging, 16(5):66-72 (May 1994).

Eskridge, "Interventional Neuroradiology," Radiology, 172:991-1006 (Nov. 1989).

Feldman, L. et al., "Transcatheter Vessel Occlusion: Angiographic Results Versus Clinical Success", Radiology, vol. 147, pp. 1-5, Apr. 1983.

Ferrofluids, Physical Properties and Applications, Ferrofluidics Corp., Nashua, NH, 5 pages, 1986.

FeRx Incorporated, FERX Profile, http://www.biotechshares.com/FERX.htm, 4 pages (Retrieved from the internet on Jun. 26, 2003).

"Fibroid Treatment Collective—Fibroid Embolization," 2 pages, http://www.fibroids.org, (2007).

Fritzsch, T. et al., "SH U 508, A Transpulmonary Echocontrast Agent", Investigative Radiology, vol. 25, Supplement 1, pp. S160-S161, Sep. 1990.

Fujimoto, S. et al., "Biodegradable Mitomycin C Microspheres Given Intra-Arterially for Inoperable Hepatic Cancer", Cancer, vol. 56, pp. 2404-2410, 1985.

Gander, et al., "Effect of polymeric network structure on drug release from cross-linked poly(vinyl alcohol) micromatrices", Pharm Res, vol. 6, No. 7, pp. 578-584, 1989.

Germano, et al., "Histopathological follow-up study of 66 cerebral arteriovenous malformations after therapeutic embolization with polyvinyl alcohol", J Neurosurg, vol. 76, No. 4, pp. 607-614, 1992.

Geschwind et al., "Chemoembolization of Liver Tumor in a Rabbit Model: Assessment of Tumor Cell Death with Diffusion-Weighted MR Imaging and Histologic Analysis", Journal of Vascular and Interventional Radiology, vol. 11, No. 10, pp. 1244-1255, Dec. 2000.

Gilbert, W.M. et al., "Angiographic Embolization in the Management of Hemorrhagic Complications of Pregnancy", American Journal of Obstetrics and Gynecology, vol. 166, No. 2, pp. 493-497, Feb. 1992.

Gohel, et al., "Formulation design and optimization of modified-release microspheres of diclofenac sodium", Drug Dev Ind Pharm, vol. 25, No. 2, pp. 247-251, 1999.

Goldberg, B.B., "Ultrasonic Cholangiography", Radiology, vol. 118, pp. 401-404, Feb. 1976.

Goodwin, et al., "Overview of embolic agents and their indications", Eleventh Annual International Symposium on Endovascular Therapy, pp. 303-306, 1999.

Goodwin, et al., "Preliminary experience with uterine artery embolization for uterine fibroids", Journal of Vascular and Interventional Radiology, vol. 8, No. 4, pp. 517-526, 1997.

Gramiak et al., "Echocardiography of the Aortic Root," Investigative Radiology, 3(5):356-366 (Sep.-Oct. 1968).

Gramiak, R. et al., "Ultrasound Cardiography: Contrast Studies in Anatomy and Function", Radiology, vol. 92, No. 5, pp. 939-948, Apr. 1969.

Grandfils, et al., "Preparation of poly (D,L) lactide microspheres by emulsion solvent evaporation, and their clinical implications as a convenient embolic material", J Biomed Mater Res, vol. 26, No. 4, pp. 467-479, 1992.

Greenwood, L.H. et al., "Obstetric and Nonmalignant Gynecologic Bleeding: Treatment with Angiographic Embolization", Radiology, vol. 164, No. 1, pp. 155-159, Jul. 1987.

Guglielmi Detachable Coils (GDC); http://vvww.neurosurgery.pitt.edu/endovascular/treatments/gdc.html, Jun. 2005, pp. 1-3.

Gupta et al., "Plasma-induced graft polymerization of acrylic acid onto poly(ethylene terephthalate) films: characterization and human smooth muscle cell growth on grafted films," Biomaterials, 23:863-871 (2002).

Halstenberg et al., "Biologically Engineered Protein-graft-Poly(ethylene glycol) Hydrogels: A Cell Adhesive and Plasmin-Degradable Biosynthetic Material for Tissue Repair," Biomacromolecules, 3(4):710-723 (2002).

Hamada et al., "Embolization with Cellulose Porous Beads, II: Clinical Trial," AJNR Am. J. Neuroradiol., 17:1901-1906 (Nov. 1996).

Hirano et al., "Transcutaneous Intrafold Injection for Unilateral Vocal Fold Paralysis: Functional Results," Ann. Otol. Rhinol Laryngol., 99(8):598-604 (Aug. 1990).

Hon-Man et al., "Miscellanea," Interventional Neuroradiology, 11(Suppl. 2):159-164 (Oct. 2005).

Horak et al., "Hydrogels in endovascular embolization. I. Spherical particles of poly (2-hydroxyethyl methacrylate) and their medico-biological properties", Biomaterials, 7(3):188-192 (May 1986).

Horak et al., "Hydrogels in endovascular embolization. II. Clinical use of spherical particles", Biomaterials, 7(6):467-470 (Nov. 1986).

"How Matrix™ Detachable Coils Work," 1 page, (2007).

Huang et al., "Percutaneous endovascular embolization of intracerebral arteriovenous malformations. Experience in 72 cases", Chin Med J, vol. 108, No. 6, pp. 413-419, 1995.

"Injectable Tissue Implant Could Repair Ravages of Surgery", Clemson University, Biotech Week, Oct. 22, 2003, p. 117.

Jack, et al., "Radiolabeled polyvinyl alcohol particles: a potential agent to monitor embolization procedures", Int J Rad Appl Instrum B, vol. 13, No. 3, pp. 235-243, 1986.

Jiaqi, Y. et al., "A New Embolic Material: Super Absorbent Polymer (SAP) Microsphere and Its Embolic Effects," Nippon Acta Radiologica, 56:19-24 (1996) (English Abstract included).

Jones, S.K. et al., "Experimental Examination of a Targeted Hyperthermia System Using Inductively Heated Ferromagnetic Microspheres in Rabbit Kidney", Phys. Med. Biol., vol. 46, No. 2, pp. 385-398, Feb. 2001, www.iop.org/Journals/pb.

Joy C, et al., "Use of Preoperative Embolization in the Treatment of Vascular Metastatic Lesions of the Spine," http://www.aaos.org/wordhtml/anmeet91/scipro/ppr472.htm, Mar. 12, 1991.

Kai, et al., "The utility of the microcrystalline cellulose sphere as a particulate embolic agent: an experimental study", American Journal of Radiology, vol. 21, No. 6, pp. 1160-1163, 2000.

Kallmes, D.F. et al., "In Vitro Proliferation and Adhesion of Basic Fibroblast Growth Factor-producing Fibroblasts on Platinum Coils", Radiology, vol. 206, No. 1, pp. 237-243, Jan. 1998.

Kallmes et al., "Platinum Coil-mediated Implantation of Growth Factor-secreting Endovascular Tissue Grafts: An in Vivo Study," Radiology, 207(2):519-523 (May 1998).

Kan, et al., "In vivo microscopy of the liver after injection of lipiodol into the hepatic artery and portal vein in the rat", Acta Radiologica, vol. 30, pp. 419-425, 1989.

Kerber, C., "Balloon Catheter with a Calibrated Leak", Radiology, vol. 120, pp. 547-550, Sep. 1976.

Kerber et al., "Polyvinyl Alcohol Foam: Prepackaged Emboli for Therapeutic Embolization", American Journal Roentgenol, vol. 130, pp. 1193-1194, Jun. 1978.

Kerber, "Flow-Controlled Therapeutic Embolization: A Physiologic and Safe Technique", AJR, vol. 134, pp. 557-561, Mar. 1980.

Kim, et al., "Composite poly(vinyl alcohol) beads for controlled drug delivery", Pharm Res, vol. 9. No. 1, pp. 10-16, 1992.

Kim et al., "Poly(vinyl alcohol) beads with core-shell structure for drug delivery," Cosmetic and Pharmaceutical Applications of Polymers, Plenum Press, New York, pp. 209-214 (1991).

Kochan, J.P. et al., "Interventional Neuroradiology: Current Practices and Techniques at Temple University Hospital," http://www.temple.edu/radiology/stroke.html, 5 pages, (2007).

Kominami et al., "Complications," Interventional Neuroradiology, 11(Suppl. 2):191-195 (Oct. 2005).

Krinick et al., "A polymeric drug delivery system for the simultaneous delivery of drugs activatable by enzymes and/or light," J. Biomater. Sci. Polymer Edn, 5(4):303-324 (1994).

Kuhn, R. et al., "Embolic Occlusion of the Blood Supply to Uterine Myomas: Report of 2 Cases", Aust. NZ. J. Obstet. Gynaecol., vol. 39, No. 1, pp. 120-122, Feb. 1999.

Kurata, et al., "Preoperative embolization for meningiomas using PVA particles", No Shinkei Geka, vol. 20, No. 4, pp. 367-373, 1992 (English Abstract included).

Kurbatova, G.T. et al., "Magnetically-guided Anesthetics Based on Highly Dispersed Iron Powders Coated by Polyacrylamide", Biofizika, vol. 47, No. 2, pp. 331-337, Mar.-Apr. 2002, http://intapp.medscape.com/px/medlineapp (English Abstract included).

Kurosaki et al., "Evaluation of PVA-Gel Spheres as GI-Transit Time Controlling Oral Drug Delivery System", Proceedings of the 19th International Symposium on Controlled Release of Bioactive Materials, Orlando, Florida, pp. 273-274, Jul. 26-31, 1992.

Kusano, et al., "Low-dose particulate polyvinylalcohol embolization in massive small artery intenstinal hemorrahage. Experimental and clinical results", Invest Radiol, vol. 22, No. 5, pp. 388-392, 1987.

Labarre et al., "Complement activation by substituted polyacrylamide hydrogels for embolisation and implantation", Biomaterials, vol. 23, pp. 2319-2327, 2002.

Lammer, et al., "Transcatheteral embolization with polyvinyl alcohol—technic and experimental studies", Rontgenblatter, vol. 36, No. 1, pp. 10-14, 1983 (English Abstract included).

Latchaw et al., "Polyvinyl Foam Embolization of Vascular and Neoplastic Lesions of the Head, Neck, and Spine", Radiology, vol. 131, pp. 669-679, Jun. 1979.

Laurent, "Materials and biomaterials for interventional radiology," Biomed. & Pharmacother., 52:76-88 (1998).

Lendlein, A. et al., "Biodegradable, Elastic Shape-Memory Polymers for Potential Biomedical Applications", Science, vol. 296, pp. 1673-1676, May 31, 2002.

Leung et al., "Determinants of Postembolization Syndrome after Hepatic Chemoembolization", Journal of Vascular and Interventional Radiology, vol. 12, No. 3, pp. 320-326, Mar. 2001.

Leventon, William, "Hemocompatible Coatings for Blood-Contacting Devices", Medical Device & Diagnostic Industry: Coating Technologies—New Methods to Ensure Blood Compatibility, vol. 25, No. 8, pp. 62-67, Aug. 2003.

Levy et al., "Transcatheter Uterine Artery Embolization for the Treatment of Symptomatic Uterine Fibroid Tumors," Journal of Women's Imaging, 2(4):168-175 (2000).

Lipman, "Uterine artery embolization for the treatment of symptomatic uterine fibroids: A review," Applied Radiology, 29(7):15-20 (Jul. 2000).

Lowery, C.L. et al., "Screening Tests for Intrauterine Growth Retardation: A Comparison of Umbilical Artery Doppler to Real-Time Ultrasound", Echocardiography, vol. 7, No. 2, pp. 159-164, Mar. 1990.

Marich, K.W. et al., "Real-Time Imaging with a New Ultrasonic Camera: Part I, In Vitro Experimental Studies on Transmission Imaging of Biological Structures", Journal of Clinical Ultrasound, vol. 3, No. 1, pp. 5-16, Mar. 1975.

Markoff, et al., "Uterine arteriovenous malformation successfully embolized with a liquid polymer, isobutyl 2-cyanoacrylate", Am. J. Obstet. Gynecol., 155:659-660 (Sep. 1986).

Marks et al., "A Mechanically Detachable Coil for the Treatment of Aneurysms and Occlusion of Blood Vessels," AJNR Am. J. Neuroradiol., 15:821-827 (May 1994).

Markus et al., "Experimental Aspects of High-Intensity Transient Signals in the Detection of Emboli," J. Clin. Ultrasound., 23(2):81-87 (Feb. 1995).

Maruhashi, "Modified Polyvinyl Alcohols I and II," Polyvinyl Alcohol—Developments, John Wiley & Sons, Chichester, England, pp. 160-161 and pp. 186-191 (1992).

Marx, W. F. et al., "Endovascular Treatment of Experimental Aneurysms by Use of Biologically Modified Embolic Devices: Coil-mediated Intraaneurysmal Delivery of Fibroblast Tissue Allografts", AJNR. Am. J. Neuroradiol., vol. 22, pp. 323-333, Feb. 2001.

Mather, P.T., Research Group Homepage, Basic Goals and Methods, http://www.ims.uconn.edu/~mather, 4 pages, (2007).

"Matrix® Detachable Coils," Boston Scientific, http://www.bostonscientific.com, 3 pages (Retrieved from the Internet on Jul. 13, 2005).

Matsumaru, et al., "Embolic materials for endovascular treatment of cerebral lesions", J Biomater Sci Polym Ed, vol. 8, No. 7, pp. 555-569, 1997.

Matsumoto, H. et al., "Basic Fibroblast Growth Factor Released from a Platinum Coil with a Polyvinyl Alcohol Core Enhances Cellular Proliferation and Vascular Wall Thickness: An In Vitro and In Vivo Study", Neurosurgery, vol. 53, No. 2, pp. 402-408, Aug. 2003.

Matsumoto, Y. et al., "Room-Temperature Ferromagnetism in Transparent Transition Metal-Doped Titanium Dioxide", Science, vol. 291, pp. 854-856, Feb. 2, 2001, www.sciencemag.org.

Mavligit, G. et al., "Gastrointestinal Leiomyosarcoma Metastatic to the Liver," Cancer, 75(8):2083-2088 (Apr. 15, 1995).

McIvor, J. et al., "Pregnancy After Uterine Artery Embolization to Control Haemorrhage from Gestational Trophoblastic Tumour", British Journal of Radiology, vol. 69, No. 823, pp. 624-629, Jul. 1996.

MerocelXL Sponge with Hytrol, http://www.xomed.com/newproducts/merocelxl_earwick.asp, 3 pages, 2001.

"Micrus Corporation Announces Encouraging Results of a Modified Coil, Cerecyte, for the Treatment of Cerebral Aneurysms," Business Wire, 2 pages (Nov. 19, 2003).

Mid-America Interventional Radiological Society, "New Treatment for Uterine Fibroids Avoids Surgery," http://www.mirs.org/fibroids.htm, 6 pages, Submitted in Oct. 1999.

Moroz, P. et al., "Arterial Embolization Hyperthermia in Porcine Renal Tissue", Journal of Surgical Research, vol. 105, No. 2, pp. 209-214, Jun. 15, 2002.

Moroz, P. et al., "Hepatic Clearance of Arterially Infused Ferromagnetic Particles", Int. J. Hyperthermia, vol. 19, No. 1, pp. 23-24, Feb. 2003, http://www.tandf.co.uk/journals.

Murphy, "Endovascular procedures," Johns Hopkins Interventional Neuroradiology [online], http://www.brainaneurysms.net/procedures/neurovasc_aneurysm.htm, 2 pages (retrieved from the Internet on Feb. 17, 2005).

Murphy et al., "Mechanical Detachable Platinum Coil: Report of the European Phase II Clinical Trial in 60 Patients," Radiology, 219:541-544 (2001).

Nakabayashi, et al., "Evaluation of particulate embolic materials with MR imaging, scanning electron microscopy, and phase-contrast microscopy", American Journal of Neuroradiology, vol. 18, No. 3, pp. 485-491, 1997.

Nakstad, et al., "Embolization of intracranial arteriovenous malformations and fistulas with polyvinyl alcohol particles and platinum fibre coils", Neuroradiology, vol. 34, No. 4, pp. 348-351, 1992.

Namiki, "Application of Teflon Paste for Urinary Incontinence—Report of 2 Cases," Uro. Int., 39:280-282 (1984).

Nash, et al., "Modifications of polystyrenic matrices for the purification of proteins. II. Effect of the degree of glutaraldehyde-poly(vinyl alcohol) crosslinking on various dye ligand chromatography systems", J Chromatogr A, vol. 776, No. 1, pp. 55-63, 1997.

Nikishin LF et al., "Interventional radiology in diffuse toxic goiter", European Congress of Radiology, Abstract 9041, 1999, http://www.ecr.org/conferences/ecr1999/sciprg/abs/p090041.htm, 7 pages.

Ophir, et al., "Ultrasonic backscatter from contrast producing collagen microspheres", Ultrasonic Imaging, vol. 2, pp. 67-77, 1980.

Oregon Heath Sciences University, "Fibroid Embolization," http://www.uhmc.edu/dotter-fibroid, 34 pages, (2007).

Orsini, L. F. et al., "Pelvic Organs in Premenarcheal Girls: Real-Time Ultrasonography", Radiology, vol. 153, No. 1, pp. 113-116, Oct. 1984.

Parker, et al., "A particulate contrast agent with potential for ultrasound imaging of liver", Ultrasound in Medicine and Biology, vol. 13, No. 9, pp. 555-566, 1987.

Pasquini et al., "Aneurysms," Interventional Neuroradiology, 11(Suppl. 2):136-143 (Oct. 2005).

Pedley et al., "Hydrogels in Biomedical Applications," British Polymer Journal, 12:99-110 (Sep. 1980).

Pérez Higueras et al., "Fistulae," Interventional Neuroradiology, 11(Suppl. 2):123-129 (Oct. 2005).

Pesant A.C. et al., "Dural fistulas involving the cavernous sinus: Treatment by embolization—7 cases", European Congress of Radiology, Abstract 3-088, 1997, http://www.ecr.org/conferences/ecr1997/sciprg/abs/9703088p.htm, 1 page.

Phillips, D. R. et al., "Experience with Laparoscopic Leiomyoma Coagulation and Concomitant Operative Hysteroscopy", J. Am. Assoc. Gynecol. Laparosc, vol. 4, No. 4, pp. 425-533, Aug. 1997.

Physicians' Desk Reference Family Guide to Women's Health, "Chapter 7—Common Disorders of the Reproductive System," http://www.healthsquare.com/pdrfg/wh/chapters/wh1ch01.htm, 24 pages (2007).

Piske et al., "CT & MRI," Interventional Neuroradiology, 11(Suppl. 2):100-106 (Oct. 2005).

Politano et al., "Periurethral Teflon Injection for Urinary Incontinence," The Journal of Urology, 111:180-183 (1974).

Poppe, W. et al., "Pregnancy after Transcatheter Embolization of a Uterine Arteriovenous Malformation", Am. J. Obstet. Gynecol., vol. 156, No. 5, pp. 1179-1180, May 1987.

Pritchard, et al., "Poly(Vinyl Alcohol): Basic Properties and Uses", London, England: Gordon and Breach Science Publishers, pp. 95-97, 1970.

Progelhof et al., "Table 4.21. Properties of electrical insulating films (101)," Polymer Engineering Principles: Properties, Processes, and Tests for Design, Hanser Publishers, Munich, p. 383 (1993).

"Providing Superior Coils, Components, and Assemblies for Medical Devices," Heraeus Vadnais, Inc. [online], http://www.vadtec.com, 6 pages (retrieved from the Internet on Feb. 22, 2005).

Pryor J. and Berenstein A., "Epistaxis (Nose-bleeds)," http://www.wehealny.org/inn/Radiology/nosebleeds.html, 1 page, (2007).

"Pulmonary artery pseudoaneurysm/aneurysm," http://www.mamc.amedd.army.mil/williams/chest/vascular/paaneurysm/paaneyrysm.htm, 2 pages, (2007), Purdy, et al., "Arteriovenous malformations of the brain: choosing embolic materials to enhance safety and ease of excision", J Neurosurg, vol. 77, No. 2, pp. 217-222, 1992.

Quisling, et al., "Histopathology analysis of intraarterial polyvinyl alcohol microemboli in rat cerebral cortex", American Journal of Neuroradiology, vol. 5, pp. 101-104, 1984.

Rajan et al., "Sarcomas Metastatic to the Liver: Response and Survial after Cisplatin, Doxorubicin, Mitomycin-C, Ethiodol, and Polyvinyl Alcohol Chemoembolization", Journal of Vascular and Interventional Radiology, vol. 12, No. 2, pp. 187-193, Feb. 2001.

Ramos, et al., "Tumor vascular signals in renal masses: detection with Doppler US", Radiology, vol. 168, No. 3, pp. 633-637, 1988.

Ravina, J.H. et al., "Advantage of Pre-Operative Embolization of Fibroids: About a Multicentric Set of 31 Cases", Contracept. Fertil. Sex., vol. 23, No. 1, pp. 45-49, Jan. 1995 (English Abstract included).

Ravina, J.H. et al., "Arterial Embolisation to Treat Uterine Myomata", Lancet, vol. 346, pp. 671-674, Sep. 9, 1995.

Ravina, J.H. et al., "Interest of Particulate Arterial Embolization in the Treatment of Some Uterine Myoma", Bull. Acad. Natle. Med., vol. 181, No. 2, pp. 233-246, Feb. 4, 1997 (English Summary included).

Repa, I. et al., "Mortalities Associated with Use of a Commercial Suspension of Polyvinyl Alcohol," Radiology, 170(2):395-399 (Feb. 1989).

Rhine et al., "Polymers for Sustained Macromolecule Release: Procedures to Fabricate Reproducible Delivery Systems and Control Release Kinetics," Journal of Pharmaceutical Sciences, 69(3):265-270 (Mar. 1980).

Rump, A. et al., "Pharmacokinetics of Intraarterial Mitomycin C in the Chemoembolisation Treatment of Liver Metastases," Gen. Pharmac., 27(4):669-671 (1996).

Schetky, "Shape-Memory Alloys," Encyclopedia of Chemical Technology, Third Edition, vol. 20, John Wiley & Sons, New York, pp. 726-736 (1982).

Schlief, R. et al., "Enhanced Color Doppler Echocardiography of the Left Heart After Intravenous Injection of a New Saccharide Based Agent in Humans", Circulation, vol. 82, No. 2, p. 28, Oct. 1990 (Abstract).

Schlief, R. et al., "Successful Opacification of the Left Heart Chamber on Echocardiographic Examination after Intravenous Injection of a New Saccharide Based Contrast Agent", Echocardiography, vol. 7, No. 1, pp. 61-64, Jan. 1990.

Schwarz et al., "The acoustic filter: An ultrasonic blood filter for the heart-lung machine," J. Thorac. Cardiovasc. Surg., 104(6):1647-1653 (Dec. 1992).

Sellar et al., "Fistulae," Interventional Neuroradiology, 11 (Suppl. 2):130-135 (Oct. 2005).

Shafik, "Intraesophageal Polytef injection for the treatment of reflux esophagitis," Surg. Endosc., 10:329-331 (1996).

Shape Shifters, http://www.sciam.com/tehbiz/0501scicit6.html, 3 pages, 2001.

Shung, K.K. et al., "Scattering of Ultrasound by Blood", IEEE Transactions on Biomedical Engineering, vol. BME-23, No. 6, pp. 460-467, Nov. 1976.

Sigelmann, R.A. et al., "Analysis and Measurement of Ultrasound Backscattering from an Ensemble of Scatters Excited by Sine-Wave Bursts", Journal of Acoustical Society of America, vol. 53, No. 4, pp. 1351-1355, Apr. 1973.

SIR-Spheres (Yttrium-90 Microspheres), pp. 1-12, (2007).

SIR-Spheres, Radioactive Implant (Yttrium-90 Microspheres), Sirex Medical, Inc., San Diego, CA, Nov. 6, 2000, pp. 1-15.

Sirtex Medical Limited—Product Description, http://www.sirtex.com/?p=72, 3 pages (Retrieved from the internet on May 27, 2003).

Sirtex Medical Limited—Targeted Radiotherapy with SIR-Spheres, http://www.sirtex.com/?p=57, 2 pages (Retrieved from the internet on May 27, 2003).

Siskin et al., "Pathologic Evaluation of a Spherical Polyvinyl Alcohol Embolic Agent in a Porcine Renal Model," J. Vasc. Interv. Radiol., 14:89-98 (2003).

Skotland, T. et al., "In Vitro Stability Analyses as a Model for Metabolism of Ferromagnetic Particles (Clariscan3), a Contrast Agent for Magnetic Resonance Imaging", J. Pharm. Biomed. Anal., vol. 28, No. 2, pp. 323-329, Apr. 15, 2002.

"Smart Sutures Tie Themselves", Apr. 26, 2002, http://www.sciam.com/article.cfm?articleID=00047706-121F-1CD0-B4A8809EC588, 2 pages.

Smith et al., "Evaluation of Polydimethylsiloxane as an alternative in the Endoscopic Treatment of Vesicoureteral Reflux," The Journal of Urology, 152:1221-1224 (Oct. 1994).

Smith et al., "Left Heart Opacification with Peripheral Venous Injection of a New Saccharide Echo Contrast Agent in Dogs", JACC, vol. 13, No. 7, pp. 1622-1628, Jun. 1989.

Spickler, et al., "The MR appearance of endovascular embolic agents in vitro with clinical correlation", Comput Med Imaging Graph, vol. 14, No. 6, pp. 415-423, 1990.

Spies JB, "Georgetown University Medical Center. Uterine Fibroid Embolization (UFE). An alternative to surgery for patients with uterine fibroids. Literature Review," http://www.fibroidoptions.com/pr-lit.htm, 6 pages, Sep. 1, 2001.

Stancato-Pasik, A. et al., "Obstetric Embolotherapy: Effect on Menses and Pregnancy", Radiology, vol. 204, No. 3, pp. 791-793, Sep. 1997.

Stein, R. et al., "Targeting Human Cancer Xenografts with Monoclonal Antibodies Labeled Using Radioiodinated, Diethylenetriaminepentaacetic Acid-appended Peptides", Clinical Cancer Research, vol. 5, No. 10, pp. 3079-3087, Oct. 1999 (Supplement).

Strasnick et al., "Transcutaneous Teflon® Injection for Unilateral Vocal Cord Paralysis: An Update," The Laryngoscope, 101:785-787 (Jul. 1991).

Stridbeck, H. et al, "Collateral Circulation Following Repeated Distal Embolization of the Hepatic Artery in Pigs," Invest. Radiol., 19(3):179-183 (1984).

Strother et al., "Aneurysms," Interventional Neuroradiology, 11(Suppl. 2):200-205 (Oct. 2005).

Strunk, et al., "Treatment of congenital coronary arteriovenous malformations with microparticle embolization", Cathet Cardiovasc Diagn, vol. 22, No. 2, pp. 133-136, 1991.

Swanson DA et al., "The role of embolization and nephrectomy in the treatment of metastatic renal carcinoma", Urologic Clinics of North America, 7(3):719-730, 1980. University of Pennsylvania Cancer Center—Oncolink, http://www.oncolink.upenn.edu/pdg_html/cites/00/00585.html.

Tabata et al', "Tumor accumulation of poly(vinyl alcohol) of different sizes after intravenous injection", Journal of Controlled Release, vol. 50, pp. 123-133, Jan. 2, 1998.

Tadavarthy et al., "Polyvinyl Alcohol (Ivalon)—A New Embolic Material", The American Journal of Roentgenology Radium Therapy and Nuclear Medicine, vol. 125, No. 3, pp. 609-616, Nov. 1975.

Tadavarthy et al., "Polyvinyl Alcohol (Ivalon) as an Embolizing Agent", Seminars in Interventional Radiology, vol. 1, No. 2, pp. 101-109, Jun. 1984.

Tamatani, S. et al., "Histological Interaction of Cultured Endothelial Cells and Endovascular Embolic Materials Coated with Extracellular Matrix", J. Neurosurg., vol. 86, No. 1, pp. 109-112, Jan. 1997.

Tamatani et al., "Radiologic and Histopathologic Evaluation of Canine Artery Occlusion after Collagen-Coated Platinum Microcoil Delivery," American Journal of Neuroradiology, 20:541-545 (1999).

Tanaka et al., "Radiologic Placement of Side-Hole Catheter With Tip Fixation for Hepatic Arterial Infusion Chemotherapy," JVIR, vol. 14, pp. 63-68, 2003.

Tao, et al., "Study of microspheres for embolization of hepatic artery", Acta Pharmaceutica Sinica, vol. 23, No. 1, pp. 55-60, 1988.

Tao, et al., "Study of microspheres for embolization of hepatic artery", (Translation) Acta Pharmaceutica Sinica, vol. 23, No. 1, pp. 55-60, 1988.

Terada, et al., "Preoperative embolization of meningiomas fed by ophthalmic branch arteries", Surg Neurol, vol. 45, No. 2, pp. 161-166, 1996.

Thanoo, et al., "Controlled release of oral drugs from cross-linked polyvinyl alcohol microspheres", J Pharm Pharmacol, vol. 45, No. 1, pp. 16-20, 1993.

Thanoo, B. C. et al., "Preparation and Properties of Barium Sulphate and Methyl Iothalamate Loaded Poly(vinyl Alcohol) Microspheres as Radiopaque Particulate Emboli," Journal of Applied Biomaterials, 2:67-72 (1991).

Thanoo, et al., "Tantalum loaded silicone micropsheres as particulate emboli", J Microencapsul, vol. 8, No. 1, pp. 95-101, 1991.

Thelen, V.M. et al., "Catheter Embolisation of Metastasising Renal Carcinomas Using Butyle-2-cyano-acrylate", Fortschr. Rontgenstr., vol. 124, No. 3, pp. 232-235, Mar. 1976 (English Abstract included).

The Fibroid Embolization Center of the New York United Hospital Medical Center, "Fibroid Facts," http://www.uhmc.com/fibro2.htm, 9 pages, (2007).

The Vanderbilt-Ingram Cancer Center, "Kidney Cancer," http://www.mc.Vanderbilt.Edu/cancer/cancerinfo/kidney.html, 1 page, 2001.

Tikkakoski, et al., "Preoperative embolization in the management of neck paragangliomas", Laryngoscope, vol. 107, pp. 821-826, 1997.

Toon, "Improving a Key Weapon Against Cancer," Research Horizons, pp. 11-12, Spring/Summer 2001.

Touho, et al., "Intravascular treatment of spinal arteriovenous malformations using a microcatheter—with special reference to serial xylocaine tests and intravascular pressure monitoring", Surgical Neurology, vol. 42, No. 2, pp. 148-156, 1994.

Tournade et al., "Miscellanea," Interventional Neuroradiology, 11(Suppl. 2):107-111 (Oct. 2005).

UCLA Radiological Sciences, "A summary of terms appearing in this text," http://www.radsci.ucla.edu:8000/aneurysm/terms.html, 1 page, (2007).

University Medical Center SUNY Stony Brook, Department of Urology, "Variococele and its treatment," http://www.hsc.sunysb.edu/urology/male_inf...variocoele_and_its_treatment.html, 8 pages, Last Updated on Mar. 12, 2001.

Vivas S et al., "Arterioportal fistula and hemobilia in a patient with hepatic transplant", Gastroenterol Hepatol, 21(2):88-9, http://www.doyma.es/copiani/revistas/gastro/abstr/abs_p080.html, Feb. 1998 (English Abstract included).

Vogel F, "Nonsurgical Management of Uterine Fibroids," http://www.holyname.org/brochure/fibroids.html, 5 pages, (2007).

Wakhloo, et al., "Extended preoperative polyvinyl alcohol microembolilzation of intracranial meningiomas: Assessment of two embolization techniques", American Journal of Neuroradiology, vol. 14, pp. 571-582, 1993.

Walker WJ, "Non Surgical Treatment of Fibroids in the UK by Uterine Artery Embolisation—An Alternative to Hysterectomy, Myomectomy and Myolysis," http://www.fibroids.co.uk/thepaper.html, 2 pages, 2002.

Walsh RM et al., "Role of Angiography and Embolization for Acute Massive Upper Gastronintestinal Hemorrhage," J. Gastrointest. Surg., 3:61-66 (1999).

Waltman, A.C. et al., "Technique for Left Gastric Artery Catheterization", Radiology, vol. 109, No. 3, pp. 732-734, Dec. 1973.

White, Jr., "Embolotherapy in Vascular Disease," American Journal of Roentgenology, 142:27-30 (Jan. 1984).

Widder, K.J. et al., "Selective Targeting of Magnetic Microspheres Containing Adriamycin: Total Remission in Yoshida Sarcoma-Bearing Rats", Proceedings of the 16th Annual Meeting of American Society of Clinical Oncology, May 26-27, 1980, San Diego, CA, p. 261.

Widder, K. et al., "Magnetic Microspheres: Synthesis of a Novel Parenteral Drug Carrier", Journal of Pharmaceutical Sciences, vol. 68, No. 1, pp. 79-82, Jan. 1979.

Wikholm G et al., "Embolization of Cerebral Arteriovenous Malformations: Part I—Technique, Morphology, and Complications", Neurosurgery, 39(3):448-459 (Sep. 1996).

Winters et al., "Periurethral injection of collagen in the treatment of intrinsic sphincteric deficiency in the female patient," The Urologic Clinics of North America, 22(3):673-678 (Aug. 1995).

Worthington-Kirsch RL, "Interventionalists offer management option for uterine fibroids," Diagnostic Imaging, 21(3):47-49, Mar. 1999, http://vvww.dimag.com/references/9903wortrefs.html.

Worthington-Kirsch, et al., "Uterine arterial embolization for the management of leiomyomas: Quality-of-life assessment and clinical response", Radiology, vol. 208, No. 3, 625-629, 1998.

Wright, K.C. et al., "Partial Splenic Embolization Using Polyvinyl Alcohol Foam, Dextran, Polystyrene, or Silicone," Radiology, 142:351-354, Feb. 1982.

Wu, A.M., "Engineered Antibodies for Breast Cancer Imaging and Therapy," http://www.cbcrp.org/research/PageGrant.asp?grant_id=111, 3 pages, 1996.

Yamada, T. et al., "Extended Intraarterial Cisplatin Infusion for Treatment of Gynecologic Cancer After Altercation of Intrapelvic Blood Flow and Implantation of a Vascular Access Device", Cardiovasc. Intervent. Radiol., vol. 19, pp. 139-145, 1996.

Yamashita, Y. et al., "Transcatheter Arterial Embolization of Obstetric and Gynaecological Bleeding: Efficacy and Clinical Outcome", British Journal of Radiology, vol. 67, pp. 530-534, Jun. 1994.

Yoon et al., "Surface Immobilization of Galactose onto Aliphatic Biodegradable Polymers for Hepatocyte Culture," Biotechnol. Bioeng., 78(1):1-10 (Apr. 5, 2002).

Yusi et al., "Submuscosal Injection of Polyvinyl Alcohol in Artificially Created Vesico-Ureteral Reflux: A Preliminary Report," Asian J. Surg., 18(2):122-127 (Apr. 1995).

Zisch et al., "Covalently conjugated VEGF-fibrin matrices for endothelialization," Journal of Controlled Release, 72:101-113 (2001).

Ziskin, M.C. et al., "Contrast Agents for Diagnostic Ultrasound", Investigative Radiology, vol. 7, No. 6, pp. 500-505, Nov.-Dec. 1972.

Zou, Ying-hua, et al. "Experimental Canine Hapatic Artery Embolization with Polyvinyl Alcohol Microspheres," Zhong Hua Fang-She Xue ZaZhi, 23(6):330-332 (1989).

Zou, Ying-hua, et al. "Experimental Canine Hapatic Artery Embolization with Polyvinyl Alcohol Microspheres," Translation, Zhong Hua Fang-She Xue ZaZhi, 23(6):330-332 (1989).

International Search Report and Written Opinion issued by the European Patent Office on Nov. 16, 2007, in the PCT application PCT/US2006/062241, filed Dec. 18, 2006.

* cited by examiner

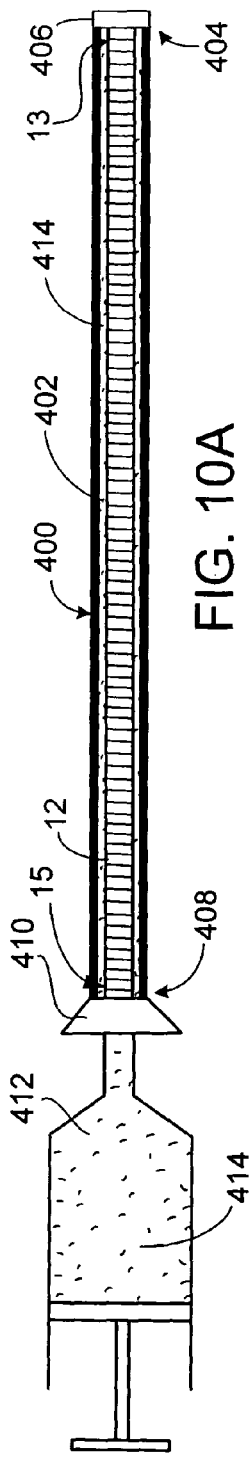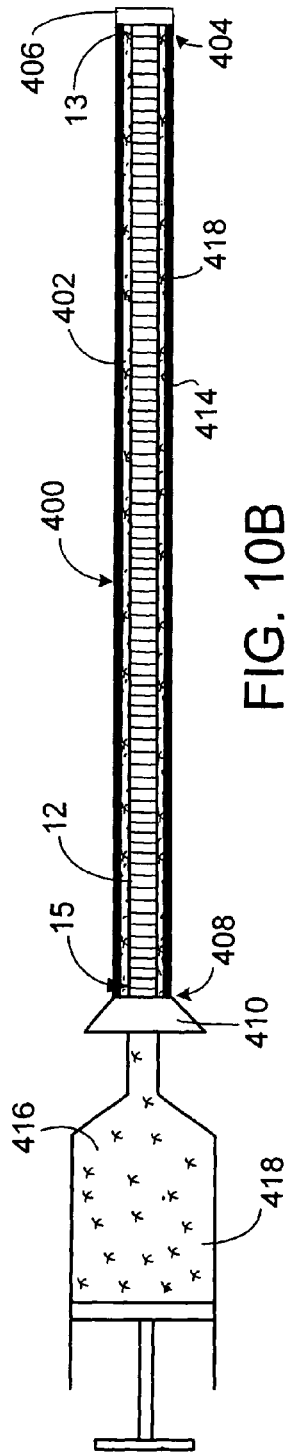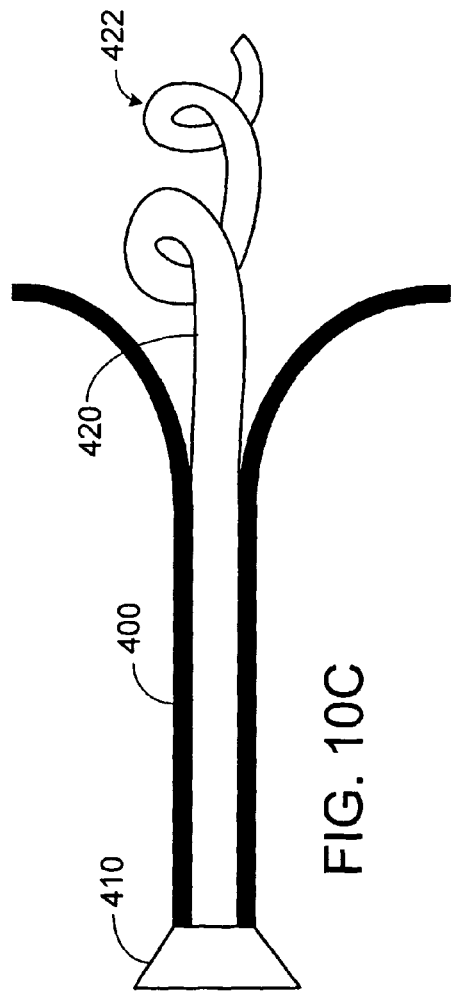

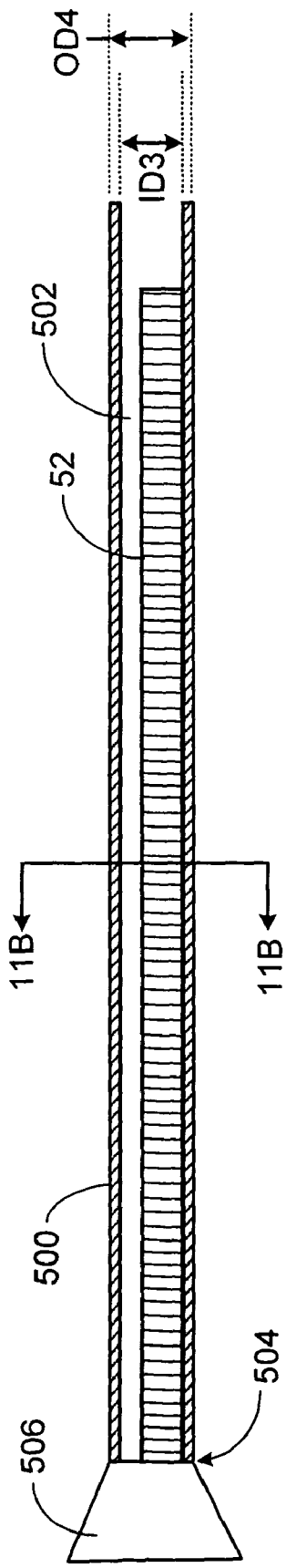
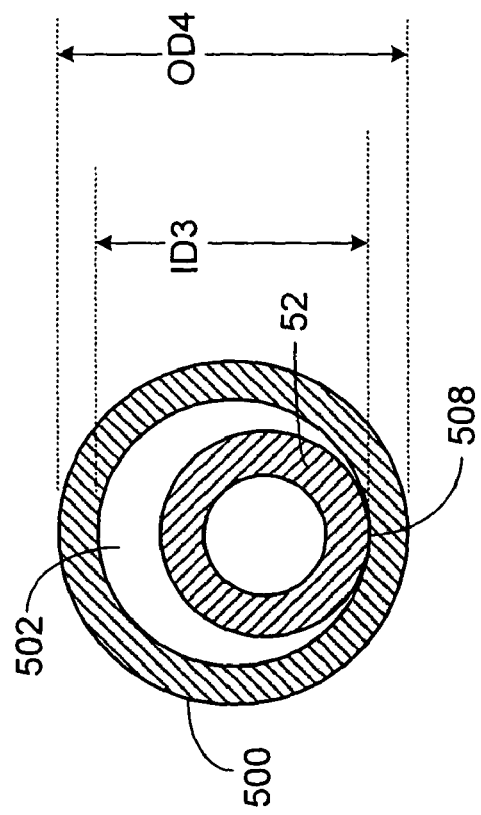

FORMING COILS

TECHNICAL FIELD

The invention relates to coils, such as embolic coils, as well as related methods, devices, and compositions.

BACKGROUND

Therapeutic vascular occlusions (embolizations) are used to prevent or treat pathological conditions in situ. Embolic coils can be used to occlude vessels in a variety of medical applications. Delivery of embolic coils (e.g., through a catheter) can depend on the size and/or shape of the coils.

SUMMARY

In one aspect, the invention features a method of coating a coil. The method includes injecting a material into a container containing the coil, and forming the material into a coating that is supported by the coil.

In another aspect, the invention features a method of coating a coil. The method includes contacting the coil with a composition including a first polymer and a gelling precursor, and forming the composition into a coating that is supported by the coil.

In an additional aspect, the invention features an article that is in the shape of a coil. The article includes a substrate and a porous material supported by the substrate.

In a further aspect, the invention features an article that is in the shape of a coil. The article includes a substrate and a material supported by the substrate. The material includes a first polymer and a gelling precursor.

In another aspect, the invention features an article that is in the shape of a coil. The article includes a substrate and a material supported by the substrate. The material includes at least two different polymers.

In an additional aspect, the invention features a method that includes administering at least one article to a subject. The article is in the shape of a coil and includes a substrate and a porous material supported by the substrate.

In a further aspect, the invention features a method that includes administering at least one article to a subject. The article is in the shape of a coil, and the article includes a substrate and a material supported by the substrate. The material includes a first polymer and a gelling precursor.

In another aspect, the invention features a method that includes administering at least one article to a subject. The article is in the shape of an embolic coil, and the article includes a substrate and a material supported by the substrate. The material includes at least two different polymers.

Embodiments can also include one or more of the following.

The coil can be an embolic coil (e.g., the article can be in the shape of an embolic coil).

The material can include a polymer. The polymer can be a polysaccharide (e.g., alginate) or polyvinyl alcohol. In certain embodiments, the material can include at least two different polymers. In some embodiments, the material can include a polymer (e.g., polyvinyl alcohol) and a gelling precursor. The gelling precursor can include a polymer (e.g., that is different from another polymer in the material). In certain embodiments, the gelling precursor can include a polysaccharide, such as alginate. In some embodiments, the material can include polyvinyl alcohol and alginate. In certain embodiments, the material can include a therapeutic agent. In some embodiments, the material can include a protein, such as collagen.

The method can include lyophilizing the material and/or contacting the material with starch and/or sodium chloride.

Forming the coating can include cross-linking the polymer and/or removing at least a portion of the gelling precursor. In some embodiments, forming the coating can include contacting the material with a gelling agent. The gelling agent can include calcium chloride. Contacting the material with a gelling agent can include delivering the gelling agent into the container and/or delivering the coil from the container into the gelling agent. Forming the coating can include contacting the material with a cross-linking agent. The cross-linking agent can include an aldehyde, an acid, and/or a salt (e.g., a salt including a multivalent cation, such as calcium chloride). In certain embodiments, contacting the material with a cross-linking agent can include delivering the cross-linking agent into the container and/or delivering the coil from the container into the cross-linking agent.

The coating can be in direct contact with an outer surface of the coil. In certain embodiments, the coating can be supported by only a portion of the coil. In some embodiments, the coating can be porous.

The article can include a therapeutic agent. In some embodiments, the method can include delivering the therapeutic agent from the article.

In some embodiments, the method can include contacting the material with a therapeutic agent (e.g., by delivering the therapeutic agent into the container).

The container can include a tubular member. In certain embodiments, the tubular member can have an inner diameter of at least 0.008 inch (e.g., at least 0.021 inch) and/or at most 0.038 inch (e.g., at most 0.021 inch). In some embodiments, the tubular member can have an outer diameter of at least 0.01 inch (e.g., at least 0.015 inch, at least 0.042 inch) and/or at most 0.06 inch (e.g., at most 0.042 inch, at most 0.015 inch). The tubular member can be cylindrical. In certain embodiments, the tubular member can have a non-circular cross-section (e.g., a polygonal cross-section). In some embodiments, the container can include an introducer sheath. In certain embodiments, the container can include a catheter that is configured to fit within a lumen of a subject.

The method can include removing the coil from the container (e.g., by cutting the container and/or by peeling the container away from the coil). In some embodiments, the container can include a bioerodible and/or bioabsorbable material. The method can include removing the coil from the container by eroding and/or absorbing the container.

In certain embodiments, removing the coil from the container can include contacting the container with an agent that is adapted to dissolve the container. In some embodiments, removing the coil from the container can include pushing and/or pulling the coil out of the container.

In certain embodiments, the coil can be contacted with a composition including a polymer and a gelling precursor by adding the composition into a container containing the coil.

In some embodiments, the composition can be in the form of a solution.

In certain embodiments, the porous material can include a first portion having one density of pores and a second portion having another density of pores that is different from the density of pores in the first portion. In some embodiments, the first portion of the porous material can be disposed between the substrate and the second portion of the porous material, and the density of pores in the second portion can be greater than the density of pores in the first portion. In certain embodiments, the porous material can include a first portion having one average pore size and a second portion having another average pore size that is different from the average pore size in the first portion. In some embodiments, the first portion of the porous material can be disposed between the wire and the second portion of the porous material, and the average pore size in the first portion can be greater than the average pore size in the second portion.

The porous material can include a polymer, such as polyvinyl alcohol. In some embodiments, the porous material can include a polysaccharide (e.g., alginate). In certain embodiments, the porous material can include at least two different polymers. In some embodiments, the porous material can include a therapeutic agent. The porous material can be in direct contact with an outer surface of the substrate. In certain embodiments, the porous material can form a coating on the substrate. The coating can have a thickness of at least about five microns (e.g., at least about 10 microns, at least about 50 microns, at least about 100 microns, at least about 250 microns) and/or at most about 500 microns (e.g., at most about 250 microns, at most about 100 microns, at most about 50 microns, at most about 10 microns).

The substrate can include a metal (e.g., platinum, gold, rhenium, palladium, rhodium, ruthenium, tungsten), a metal alloy (e.g., Nitinol, stainless steel, a platinum/tungsten alloy), and/or a polymer (e.g., a polyamino acid, a polynucleic acid, a polysaccharide, a polyhydroxyalkanoate, a polyanhydride). In certain embodiments, the substrate can include at least one of the following materials: a polyurethane, a polyether, a polyimide, an acrylate, an epoxy adhesive material, an olefin, a polydimethyl siloxane-based polymer, Rayon, cellulose, a cellulose derivative, a natural rubber, a polyester, hydroxybutyrate, polyhydroxyvalerate, a polyether ester, an anhydride, or a mixture or copolymer of at least two of these materials.

The substrate can be in the form of a wire. In some embodiments, the wire can have a diameter of from 0.0005 inch to 0.005 inch.

In certain embodiments, the method can include using a catheter to administer the article to the subject. In some embodiments, the method can include using a device to administer the article to the subject. The device can have an internal opening and/or can be configured to fit within a lumen of a subject. In certain embodiments, the article can be disposed within the internal opening of the device. The method can include using a pusher wire to deliver the article from the device. In some embodiments, the article can be attached to the pusher wire, and the method can include detaching (e.g., mechanically, chemically, electrolytically, thermally, hydraulically) the article from the pusher wire to deliver the article from the device.

The method can include treating at least one of the following: an aneurysm, an arteriovenous formation, a traumatic fistula, a tumor. In some embodiments, the method can include embolizing a lumen of a subject.

Embodiments can include one or more of the following advantages.

In some embodiments, a coil that includes a coating can exhibit relatively good occlusive properties when delivered to a target site within a subject. This can, for example, allow the coil to be used to occlude a vessel (e.g., to embolize a tumor), treat an aneurysm, treat an arteriovenous malformation, and/or treat a traumatic fistula. In certain embodiments, a coil that includes a coating can be used to elicit thrombosis at a target site, which can enhance the occlusion of the target site.

In some embodiments, a coil that includes a coating can be used to deliver one or more therapeutic agents to a target site. In certain embodiments, the coil can be used to deliver a metered dose of a therapeutic agent to a target site over a period of time. In some embodiments, the release of a therapeutic agent from the coil can be delayed until the coil has reached a target site. For example, the coating can be a bioerodible coating that erodes during delivery, such that when the coil reaches the target site, the coil can begin to release the therapeutic agent.

In certain embodiments, a coil that includes a coating can be used to deliver multiple therapeutic agents, either to the same target site, or to different target sites. For example, the coil can deliver one type of therapeutic agent (e.g., an anti-inflammatory agent, an anti-thrombotic agent) as the coil is being delivered to a target site, and another type of therapeutic agent (e.g., a growth factor) once the coil has reached the target site.

In some embodiments, a coil that includes a coating can be used both to occlude a target site and to deliver one or more therapeutic agents to the target site.

In certain embodiments, a coil that includes a coating can experience enhanced protection of its coil body. As an example, in some embodiments, the coating can protect the coil body as the coil is delivered into a subject from a delivery device. As another example, in certain embodiments, the coating can protect the coil body during storage of the coil.

In some embodiments, a coil that includes a coating can exhibit relatively good deliverability. For example, in certain embodiments, the coil can experience relatively little friction with the walls of a delivery device if the coil contacts the walls of the delivery device during delivery. The coating can enhance the lubricity of the coil, making it relatively easy to deliver the coil from a delivery device.

In some embodiments, a coil that includes a coating can have a relatively smooth outer surface. In certain embodiments, the relatively smooth outer surface can enhance the deliverability of the coil from a delivery device (e.g., by limiting the likelihood that the coil will become caught on the delivery device during delivery).

Other aspects, features, and advantages are in the description, drawings, and claims.

DESCRIPTION OF DRAWINGS

FIGS. 10A-10E illustrate an embodiment of a process for forming an embolic coil.

FIGS. 11A-11D illustrate an embodiment of a process for forming an embolic coil.

DETAILED DESCRIPTION

Figure 1A:
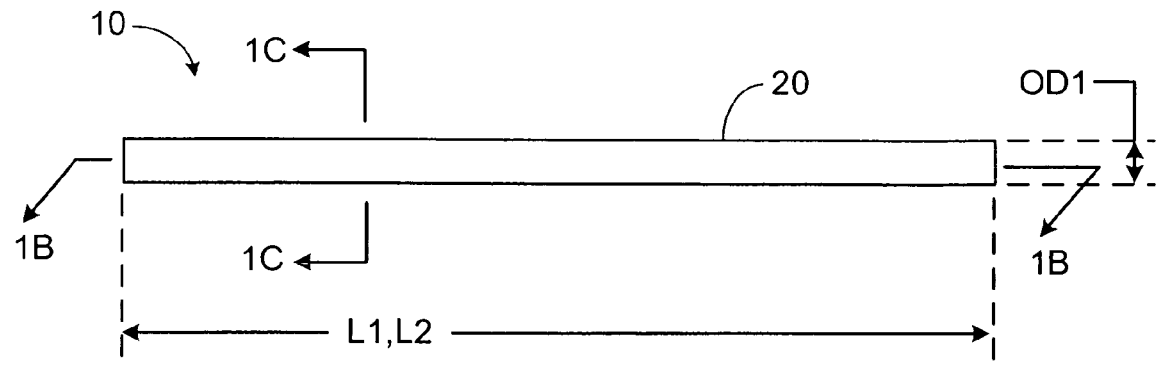
FIG. 1A is a side view of an embodiment of an embolic coil.
Figure 1B:
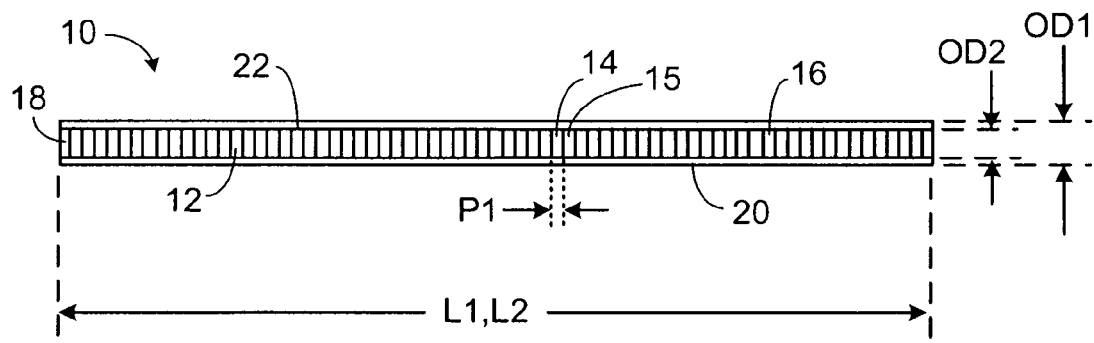
FIG. 1B is a cross-sectional view of the embolic coil of FIG. 1A, taken along line 1B-1B.
Figure 1C:
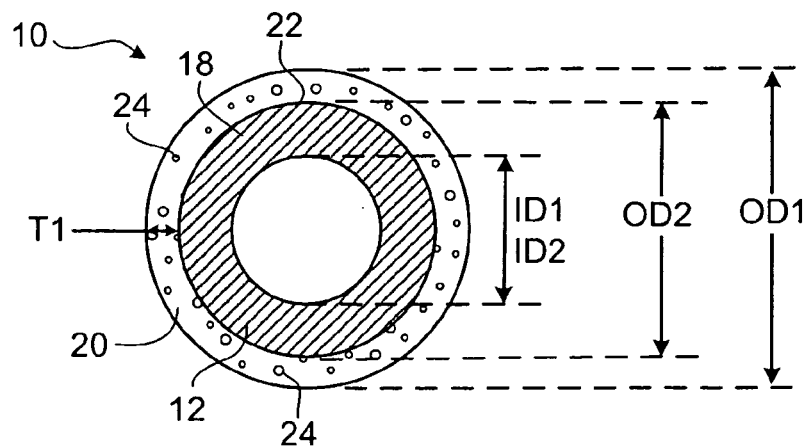
FIG. 1C is a cross-sectional view of the embolic coil of FIG. 1A, taken along line 1C-1C.

FIGS. 1A-1C show the primary shape of an embolic coil 10 that includes a coil body 12 formed of windings (e.g., windings 14, 15, and 16) of a wire 18 (e.g., a platinum wire). Embolic coil 10 also includes a coating 20 (e.g., a polyvinyl alcohol coating) disposed on the exterior surface 22 of coil body 12. Coating 20 includes pores 24. Embolic coil 10 can be used, for example, in an embolization procedure, and/or can be used to deliver one or more therapeutic agents to a target site.

As shown in FIG. 1C, coating 20 has a thickness T1. In general, thickness T1 can be selected based on the application of embolic coil 10. As an example, in some embodiments in which coating 20 contains a therapeutic agent and embolic coil 10 is used to deliver the therapeutic agent to a target site, thickness T1 can be selected to effect a specific delivery rate of the therapeutic agent to the target site. As another example, in certain embodiments in which coating 20 is an erodible coating that is used to protect exterior surface 22 of embolic coil 10 during delivery of embolic coil 10 to a target site, thickness T1 can be selected so that the coating is present during delivery but has eroded once embolic coil 10 has reached the target site. In certain embodiments, thickness T1 can be selected based on multiple considerations (e.g., delivery of a therapeutic agent and protection of surface 22). In some embodiments, thickness T1 can be at least about five microns (e.g., at least about 10 microns, at least about 25 microns, at least about 50 microns, at least about 75 microns, at least about 100 microns, at least about 200 microns, at least about 250 microns, at least about 300 microns, at least about 400 microns) and/or at most about 500 microns (e.g., at most about 400 microns, at most about 300 microns, at most about 250 microns, at most about 200 microns, at most about 100 microns, at most about 75 microns, at most about 50 microns, at most about 25 microns, at most about 10 microns).

Embolic coil 10 in its primary shape has a length L1, an inner diameter ID1, and an outer diameter OD1. Generally, these dimensions can be selected as desired. In some embodiments, length L1 can be at least about one centimeter (e.g., at least about five centimeters, at least about 10 centimeters, at least about 20 centimeters, at least about 30 centimeters, at least about 40 centimeters, at least about 50 centimeters), and/or at most about 60 centimeters (e.g., at most about 50 centimeters, at most about 40 centimeters, at most about 30 centimeters, at most about 20 centimeters, at most about 10 centimeters, at most about five centimeters). In certain embodiments, inner diameter ID1 can be at least 0.001 inch (e.g., at least 0.002 inch, at least 0.006 inch, at least 0.01 inch, at least 0.015 inch, at least 0.02 inch, at least 0.025 inch, at least 0.03 inch) and/or at most 0.036 inch (e.g., at most 0.03 inch, at most 0.025 inch, at most 0.02 inch, at most 0.015 inch, at most 0.01 inch, at most 0.006 inch, at most 0.002 inch). In some embodiments, outer diameter OD1 can be at least 0.003 inch (e.g., at least 0.008 inch, at least 0.015 inch, at least 0.021 inch, at least 0.03 inch) and/or at most 0.038 inch (e.g., at most 0.03 inch, at most 0.021 inch, at most 0.015 inch, at most 0.008 inch). For example, in certain embodiments, outer diameter OD1 can be 0.010 inch or 0.015 inch.

In certain embodiments, outer diameter OD1 can be selected based on the intended use of embolic coil 10. As an example, in certain embodiments in which embolic coil 10 can be used to treat intracranial aneurysms, outer diameter OD1 can be relatively small (e.g., at most 0.016 inch). As another example, in some embodiments in which embolic coil 10 can be used to treat arteriovenous malformations, outer diameter OD1 can be relatively large (e.g., at least 0.021 inch).

In some embodiments, outer diameter OD1 can be selected based on the size of a delivery system that will be used to deliver the coil (e.g., a catheter having an inner diameter of 0.010 inch, 0.018 inch, or 0.035 inch).

When embolic coil 10 is in its primary shape, coil body 12 has a length L2 that is equal to length L1 of embolic coil 10, an inner diameter ID2 that is equal to inner diameter ID1 of embolic coil 10, and an outer diameter OD2. In some embodiments, outer diameter OD2 can be at least 0.003 inch (e.g., at least 0.008 inch, at least 0.015 inch, at least 0.021 inch, at least 0.03 inch) and/or at most 0.038 inch (e.g., at most 0.03 inch, at most 0.021 inch, at most 0.015 inch, at most 0.008 inch).

The pitch of a coil body, such as coil body 12, is the sum of the thickness of one winding of the coil body (e.g., winding 14) and the amount of space between that winding and a consecutive winding of the coil body (e.g., winding 15). FIG.

1B shows the pitch P1 of coil body 12. Because the windings of coil body 12 are flush with each other, pitch P1 is equal to the thickness of a winding of coil body 12. In some embodiments, pitch P1 can be at most 0.01 inch (e.g., at most 0.005 inch), and/or at least 0.0005 inch (e.g., at least 0.005 inch). While the windings of coil body 12 are shown as being flush with each other, in certain embodiments, a coil can include windings that are not flush with each other and that have space between them.

Coating 20 can include (e.g., can be formed of) one or more materials.

In some embodiments, coating 20 can include one or more polymers (e.g., at least two polymers, at least three polymers, at least four polymers, at least five polymers). Examples of polymers include polyvinyl alcohols (PVA), polyacrylic acids, polyamino acids, polyolefins, polyanhydrides, polymethacrylic acids, poly vinyl sulfonates, carboxymethyl celluloses, hydroxyethyl celluloses, substituted celluloses, polyacrylamides, polyethylene glycols, polyamides (e.g., nylon), polyureas, polyurethanes, polyesters, polyethers, polystyrenes, polysaccharides (e.g., alginate, agarose), polylactic acids, polyethylenes, polymethylmethacrylates, polyethylacrylate, polycaprolactones, polyglycolic acids, poly(lactic-co-glycolic) acids (e.g., poly(d-lactic-co-glycolic) acids), and copolymers or mixtures thereof. An example of a copolymer is a polyglycolic acid/lactide copolymer. In certain embodiments, the polymer can be a highly water insoluble, high molecular weight polymer. An example of such a polymer is a high molecular weight polyvinyl alcohol (PVA) that has been acetalized. The polymer can be substantially pure intrachain 1,3-acetalized PVA and substantially free of animal derived residue such as collagen.

In some embodiments, coating 20 can include one or more gelling precursors. Examples of gelling precursors include alginates, alginate salts (e.g. sodium alginate), xanthan gums, natural gum, agar, agarose, chitosan, carrageenan, fucoidan, furcellaran, laminaran, hypnea, eucheuma, gum arabic, gum ghatti, gum karaya, gum tragacanth, hyaluronic acid, locust beam gum, arabinogalactan, pectin, amylopectin, other water soluble polysaccharides and other ionically cross-linkable polymers. A particular gelling precursor is sodium alginate. An example of sodium alginate is high guluronic acid, stem-derived alginate (e.g., about 50 percent or more, about 60 percent or more guluronic acid) with a low viscosity (e.g., from about 20 centipoise to about 80 centipoise at 20° C.), which can produce a high tensile, robust gel.

In some embodiments, coating 20 can include one or more bioerodible and/or bioabsorbable materials. In certain embodiments, coating 20 can be formed entirely of bioerodible and/or bioabsorbable materials. This can, for example, allow coating 20 to erode and/or to be absorbed during and/or after delivery of embolic coil 10 to a target site. Examples of bioerodible and/or bioabsorbable materials include polysaccharides (e.g., alginate); polysaccharide derivatives; inorganic, ionic salts; water soluble polymers (e.g., polyvinyl alcohol, such as polyvinyl alcohol that has not been cross-linked); biodegradable poly DL-lactide-poly ethylene glycol (PELA); hydrogels (e.g., polyacrylic acid, hyaluronic acid, gelatin such as gelatin foam, carboxymethyl cellulose); polyethylene glycol (PEG); chitosan; polyesters (e.g., polycaprolactones); poly(lactic-co-glycolic) acid (e.g., a poly(d-lactic-co-glycolic) acid); polyamino acids; polynucleic acids; polyhydroxyalkanoates; polyanhydrides; and combinations thereof. In some embodiments, coating 20 can include sodium alginate.

In certain embodiments, coating 20 can include one or more proteins. Examples of proteins include collagen, enzymes, and growth factors.

In some embodiments, coating 20 can include one or more gelled materials, and/or can be in a gel form. For example, coating 20 can be formed of a gelling precursor (e.g., alginate) that has been gelled by being contacted with a gelling agent (e.g., calcium chloride).

In certain embodiments, coating 20 can include one or more radiopaque materials. As used herein, a radiopaque material refers to a material having a density of about ten grams per cubic centimeter or greater (e.g., about 25 grams per cubic centimeter or greater, about 50 grams per cubic centimeter or greater). In some embodiments in which coating 20 includes one or more radiopaque materials, embolic coil 10 can exhibit enhanced visibility under X-ray fluoroscopy, such as when embolic coil 10 is in a subject. In certain embodiments, X-ray fluoroscopy can be performed without the use of a radiopaque contrast agent. Radiopaque materials are described, for example, in Rioux et al., U.S. Patent Application Publication No. U.S. 2004/0101564, published on May 27, 2004, which is incorporated herein by reference.

In certain embodiments, coating 20 can include one or more MRI-visible materials. As used herein, an MRI-visible material refers to a material that has a magnetic susceptibility of at most about one or less (e.g., at most about 0.5 or less; at most about zero or less) when measured at 25° C. In some embodiments in which coating 20 includes one or more MRI-visible materials, embolic coil 10 can exhibit enhanced visibility under MRI, such as when embolic coil 10 is in a subject (see discussion below). In certain embodiments, MRI can be performed without the use of an MRI contrast agent. MRI-visible materials are described, for example, in Rioux et al., U.S. Patent Application Publication No. U.S. 2004/0101564, published on May 27, 2004, which is incorporated herein by reference.

In certain embodiments, coating 20 can include one or more ferromagnetic materials. As used herein, a ferromagnetic material refers to a material that has a magnetic susceptibility of at least about 0.075 or more (e.g., at least about 0.1 or more; at least about 0.2 or more; at least about 0.3 or more; at least about 0.4 or more; at least about 0.5 or more; at least about one or more; at least about ten or more; at least about 100 or more; at least about 1,000 or more; at least about 10,000 or more) when measured at 25° C. In some embodiments in which coating 20 includes one or more ferromagnetic materials, a magnetic source can be used to move or direct embolic coil 10 to a treatment site. The magnetic source can be external to the subject's body, or can be used internally. In certain embodiments, both an external magnetic source and an internal magnetic source can be used to move embolic coil 10. An example of an internal magnetic source is a magnetic catheter. Magnetic catheters are described, for example, in Freyman, U.S. Patent Application Publication No. U.S. 2003/0187320 A1, published on Oct. 2, 2003, which is incorporated herein by reference. An example of an external magnetic source is a magnetic wand. Ferromagnetic materials are described, for example, in Rioux et al., U.S. Patent Application Publication No. U.S. 2004/0101564, published on May 27, 2004, which is incorporated herein by reference.

In some embodiments, coating 20 can include one or more materials that are neither bioerodible nor bioabsorbable.

In certain embodiments, coating 20 can include two or more of any of the above materials. For example, in some embodiments, coating 20 can include one or more polymers and one or more gelling precursors.

Figure 2A:
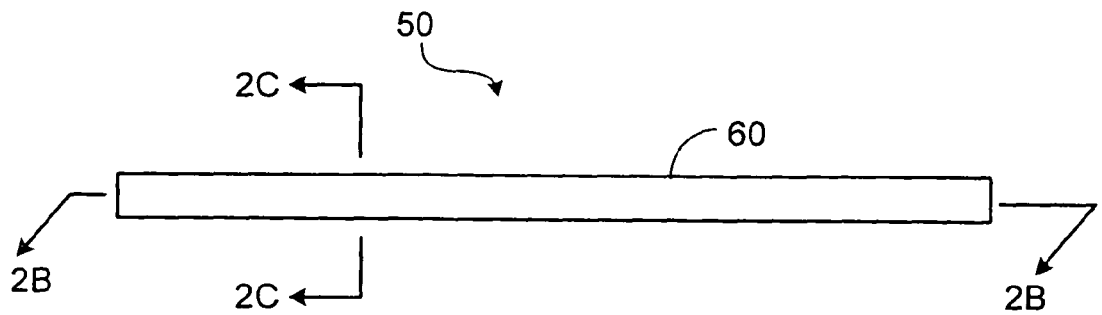
FIG. 2A is a side view of an embodiment of an embolic coil.
Figure 2B:
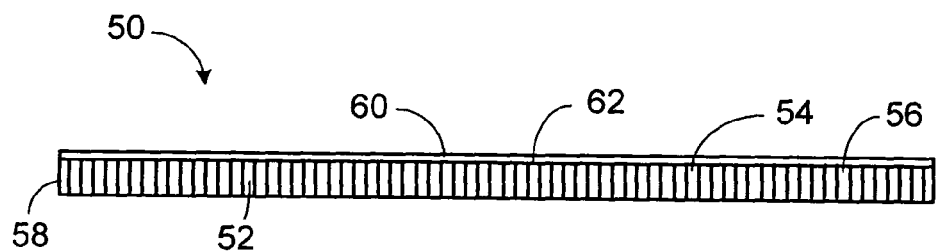
FIG. 2B is a cross-sectional view of the embolic coil of FIG. 2A, taken along line 2B-2B.
Figure 2C:
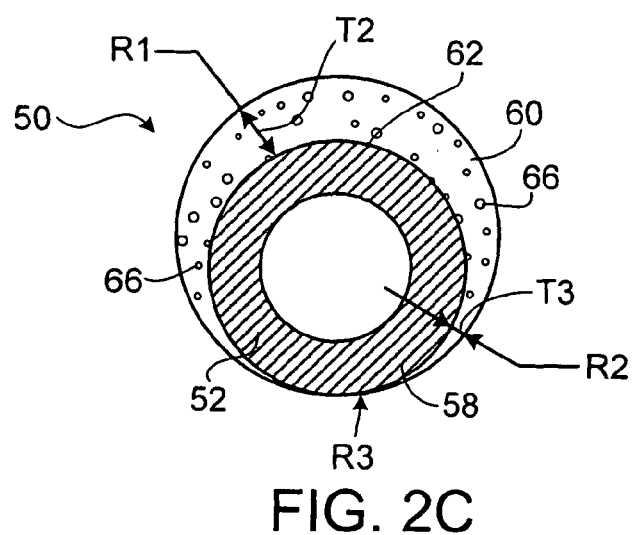
FIG. 2C is a cross-sectional view of the embolic coil of FIG. 2A, taken along line 2C-2C.

While FIG. 1C shows that embolic coil 10 can have a coating 20 with a relatively uniform thickness T1 around coil body 12, in some embodiments, an embolic coil can have a coating with a non-uniform thickness. For example, FIGS. 2A-2C show the primary shape of an embolic coil 50 including a coil body 52 formed of windings (e.g., windings 54 and 56) of a wire 58, and a coating 60 disposed on the exterior surface 62 of coil body 52. Coating 60 includes pores 66. The thickness of coating 60 on coil body 52 varies in different regions of embolic coil 50. For example, as shown in FIG. 2C, in one region R1 of embolic coil 50, coating 60 has a thickness T2. In some embodiments, thickness T2 can be at least about five microns (e.g., at least about 10 microns, at least about 50 microns, at least about 100 microns, at least about 250 microns, at least about 500 microns, at least about 750 microns) and/or at most about 1000 microns (e.g., at most about 750 microns, at most about 500 microns, at most about 250 microns, at most about 100 microns, at most about 50 microns, at most about 10 microns). In another region R2 of embolic coil 50, coating 60 has a thickness T3. In certain embodiments, thickness T3 can be at least about one micron (e.g., at least about 10 microns, at least about 25 microns, at least about 50 microns, at least about 75 microns) and/or at most about 100 microns (e.g., at most about 75 microns, at most about 50 microns, at most about 25 microns, at most about 10 microns). In certain regions of embolic coil 50, there may be no coating on coil body 52. For example, in region R3 of embolic coil 50, there is no coating on coil body 52.

Typically, a wire (e.g., wire 18, wire 58) that is used to form a coil body can include (e.g., can be formed of) one or more materials that are capable of being shaped into a coil form. For example, a wire can include one or more materials that have sufficient flexibility and/or malleability to be shaped into a coil form. In some embodiments, a wire can include one or more metals or metal alloys, such as platinum, a platinum alloy (e.g., platinum-tungsten alloy), stainless steel, Nitinol, and/or Elgiloy® alloy (from Elgiloy Specialty Materials).

In certain embodiments, a wire can include one or more polymers. The polymers can include synthetic polymers, natural polymers, cross-linked polymers, non-cross-linked polymers, thermosetting polymers, and/or thermoplastic polymers. Examples of polymers include polyolefins; polyurethanes; block copolymers (e.g., block copolymers with segments including esters, ethers and/or carbonates); polyethers; polyimides; acrylates (e.g., cyanoacrylates); epoxy adhesive materials (e.g., one-part epoxy-amine materials, two-part epoxy-amine materials); polymers and/or copolymers of ethylene, propylene, butadiene, styrene, and/or thermoplastic olefin elastomers; polydimethyl siloxane-based polymers; Rayon; cellulose; cellulose derivatives (e.g., nitrocellulose); natural rubbers; polyesters (e.g., polyethylene terephthalate); polylactides; polyglycolides; polycaprolactones; copolymers of lactides, glycolides, and/or caprolactones; polyhydroxybutyrate, polyhydroxyvalerate, and copolymers of hydroxybutyrate and hydroxyvalerate; polyether esters (e.g., polydioxanone); polyanhydrides, such as polymers and copolymers of sebacic acid, hexadecandioic acid and other diacids; orthoesters; polyamino acids; polynucleic acids; polysaccharides; and polyhydroxyalkanoates. In some embodiments, a wire can include one or more mixtures and/or copolymers (e.g., block copolymers, random copolymers) of these materials.

In some embodiments, a wire can include one or more shape-memory materials. Examples of shape-memory materials include Nitinol and shape-memory polymers (e.g., Veriflex™ shape-memory polymers, available from CRG Industries (Dayton, Ohio)).

In certain embodiments, a wire can include (e.g., encapsulate) one or more radiopaque materials. Radiopaque materials are described, for example, in Rioux et al., U.S. Patent Application Publication No. U.S. 2004/0101564 A1, published on May 27, 2004, which is incorporated herein by reference.

In some embodiments, a wire that is used to form a coil body can have a diameter of at least 0.0005 inch (e.g., at least 0.001 inch, at least 0.002 inch, at least 0.003 inch, at least 0.004 inch) and/or at most 0.005 inch (e.g., at most 0.004 inch, at most 0.003 inch, at most 0.002 inch, at most 0.001 inch).

Embolic coils can generally be used in a number of different applications, such as neurological applications and/or peripheral applications. In some embodiments, embolic coils can be used to embolize a lumen of a subject (e.g., to occlude a vessel), and/or to treat an aneurysm (e.g., an intercranial aneurysm), an arteriovenous malformation (AVM), and/or a traumatic fistula. In certain embodiments, embolic coils can be used to embolize a tumor (e.g., a liver tumor). In some embodiments, embolic coils can be used in transarterial chemoembolization (TACE).

Figure 3A:
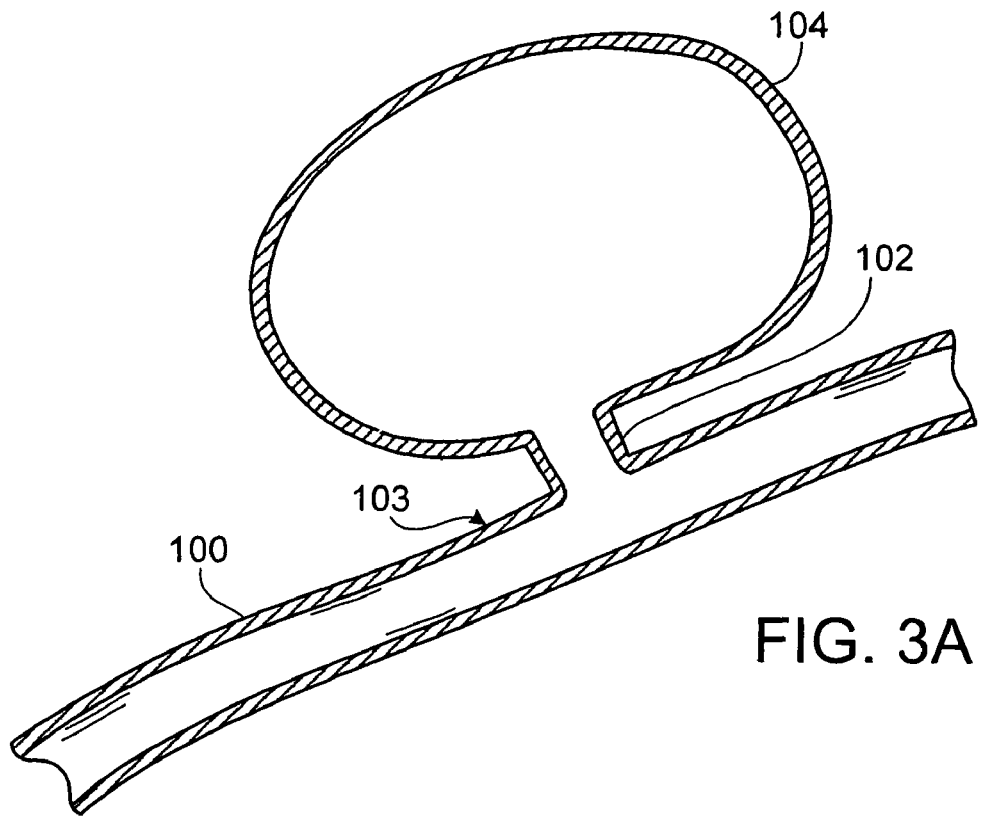
FIGS. 3A-3E illustrate the delivery of an embodiment of an embolic coil to the site of an aneurysm.

FIGS. 3A-3E show the use of embolic coil 10 to fill and occlude an aneurysmal sac 104 of a subject. As shown in FIG. 3A, aneurysmal sac 104 is formed in a wall 103 of a vessel 100, and is connected to vessel 100 by a neck 102.

Figure 3B:
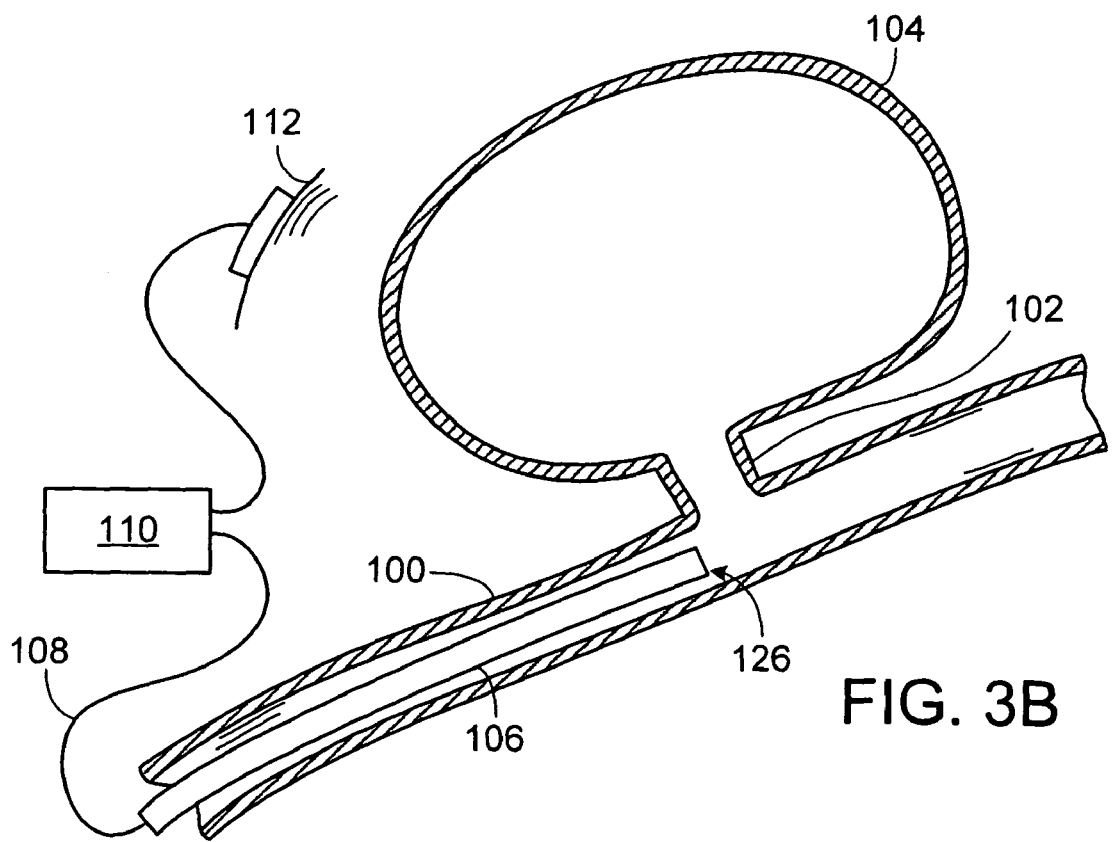
Figure 3C:
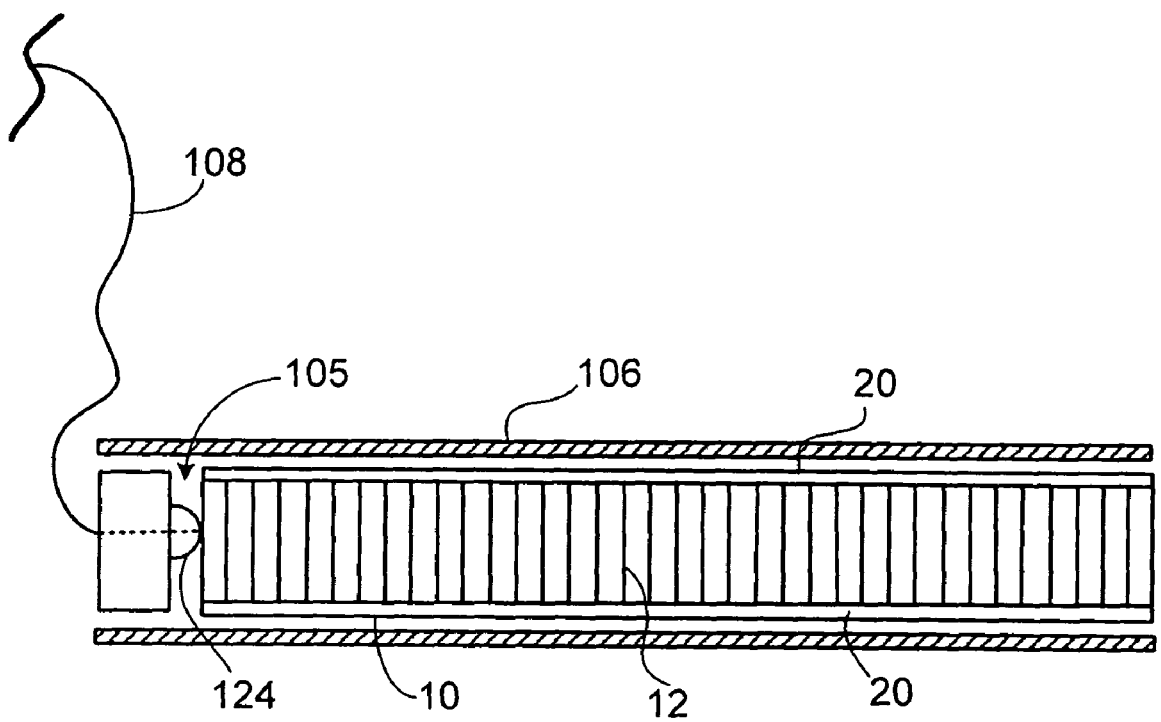

As shown in FIG. 3B, a catheter 106 containing embolic coil 10 is delivered into vessel 100. FIG. 3C shows a cross-sectional view of catheter 106 containing embolic coil 10. Embolic coil 10 is disposed within a lumen 105 of catheter 106, and is in its primary shape. In some embodiments, embolic coil 10 can be disposed within a pharmaceutically acceptable carrier (e.g., a saline solution, a contrast agent, a heparin solution, heparinized saline) while embolic coil 10 is within lumen 105 of catheter 106. Catheter 106 includes a core wire 108 connected to a power supply 110. Power supply 110 has a negative pole 112 that can be placed in electrical contact with the skin of the subject.

Figure 3D:
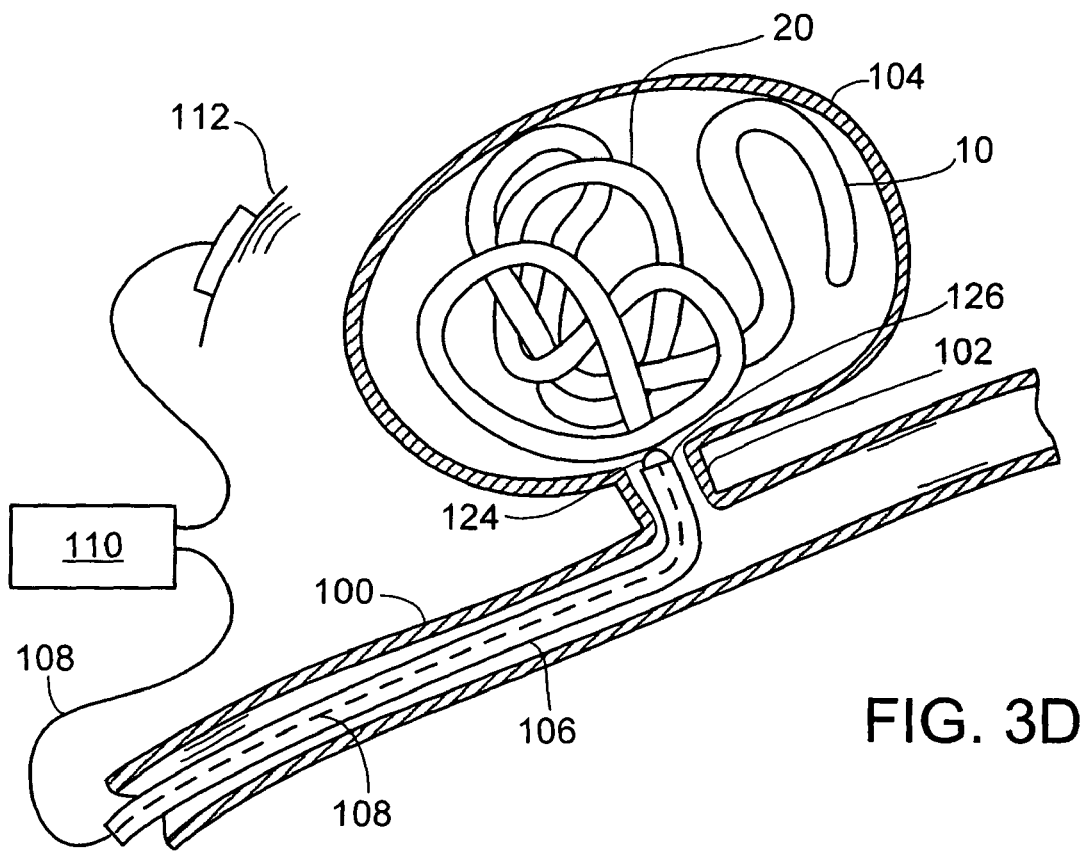
Figure 3E:
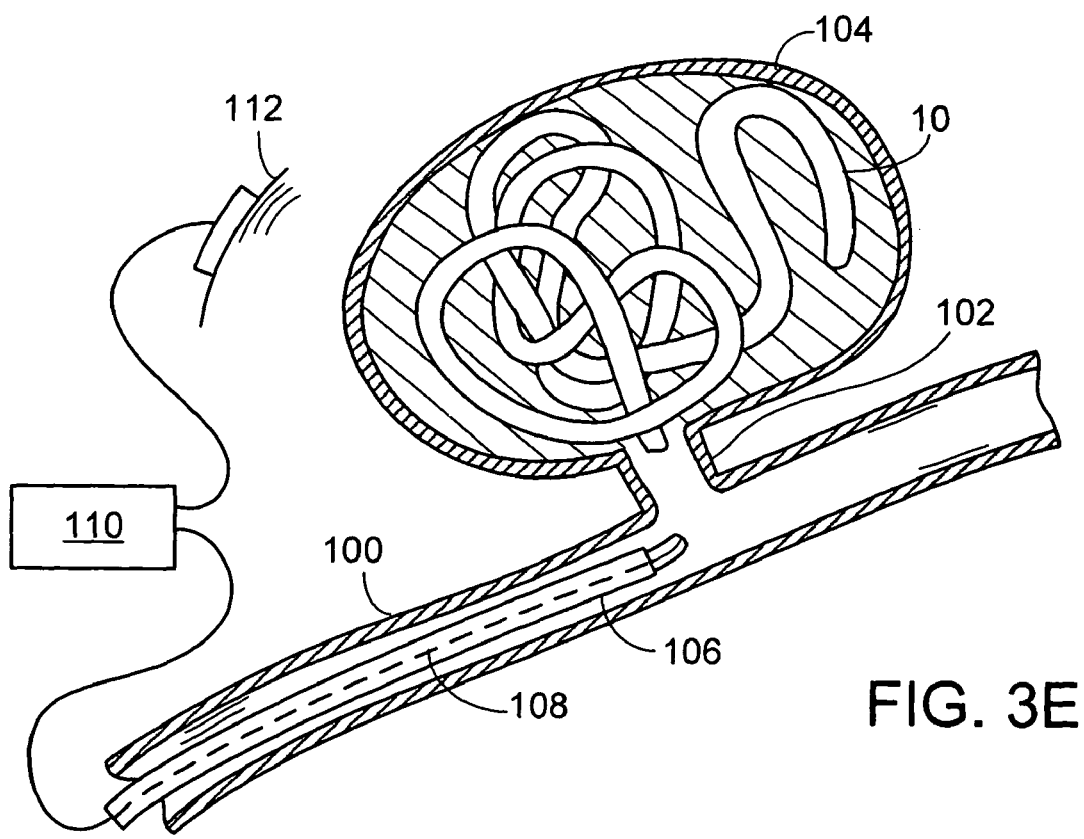

As shown in FIG. 3D, catheter 106 is used to deliver embolic coil 10 into aneurysmal sac 104, at least until a sacrificial link 124 between coil 10 and core wire 108 is exposed beyond the distal tip 126 of catheter 106. As shown in FIG. 3E, when an electrical current generated by power supply 110 flows through core wire 108, the electrical current causes sacrificial link 124 to disintegrate, thereby electrolytically detaching embolic coil 10 from core wire 108.

Embolic coil 10 fills aneurysmal sac 104. By filling aneurysmal sac 104, embolic coil 10 helps to occlude aneurysmal sac 104. In some embodiments, coating 20 of embolic coil 10 can accelerate the occlusion of aneurysmal sac 104 (e.g., by enhancing thrombosis within aneurysmal sac 104). An accelerated embolization procedure can benefit the subject by, for example, reducing exposure time to fluoroscopy. Embolic coils and coil delivery are described, for example, in Gia et al., U.S. Pat. No. 6,589,230, and Elliott et al., U.S. patent application Ser. No. 11/000,741, filed on Dec. 1, 2004, and entitled "Embolic Coils", both of which are incorporated herein by reference.

In general, an embolic coil such as embolic coil 10 has a primary shape and a secondary shape. Embolic coil 10 exhibits only its primary shape when embolic coil 10 is extended within lumen 105 of catheter 106 (as shown in FIG. 3C). As embolic coil 10 exits catheter 106, however, embolic coil 10 further assumes its secondary shape, which allows embolic coil 10 to fill aneurysmal sac 104. Typically, the primary shape of embolic coil 10 can be selected for deliverability, and the secondary shape of embolic coil 10 can be selected for application (e.g., embolization of an aneurysm).

Figure 4:
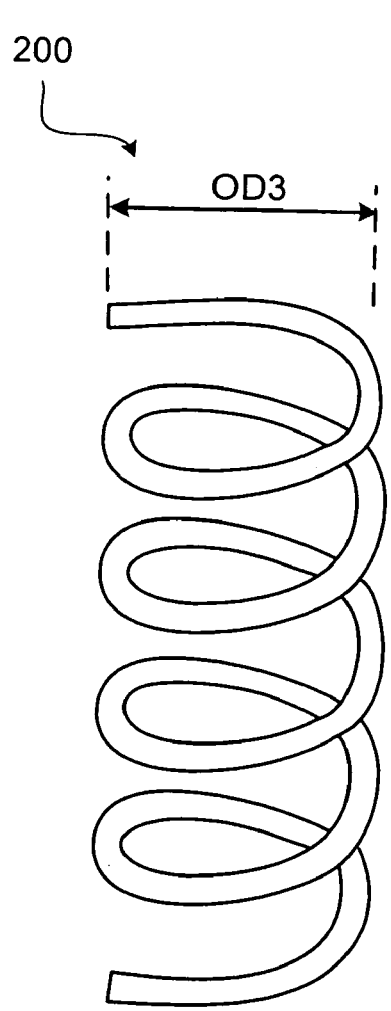
FIG. 4 is a perspective view of an embodiment of an embolic coil.
Figure 5:
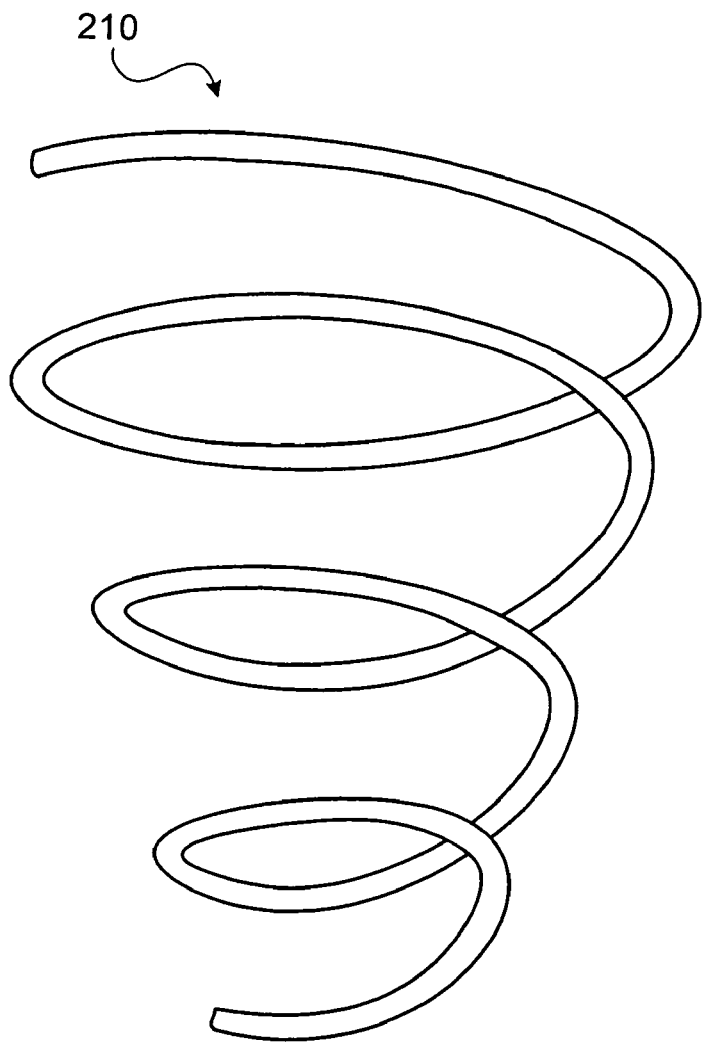
FIG. 5 is a perspective view of an embodiment of an embolic coil.
Figure 6:
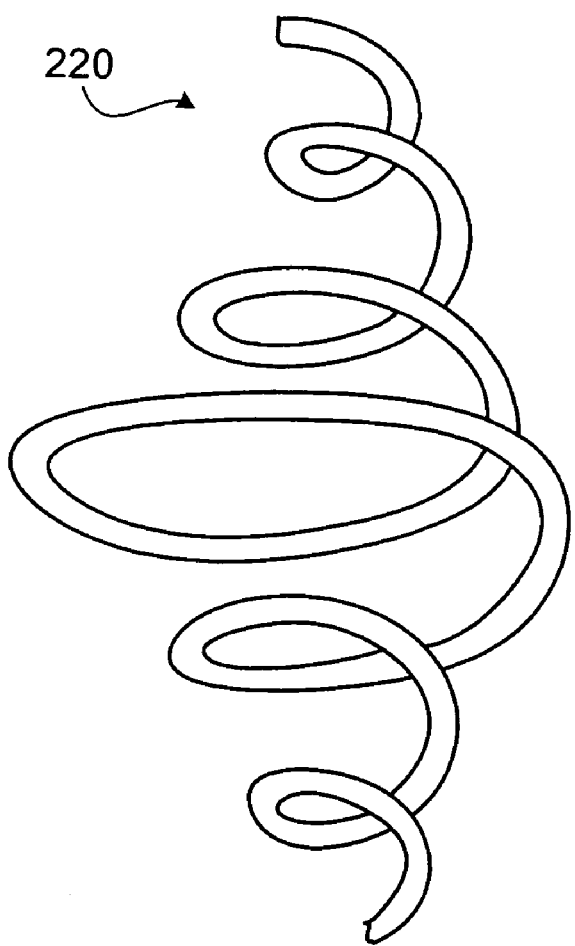
FIG. 6 is a perspective view of an embodiment of an embolic coil.
Figure 7:
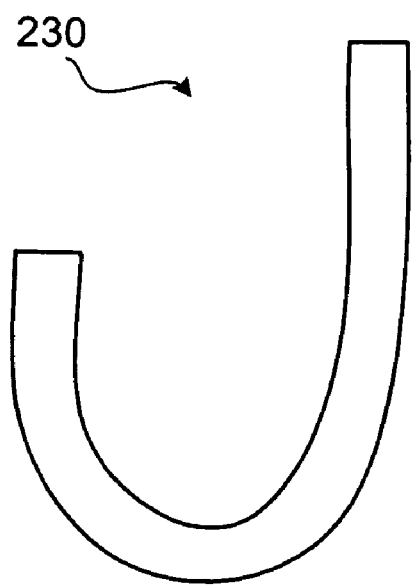
FIG. 7 is a perspective view of an embodiment of an embolic coil.

As FIGS. 4-7 illustrate, an embolic coil can have any of a number of different secondary shapes, which can depend on the particular application for the embolic coil. For example, FIG. 4 shows a coated embolic coil 200 having a helix secondary shape. As shown in FIG. 4, in its secondary shape, embolic coil 200 has an outer diameter OD3. In some embodiments, outer diameter OD3 can be about six millimeters. An embolic coil with a helix secondary shape can be used, for example, to provide a supportive framework along a vessel wall. Alternatively or additionally, an embolic coil with a helix secondary shape can be used to hold other embolic coils that are subsequently delivered to the target site. FIG. 5 shows a coated embolic coil 210 having a vortex secondary shape. An embolic coil with a vortex secondary shape can be used, for example, to close the center of a target site (e.g., a vessel, an aneurysm) that is to be occluded, and/or to occlude a target site in conjunction with an embolic coil such as embolic coil 200 (FIG. 4). As shown in FIG. 6, a coated embolic coil 220 has a diamond secondary shape. Like an embolic coil with a vortex secondary shape, an embolic coil with a diamond secondary shape can be used, for example, to close the center of a target site (e.g., a vessel, an aneurysm) that is to be occluded, and/or to occlude a target site in conjunction with an embolic coil such as embolic coil 200 (FIG. 4). FIG. 7 shows a coated embolic coil 230 having a secondary shape in the form of a J. An embolic coil having a secondary shape in the form of a J can be used, for example, to fill remaining space in an aneurysm that was not filled by other coils. In some embodiments, an operator (e.g., a physician) can hook the curved portion of embolic coil 230 into a coil or coil mass that has already been deployed at a target site, and then shape the straighter portion of embolic coil 230 to fill the target site.

Figure 8A:
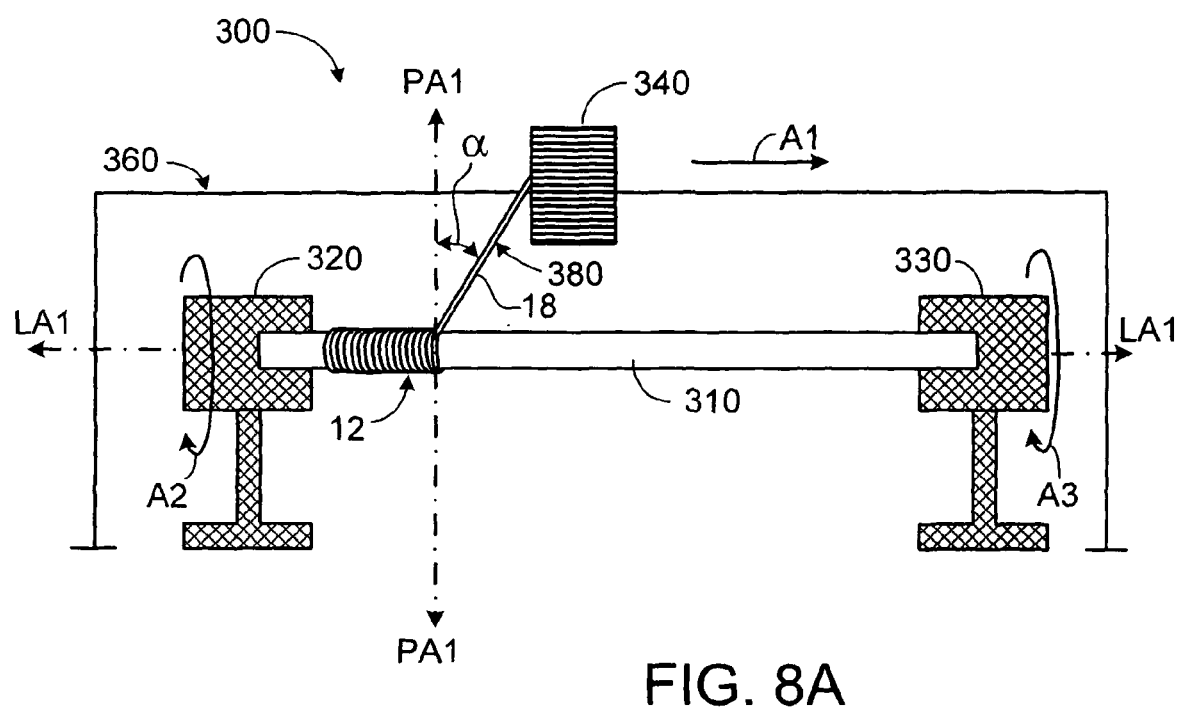
FIG. 8A is a side view of an embodiment of a process for forming an embolic coil.
Figure 8B:
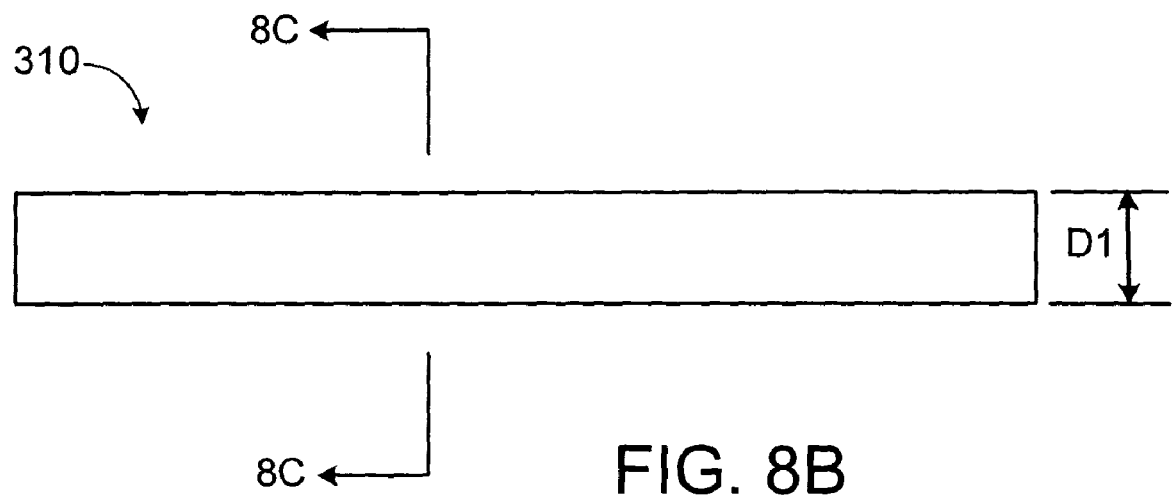
FIG. 8B is a side view of an embodiment of a mandrel used in the process of FIG. 8A.
Figure 8C:
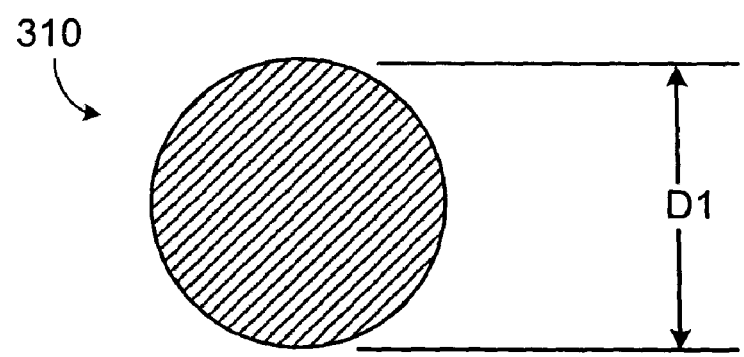
FIG. 8C is a cross-sectional view of the mandrel of FIG. 8B, taken along line 8C-8C.
Figure 9A:
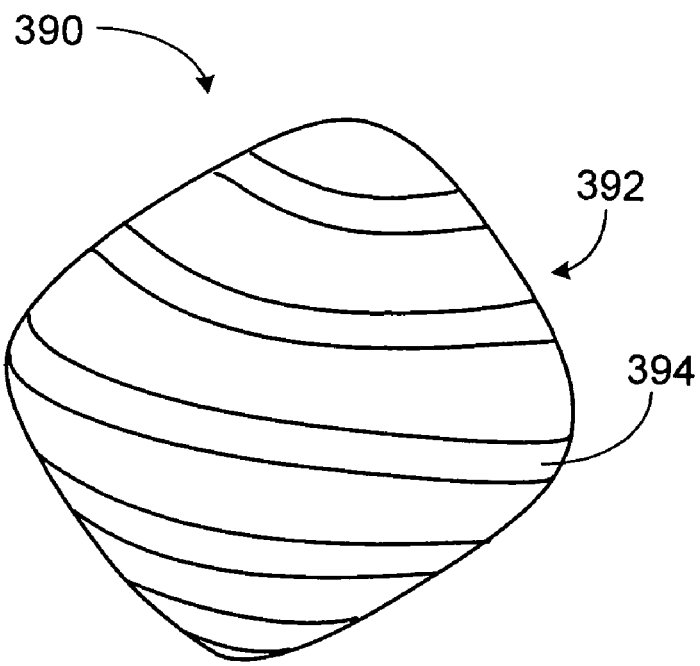
FIG. 9A is a side view of an embodiment of a mandrel.
Figure 9B:
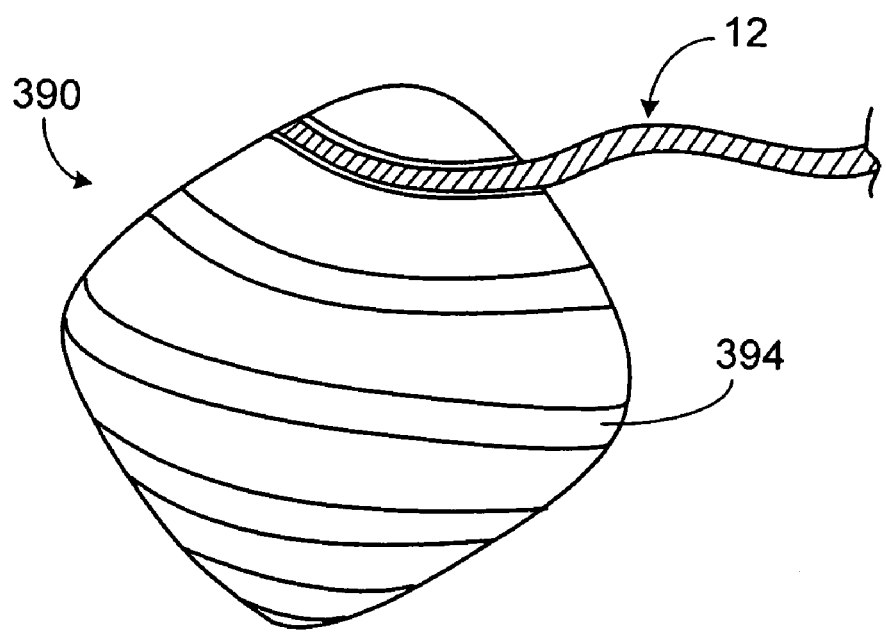
FIGS. 9B and 9C are illustrations of an embodiment of a process for forming an embolic coil using the mandrel of FIG. 9A.
Figure 9C:
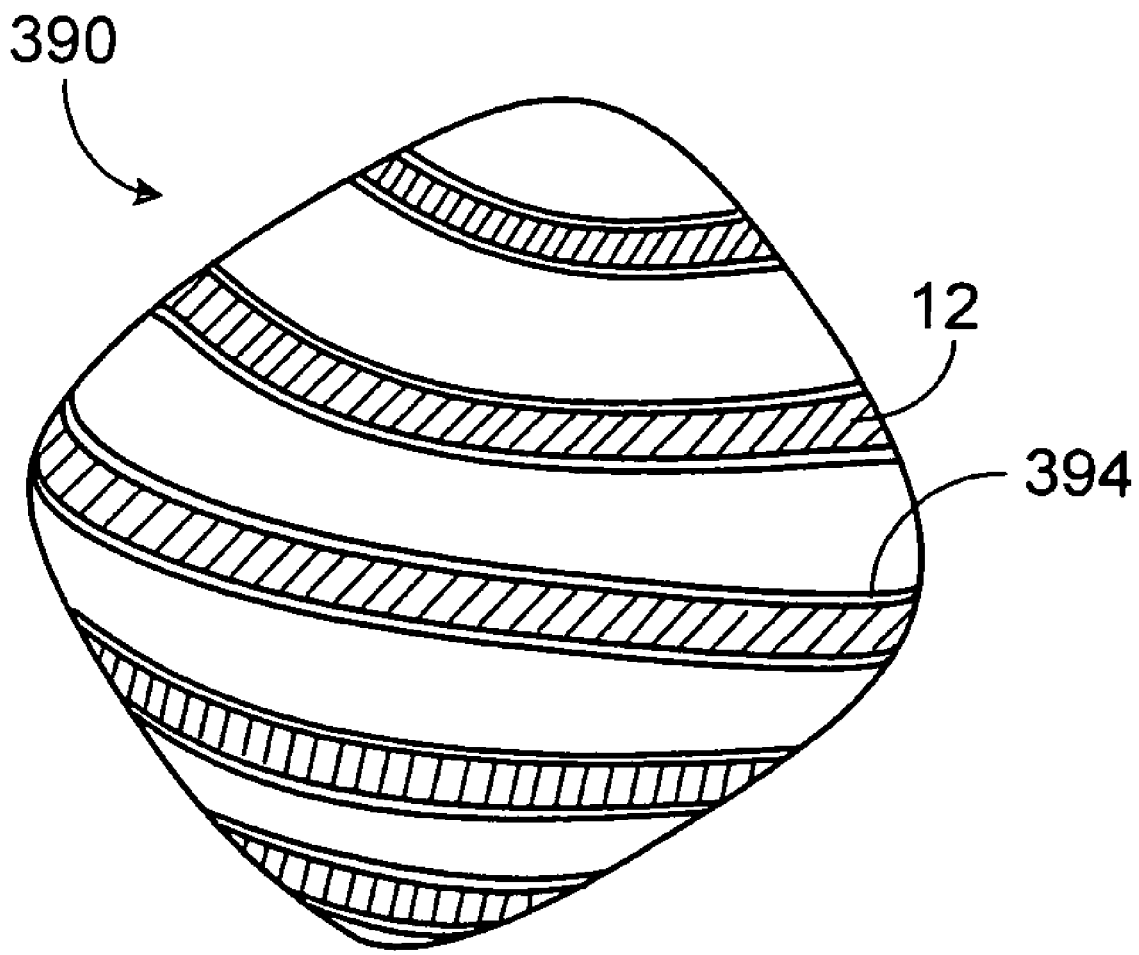

FIGS. 8A-8C illustrate a process for forming a coil body in its primary shape, FIGS. 9A-9C illustrate a process for shaping the coil body into a secondary shape, and FIGS. 10A-10E and 11A-11D illustrate processes for coating a coil body to form a coated embolic coil (e.g., embolic coil 10).

As shown in FIG. 8A, a coil-forming apparatus 300 includes a mandrel 310 held by two rotatable chucks 320 and 330. A spool 340 of wire 18 is disposed above mandrel 310, and is attached to a moving device 360. To form an embolic coil in its primary shape, chucks 320 and 330 are activated so that they rotate in the direction of arrows A2 and A3, thereby rotating mandrel 310. Moving device 360 also is activated, and moves spool 340 in the direction of arrow A1. The rotation of mandrel 310 pulls wire 18 from spool 340 at a predetermined pull-off angle, and causes wire 18 to wrap around mandrel 310, forming coil body 12. The pull-off angle ($\alpha$) is the angle between axis PA1, which is perpendicular to longitudinal axis LA1 of mandrel 310, and the portion 380 of wire 18 between spool 340 and coil body 12. In some embodiments, $\alpha$ can be from about one degree to about six degrees (e.g., from about 1.5 degrees to about five degrees, from about 1.5 degrees to about 2.5 degrees, about two degrees). In certain embodiments, a controller (e.g., a programmable logic controller) can be used to maintain the pull-off angle in coil-forming apparatus 300. Because mandrel 310 is rotating as it is pulling wire 18 from spool 340, and because moving device 360 is moving spool 340 in the direction of arrow A1, wire 18 forms coil body 12 in a primary shape around mandrel 310. Coil body 12 can be formed, for example, at room temperature (25° C.).

After coil body 12 has been formed, chucks 320 and 330, and moving device 360, are deactivated, and portion 380 of wire 18 is cut. Mandrel 310 is then released from chuck 320, and coil body 12 is pulled off of mandrel 310. While coil body 12 might lose some of its primary shape as it is pulled off of mandrel 310, coil body 12 can generally return to its primary shape shortly thereafter, because of memory imparted to coil body 12 during formation. In certain embodiments (e.g., in certain embodiments in which wire 18 is formed of one or more polymers), coil body 12 can be heated after being formed on mandrel 310 and prior to being removed from mandrel 310. This heating can help coil body 12 to retain its primary shape upon removal of coil body 12 from mandrel 310. In some embodiments, after coil body 12 has been removed from mandrel 310, one or both of the ends of coil body 12 can be heated and melted to form rounder, more biocompatible (e.g., atraumatic) ends.

Mandrel 310 can be formed of, for example, a metal or a metal alloy, such as stainless steel. In some embodiments, mandrel 310 can be formed of one or more polymers, such as Teflon® (polytetrafluoroethylene) or Delrin® (polyoxymethylene). In certain embodiments, mandrel 310 can be formed of a shape-memory material, such as Nitinol.

Mandrel 310 has a diameter D1 (FIGS. 8B and 8C). In some embodiments, diameter D1 can be at least 0.001 inch (e.g., at least 0.002 inch, at least 0.005 inch, at least 0.01 inch, at least 0.015 inch, at least 0.02 inch, at least 0.025 inch, at least 0.03 inch, at least 0.035 inch) and/or at most 0.037 inch (e.g., at most 0.035 inch, at most 0.03 inch, at most 0.025 inch, at most 0.02 inch, at most 0.015 inch, at most 0.01 inch, at most 0.005 inch, at most 0.002 inch).

The tension of mandrel 310 as it is held between chucks 320 and 330 preferably is sufficiently high to avoid vibration of mandrel 310 during the winding process, and sufficiently low to avoid stretching of mandrel 310 during the winding process. In some instances, significant stretching of mandrel 310 during the winding process could cause coil body 12 to have a smaller primary shape than desired, and/or could make it relatively difficult to remove coil body 12 from mandrel 310. In certain embodiments, the tension of mandrel 310 can be from about 100 grams to about 1,000 grams (e.g., from about 300 grams to about 600 grams, from about 400 grams to about 500 grams). For example, the tension of mandrel 310 can be about 506 grams.

In some embodiments, wire 18 can be wound around mandrel 310 at a tension of from about 10 grams to about 100 grams (e.g., from about four grams to about 50 grams, from about six grams to about 40 grams, from about 22 grams to about 32 grams, about 27 grams).

In certain embodiments, the length of coil body 12 in its primary shape and while under tension on mandrel 310 can be from about 10 centimeters to about 250 centimeters (e.g., from about 50 centimeters to about 200 centimeters, from about 130 centimeters to about 170 centimeters, from about 144 centimeters to about 153 centimeters, from about 147 centimeters to about 153 centimeters). For example, the length of coil body 12 in its primary shape and while under tension on mandrel 310 can be about 132 centimeters or about 147 centimeters. Coil body 12 may recoil to some extent (e.g., by at most about five centimeters) when portion 380 of wire 18 is severed, such that coil body 12 will be somewhat smaller once it has been removed from mandrel 310. In some embodiments, coil body 12 can have a length of from about five centimeters to about 225 centimeters (e.g., from about 25 centimeters to about 170 centimeters, from about 120 centimeters to about 140 centimeters, from about 137 centimeters to about 140 centimeters) after being removed from mandrel 310. After coil body 12 has been removed from mandrel 310, coil body 12 can be cut into smaller coils.

Once coil body 12 has been formed in its primary shape, coil body 12 can be further shaped into a secondary shape, as shown in FIGS. 9A-9C.

FIG. 9A shows a mandrel 390 used to form the secondary shape of coil body 12. While mandrel 390 is shaped to form a diamond, other types of mandrels can be used to form other secondary shapes. Mandrel 390 is formed of a diamond-shaped block 392 with grooves 394 cut into its surface. As shown in FIGS. 9B and 9C, coil body 12 in its primary shape is wrapped around mandrel 390, such that coil body 12 fills grooves 394, creating the secondary shape. The ends of coil body 12 are then attached (e.g., pinned) to mandrel 390, and coil body 12 is heat-treated to impart memory to coil body 12. In some embodiments, coil body 12 can be heat-treated at a temperature of at least about 1000° C. (e.g., at least about 1050° C., at least about 1100° C., at least about 1150° C.), and/or at most about 1200° C. (e.g., at most about 1150° C., at most about 1100° C., at most about 1050° C.). In certain embodiments, the heat treatment of coil body 12 can last for a period of from about 10 minutes to about 40 minutes (e.g., about 25 minutes). After being heat-treated, coil body 12 is unwrapped from mandrel 390. The removal of coil body 12 from mandrel 390 allows coil body 12 to reassume its secondary shape. In some embodiments, after coil body 12 has been removed from mandrel 390, one or both of the ends of coil body 12 can be heated and melted to form rounder, more biocompatible (e.g., atraumatic) ends.

Mandrel 390 can be formed of, for example, a metal or a metal alloy (e.g., stainless steel). In some embodiments, mandrel 390 can be formed of a plated metal or a plated metal alloy (e.g., chrome-plated stainless steel).

FIGS. 10A-10E illustrate an embodiment of a process that can be used to coat coil body 12.

As shown in FIG. 10A, coil body 12 in its primary shape is placed within a lumen 402 of a cylindrical introducer sheath 400. At its distal end 404, introducer sheath 400 is sealed with a cap 406, and at its proximal end 408, introducer sheath 400 is connected to a female luer lock component 410. Cap 406 and/or female luer lock component 410 can include one or more gas outlets. For example, cap 406 and/or female luer lock component 410 can be shaped to include one or more gas outlets.

The distal end 13 of coil body 12 is attached to cap 406, and the proximal end 15 of coil body 12 is attached to female luer lock component 410, so that coil body 12 is suspended within lumen 402 of introducer sheath 400. A syringe 412 containing a solution 414 including a polymer (e.g., polyvinyl alcohol) and a gelling precursor (e.g., alginate) is then connected to introducer sheath 400 via female luer lock component 410. In some embodiments, solution 414 can include at most about 8.5 weight percent of the polymer (e.g., from about 7.5 weight percent to about 8.5 weight percent, about eight weight percent), and/or at most about 2.5 weight percent (e.g., from about 1.5 weight percent to about 2.5 weight percent, about two weight percent) of the gelling precursor. Solution 414 is injected into lumen 402 of introducer sheath 400, so that solution 414 contacts coil body 12, and partially fills lumen 402.

As shown in FIG. 10B, after solution 414 has been injected into lumen 402, a different syringe 416 containing a solution 418 including a gelling agent is attached to introducer sheath 400. In some embodiments, the concentration of gelling agent in solution 418 can be at least 0.01 weight percent (e.g., at least about two weight percent, at least about five weight percent) and/or at most 10 weight percent (e.g., at most about five weight percent, at most about two weight percent, from about one weight percent to about two weight percent). Solution 418 is then injected into lumen 402. When the gelling agent in solution 418 contacts solution 414 in lumen 402 of introducer sheath 400, the gelling agent can interact with the gelling precursor in solution 414 to form a gel coating 420 (FIG. 10C) on coil body 12 that includes the gelled gelling precursor and the polymer.

Examples of gelling agents include agents including ions, such as multivalent cations (e.g., divalent cations). Examples of such agents include alkali metal salts, alkaline earth metal salts or transition metal salts that can ionically cross-link with a gelling precursor. In some embodiments, an inorganic salt, such as a calcium, barium, zinc or magnesium salt, can be used as a gelling agent. In certain embodiments (e.g., embodiments in which a gelling precursor is alginate), a suitable gelling agent is calcium chloride. The calcium cations have an affinity for carboxylic groups in the gelling precursor. The cations can complex with carboxylic groups in the gelling precursor, forming a gel.

As shown in FIG. 10C, cap 406 can then be removed from introducer sheath 400 and introducer sheath 400 can be cut (e.g., using a razor) and peeled away, exposing a coated coil 422 formed of coil body 12 and gel coating 420. As introducer sheath 400 is peeled away, coated coil 422 assumes its secondary shape. In some embodiments, coated coil 422 can be used in a procedure, such as an embolization procedure.

While FIG. 10C shows introducer sheath 400 being cut and peeled away, in certain embodiments, coated coil 422 can be removed from introducer sheath 400 using other methods. As an example, in some embodiments, introducer sheath 400 can be formed of one or more bioerodible and/or bioabsorbable materials, such as the materials described above. Coated coil 422 can be removed, for example, by eroding and/or absorbing at least part of introducer sheath. As another example, in certain embodiments, introducer sheath 400 can be contacted with an agent (e.g., dimethyl sulfoxide (DMSO)) that causes the material of the introducer sheath to dissolve. As an additional example, in some embodiments, coated coil 422 can be pushed and/or pulled out of introducer sheath 400. As a further example, in certain embodiments, introducer sheath 400 can include slits and/or perforations that allow introducer sheath 400 to be peeled apart to remove coated coil 422.

Figure 10D:
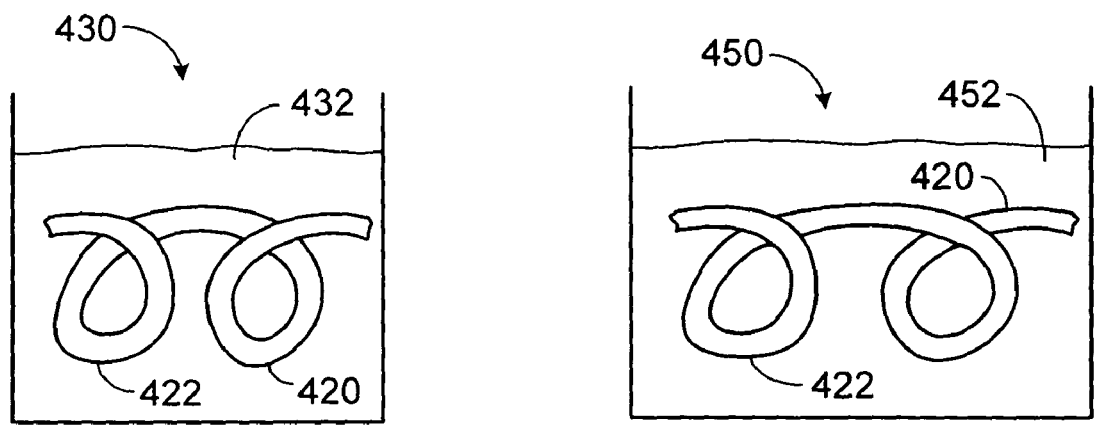

In certain embodiments, after coated coil 422 has been removed from introducer sheath 400, coated coil 422 can be further processed. As shown in FIG. 10D, in some embodiments, coated coil 422 can be added into a reactor vessel 430 containing a mixture 432. Mixture 432 can include components that help to stabilize gel coating 420 by, for example, reacting with (e.g., cross-linking with) the polymer (e.g., polyvinyl alcohol) in gel coating 420. In certain embodiments, mixture 432 can include one or more cross-linking agents. Examples of cross-linking agents include aldehydes (e.g., formaldehyde, glyoxal, benzaldehyde, aterephthalaldehyde, succinaldehyde, glutaraldehyde). In some embodiments in which gel coating 420 includes polyvinyl alcohol, one or more aldehydes can be used to react with the polyvinyl alcohol in an acetalization process. In certain embodiments, one or more acids can be used in conjunction with a cross-linking agent to react with gel coating 420. Examples of acids include strong acids (e.g., sulfuric acid, hydrochloric acid, nitric acid) and weak acids (e.g., acetic acid, formic acid, phosphoric acid).

Figure 10E:
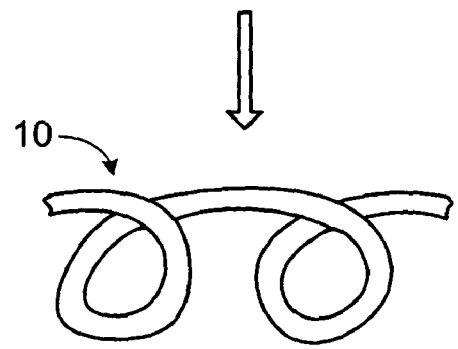

As FIG. 10E shows, in certain embodiments, after gel coating 420 has been stabilized, coated coil 422 can be added into a gel dissolution vessel 450 that contains a gel dissolution mixture 452, to form embolic coil 10. Upon contacting coated coil 422, gel dissolution mixture 452 can remove the gelled gelling precursor from coating 420 (e.g., by an ion-exchange reaction), thereby forming embolic coil 10. In some embodiments (e.g., some embodiments in which the gelling precursor is sodium alginate), the gelling precursor can be removed from coating 420 by ion-exchange with a solution of sodium hexa-metaphosphate (e.g., from EMD Chemicals Inc., Gibbstown, N.J.). In certain embodiments, the solution can include ethylenediaminetetracetic acid (EDTA), citric acid, one or more other acids, and/or one or more phosphates. In some embodiments, the solution can have a concentration of sodium hexa-metaphosphate of at least about one weight percent (e.g., at least about five weight percent, at least about 10 weight percent) and/or at most about 20 weight percent (e.g., at most about 10 weight percent, at most about five weight percent) in deionized water. After embolic coil 10 has been formed, embolic coil 10 can be removed from gel dissolution vessel 450.

While FIGS. 10A-10E show certain methods of coating a coil body to form a coated embolic coil, other methods can be used. For example, FIGS. 11A-11D illustrate methods that can be used to form an embolic coil such as embolic coil 50 (FIGS. 2A-2C).

As shown in FIGS. 11A and 11B, coil body 52 in its primary shape is placed into a lumen 502 of an introducer sheath 500, which has an inner diameter ID3 and an outer diameter OD4.

In some embodiments, inner diameter ID3 can be at least 0.008 inch (e.g., at least 0.01 inch, at least 0.015 inch, at least 0.02 inch, at least 0.021 inch, at least 0.025 inch, at least 0.03 inch, at least 0.035 inch), and/or at most 0.038 inch (e.g., at most 0.035 inch, at most 0.03 inch, at most 0.025 inch, at most 0.021 inch, at most 0.02 inch, at most 0.015 inch, at most 0.01 inch). For example, in certain embodiments, inner diameter ID3 can be 0.018 inch. In some embodiments, inner diameter ID3 can be 0.026 inch.

In certain embodiments, outer diameter OD4 can be at least 0.01 inch (e.g., at least 0.015 inch, at least 0.02 inch, at least 0.03 inch, at least 0.04 inch, at least 0.042 inch, at least 0.05 inch) and/or at most 0.06 inch (e.g., at most 0.05 inch, at most 0.042 inch, at most 0.04 inch, at most 0.03 inch, at most 0.02 inch, at most 0.015 inch).

At its proximal end 504, introducer sheath 500 is connected to a female luer lock component 506. As shown in FIG. 11B, coil body 52 is not suspended within lumen 502. Rather, coil body 52 is in some contact with a wall 508 of introducer sheath 500.

Figure 11C:
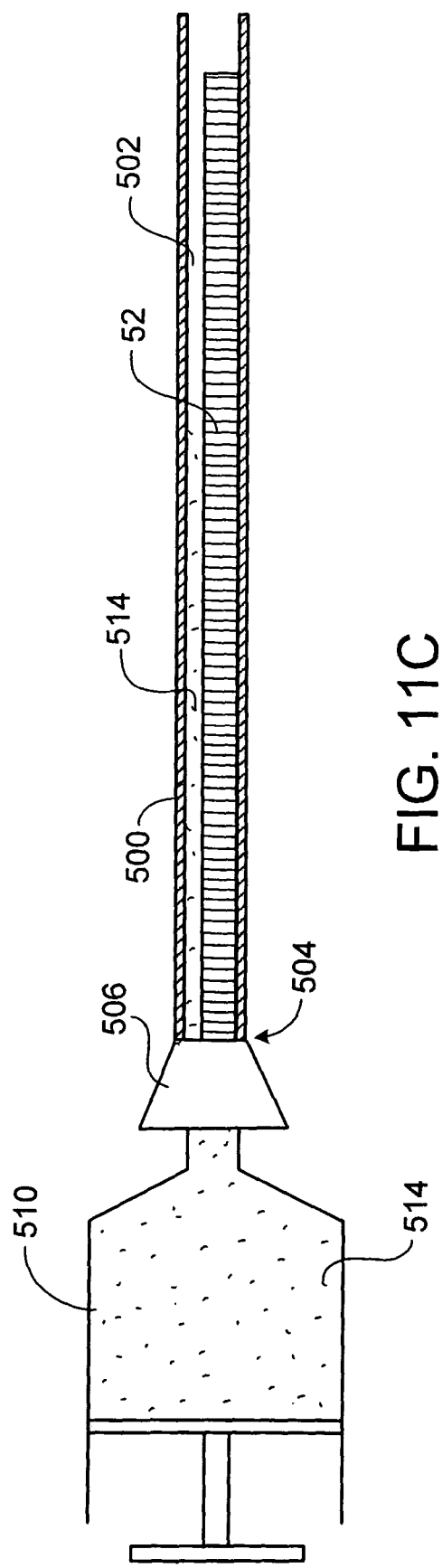
Figure 11D:
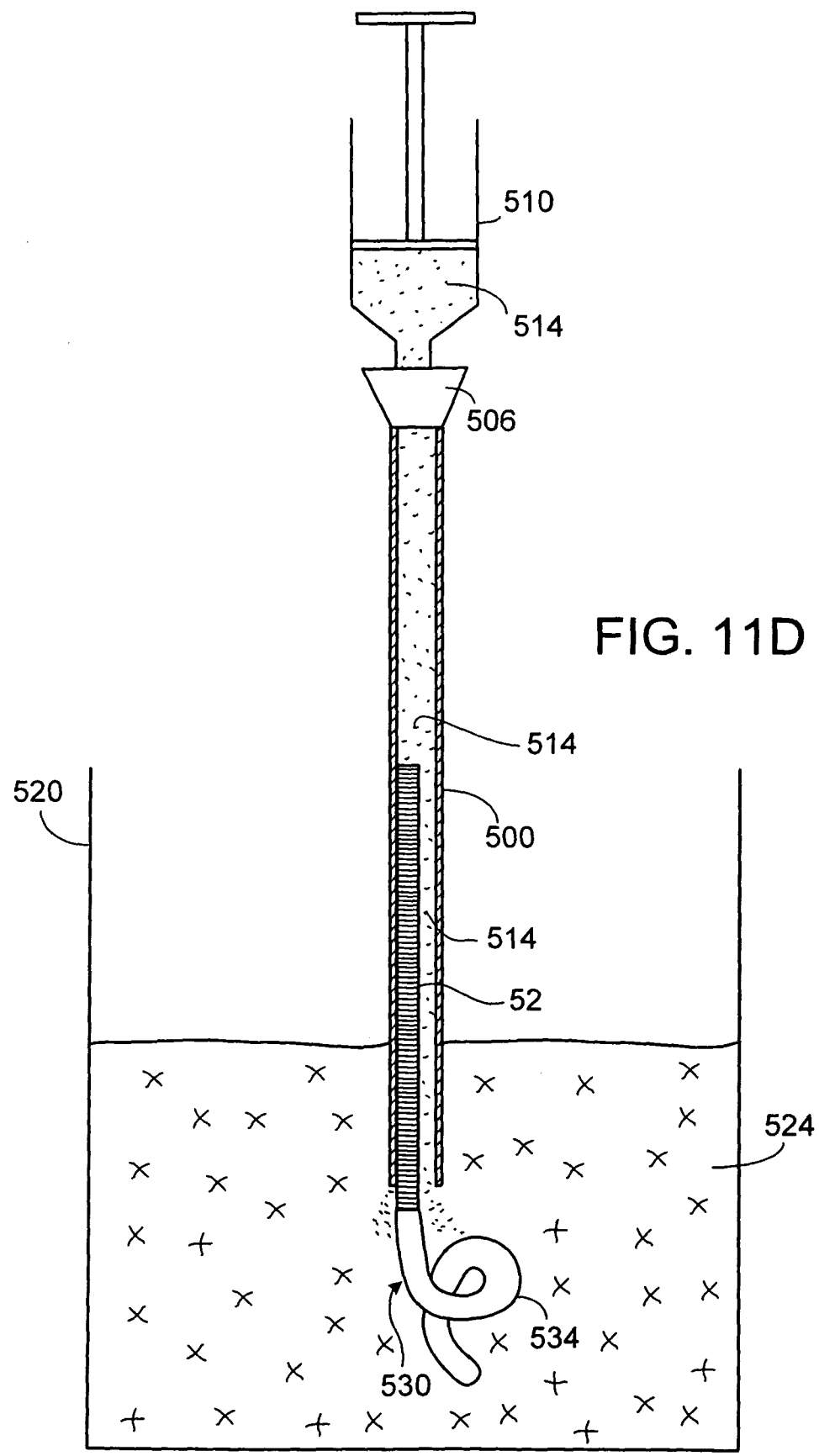

As FIG. 11C shows, a syringe 510 containing a solution 514 including a polymer (e.g., polyvinyl alcohol) and a gelling precursor (e.g., alginate) is then connected to introducer sheath 500 via female luer lock component 506. Solution 514 is partially injected into lumen 502 of introducer sheath 500, so that solution 514 contacts coil body 52. As shown in FIG. 11D, after solution 514 has flowed over at least a portion of coil body 52, syringe 510 is used to inject both solution 514 and coil body 52 into a vessel 520 containing a solution 524 including a gelling agent. As coil body 52 is delivered into solution 524, the interaction between solution 514 and solution 524 at the surface of coil body 52 results in the formation of a coated coil 530 formed out of coil body 52 and a gel coating 534. Coated coil 530 can be used in a procedure (e.g., an embolization procedure), or can be further processed (e.g., by being exposed to a reactor vessel and/or a gel dissolution vessel, as described above) to form an embolic coil such as embolic coil 50.

While FIGS. 10A-10E and 11A-11D illustrate methods of coating coil body 12 after coil body 12 has been formed into its secondary shape, in some embodiments, other methods can be used to form a coated coil. As an example, in certain embodiments, coil body 12 can be coated prior to being formed into a secondary shape. As another example, in some embodiments, wire 18 can include a coating. Thus, when wire 18 is used to form coil body 12, coil body 12 can also include the coating. Wire 18 can be coated using, for example, one or more spray coating methods and/or dip coating methods.

Embolic coils and methods of making embolic coils are described, for example, in Elliott et al., U.S. patent application Ser. No. 11/000,741, filed on Dec. 1, 2004, and entitled "Embolic Coils", which is incorporated herein by reference. Methods of forming gels, stabilizing polymers, and dissolving gels are described, for example, in Lanphere et al., U.S. Patent Application Publication No. U.S. 2004/0096662 A1, published on May 20, 2004, and entitled "Embolization"; and in DiCarlo et al., U.S. patent application Ser. No. 11/111,511, filed on Apr. 21, 2005, and entitled "Particles", both of which are incorporated herein by reference.

In some embodiments, an embolic coil such as embolic coil 10 can include one or more therapeutic agents (e.g., drugs). For example, coil body 12 and/or coating 20 of embolic coil 10 can include one or more therapeutic agents. Embolic coil 10 can, for example, be used to deliver the therapeutic agents to a target site.

In certain embodiments, one component of embolic coil 10 (e.g., coil body 12) can include one or more therapeutic agents that are the same as, or different from, one or more therapeutic agents in coating 20. In some embodiments, therapeutic agents can be dispersed within coating 20. In certain embodiments, coating 20 can be formed of one or more bioerodible and/or bioabsorbable materials, and can contain one or more therapeutic agents (e.g., heparin) that limit and/or prevent thrombosis. When coating 20 is eroded and/or absorbed, thereby releasing the therapeutic agent into the body of the subject (e.g., during delivery), the therapeutic agent can limit or prevent premature thrombosis.

In some embodiments, embolic coil 10 can include one or more therapeutic agents that are coated onto coil body 12, and/or that are coated onto coating 20. In some embodiments, a therapeutic agent can be compounded with a polymer that is included in coating 20. In certain embodiments, a therapeutic agent can be applied to the surface of coil body 12 and/or to coating 20 by exposing coil body 12 and/or coating 20 to a high concentration solution of the therapeutic agent.

In some embodiments, a therapeutic agent-coated embolic coil can include a coating (e.g., a bioerodible and/or bioabsorbable polymer coating) over the surface the therapeutic agent. The coating can assist in controlling the rate at which therapeutic agent is released from the embolic coil. For example, the coating can be in the form of a porous membrane. The coating can delay an initial burst of therapeutic agent release. The coating can be applied by dipping or spraying the embolic coil. The coating can include therapeutic agent or can be substantially free of therapeutic agent. The therapeutic agent in the coating can be the same as or different from an agent on a surface layer of the embolic coil body, and/or in a coating on the embolic coil body, and/or within the embolic coil body. A polymer coating (e.g., that is bioerodible and/or bioabsorbable) can be applied to an embolic coil body surface and/or to a coated embolic coil surface in embodiments in which a high concentration of therapeutic agent has not been applied to the embolic coil body surface or to the coated coil surface.

Coatings are described, for example, in DiMatteo et al., U.S. Patent Application Publication No. U.S. 2004/0076582 A1, published on Apr. 22, 2004, and entitled "Agent Delivery Particle", which is incorporated herein by reference.

In some embodiments, one or more coils can be disposed in a therapeutic agent that can serve as a pharmaceutically acceptable carrier.

Therapeutic agents include genetic therapeutic agents, non-genetic therapeutic agents, and cells, and can be negatively charged, positively charged, amphoteric, or neutral. Therapeutic agents can be, for example, materials that are biologically active to treat physiological conditions; pharmaceutically active compounds; gene therapies; nucleic acids with and without carrier vectors (e.g., recombinant nucleic acids, DNA (e.g., naked DNA), cDNA, RNA, genomic DNA, cDNA or RNA in a non-infectious vector or in a viral vector which may have attached peptide targeting sequences, antisense nucleic acids (RNA, DNA)); peptides (e.g., growth factor peptides, such as basic fibroblast growth factor (bFGF)); oligonucleotides; gene/vector systems (e.g., anything that allows for the uptake and expression of nucleic acids); DNA chimeras (e.g., DNA chimeras which include gene sequences and encoding for ferry proteins such as membrane translocating sequences ("MTS") and herpes simplex virus-1 ("VP22")); compacting agents (e.g., DNA compacting agents); viruses; polymers; hyaluronic acid; proteins (e.g., enzymes such as ribozymes, asparaginase, and/or matrix metalloproteinases; cytokines such as growth factors and/or IL-1); immunologic species; nonsteroidal anti-inflammatory medications; chemoagents; pain management therapeutics; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; thrombogenic agents; antioxidants; angiogenic and anti-angiogenic agents and factors; anti-proliferative agents (e.g., agents capable of blocking smooth muscle cell proliferation); calcium entry blockers; and survival genes which protect against cell death (e.g., anti-apoptotic Bcl-2 family factors and Akt kinase). Additional example of therapeutic agents include cell fragments and cell components, such as cell membranes and cell surface receptors. Further examples of therapeutic agents include tissue fragments and tissue components, such as extracellular matrix and endothelial sheets.

Exemplary non-genetic therapeutic agents include: anti-thrombotic agents such as heparin, heparin derivatives, urokinase, and PPack (dextrophenylalanine proline arginine chloromethylketone); thrombus-stabilizing agents such as Factor XIII; anti-inflammatory agents such as dexamethasone, prednisolone, corticosterone, budesonide, estrogen, acetyl salicylic acid, sulfasalazine and mesalamine; antineoplastic/antiproliferative/anti-mitotic agents such as paclitaxel, 5-fluorouracil, cisplatin, methotrexate, doxorubicin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet factors or peptides; vascular cell growth promoters such as growth factors, transcriptional activators, and translational promoters; vascular cell growth inhibitors such as growth factor inhibitors (e.g., PDGF inhibitor-Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; and agents that interfere with endogenous vasoactive mechanisms.

Exemplary genetic therapeutic agents include: anti-sense DNA and RNA; DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor a, hepatocyte growth factor, and insulin like growth factor, cell cycle inhibitors including CD inhibitors, thymidine kinase ("TK") and other agents useful for interfering with cell proliferation, and the family of bone morphogenic proteins ("BMP's"), including BMP2, BMP3, BMP4, BMP5, BMP6 (Vgr1), BMP7 (OP1), BMP8, BMP9, BMP10, BM11, BMP12, BMP13, BMP14, BMP15, and BMP16. Currently preferred BMP's are any of BMP2, BMP3, BMP4, BMP5, BMP6 and BMP7. These dimeric proteins can be provided as homodimers, heterodimers, or combinations thereof, alone or together with other molecules. Alternatively or additionally, molecules capable of inducing an upstream or downstream effect of a BMP can be provided. Such molecules include any of the "hedgehog" proteins, or the DNA's encoding them. Vectors of interest for delivery of genetic therapeutic agents include: plasmids; viral vectors such as adenovirus (AV), adenoassociated virus (AAV) and lentivirus; and non-viral vectors such as lipids, liposomes and cationic lipids.

Cells include cells of human origin (autologous or allogeneic), including platelets and stem cells, or from an animal source (xenogeneic), which can be genetically engineered if desired to deliver proteins of interest.

Several of the above and numerous additional therapeutic agents appropriate for the practice of the present invention are disclosed in Kunz et al., U.S. Pat. No. 5,733,925, assigned to NeoRx Corporation, which is incorporated herein by reference. Therapeutic agents disclosed in this patent include the following:

"Cytostatic agents" (i.e., agents that prevent or delay cell division in proliferating cells, for example, by inhibiting replication of DNA or by inhibiting spindle fiber formation). Representative examples of cytostatic agents include modified toxins, methotrexate, adriamycin, radionuclides (e.g., such as disclosed in Fritzberg et al., U.S. Pat. No. 4,897,255), protein kinase inhibitors, including staurosporin, a protein kinase C inhibitor of the following formula:

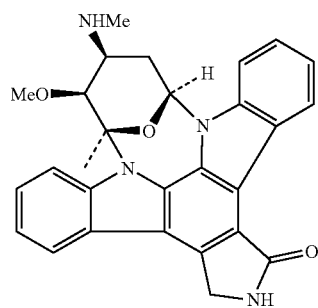

as well as diindoloalkaloids having one of the following general structures:

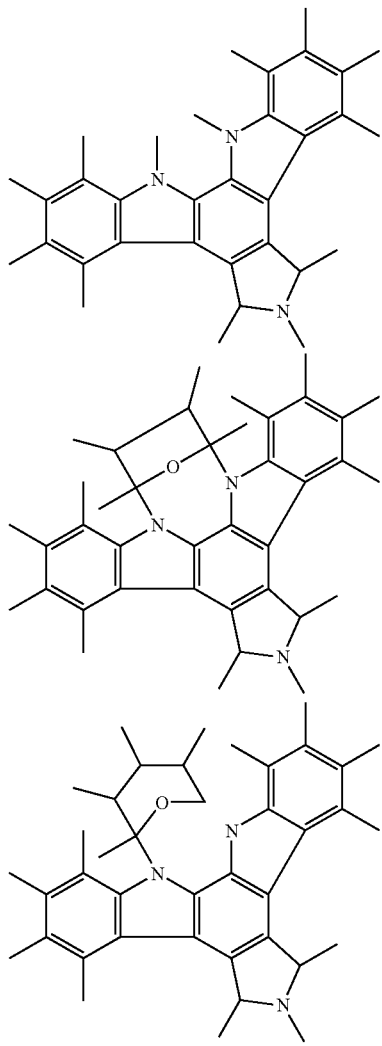

as well as stimulators of the production or activation of TGF-beta, including Tamoxifen and derivatives of functional equivalents (e.g., plasmin, heparin, compounds capable of reducing the level or inactivating the lipoprotein Lp(a) or the glycoprotein apolipoprotein(a)) thereof, TGF-beta or functional equivalents, derivatives or analogs thereof, suramin, nitric oxide releasing compounds (e.g., nitroglycerin) or analogs or functional equivalents thereof, paclitaxel or analogs thereof (e.g., taxotere), inhibitors of specific enzymes (such as the nuclear enzyme DNA topoisomerase II and DNA polymerase, RNA polymerase, adenyl guanyl cyclase), superoxide dismutase inhibitors, terminal deoxynucleotidyl-transferase, reverse transcriptase, antisense oligonucleotides that suppress smooth muscle cell proliferation and the like. Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes: e.g., cytokines (e.g., interleukins such as IL-1), growth factors (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents addressing smooth muscle proliferation include: subfragments of heparin, triazolopyrimidine (trapidil; a PDGF antagonist), lovastatin, and prostaglandins E1 or I2.

Agents that inhibit the intracellular increase in cell volume (i.e., the tissue volume occupied by a cell), such as cytoskeletal inhibitors or metabolic inhibitors. Representative examples of cytoskeletal inhibitors include colchicine, vinblastin, cytochalasins, paclitaxel and the like, which act on microtubule and microfilament networks within a cell. Representative examples of metabolic inhibitors include staurosporin, trichothecenes, and modified diphtheria and ricin toxins, Pseudomonas exotoxin and the like. Trichothecenes include simple trichothecenes (i.e., those that have only a central sesquiterpenoid structure) and macrocyclic trichothecenes (i.e., those that have an additional macrocyclic ring), e.g., a verrucarins or roridins, including Verrucarin A, Verrucarin B, Verrucarin J (Satratoxin C), Roridin A, Roridin C, Roridin D, Roridin E (Satratoxin D), Roridin H.

Agents acting as an inhibitor that blocks cellular protein synthesis and/or secretion or organization of extracellular matrix (i.e., an "anti-matrix agent"). Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation in to a pathologically proliferating form.

Agents that are cytotoxic to cells, particularly cancer cells. Preferred agents are Roridin A, Pseudomonas exotoxin and the like or analogs or functional equivalents thereof. A plethora of such therapeutic agents, including radioisotopes and the like, have been identified and are known in the art. In addition, protocols for the identification of cytotoxic moieties are known and employed routinely in the art.

A number of the above therapeutic agents and several others have also been identified as candidates for vascular treatment regimens, for example, as agents targeting restenosis. Such agents include one or more of the following: calcium-channel blockers, including benzothiazapines (e.g., diltiazem, clentiazem); dihydropyridines (e.g., nifedipine, amlodipine, nicardapine); phenylalkylamines (e.g., verapamil); serotonin pathway modulators, including 5-HT antagonists (e.g., ketanserin, naftidrofuryl) and 5-HT uptake inhibitors (e.g., fluoxetine); cyclic nucleotide pathway agents, including phosphodiesterase inhibitors (e.g., cilostazole, dipyridamole), adenylate/guanylate cyclase stimulants (e.g., forskolin), and adenosine analogs; catecholamine modulators, including α-antagonists (e.g., prazosin, bunazosine), β-antagonists (e.g., propranolol), and α/β-antagonists (e.g., labetalol, carvedilol); endothelin receptor antagonists; nitric oxide donors/releasing molecules, including organic nitrates/nitrites (e.g., nitroglycerin, isosorbide dinitrate, amyl nitrite), inorganic nitroso compounds (e.g., sodium nitroprusside), sydnonimines (e.g., molsidomine, linsidomine), nonoates (e.g., diazenium diolates, NO adducts of alkanediamines), S-nitroso compounds, including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), C-nitroso-, O-nitroso- and N-nitroso-compounds, and L-arginine; ACE inhibitors (e.g., cilazapril, fosinopril, enalapril); ATII-receptor antagonists (e.g., saralasin, losartin); platelet adhesion inhibitors (e.g., albumin, polyethylene oxide); platelet aggregation inhibitors, including aspirin and thienopyridine (ticlopidine, clopidogrel) and GP IIb/IIIa inhibitors (e.g., abciximab, epitifibatide, tirofiban, intergrilin); coagulation pathway modulators, including heparinoids (e.g., heparin, low molecular weight heparin, dextran sulfate, β-cyclodextrin tetradecasulfate), thrombin inhibitors (e.g., hirudin, hirulog, PPACK (D-phe-L-propyl-L-arg-chloromethylketone), argatroban), FXa inhibitors (e.g., antistatin, TAP (tick anticoagulant peptide)), vitamin K inhibitors (e.g., warfarin), and activated protein C; cyclooxygenase pathway inhibitors (e.g., aspirin, ibuprofen, flurbiprofen, indomethacin, sulfinpyrazone); natural and synthetic corticosteroids (e.g., dexamethasone, prednisolone, methprednisolone, hydrocortisone); lipoxygenase pathway inhibitors (e.g., nordihydroguairetic acid, caffeic acid; leukotriene receptor antagonists; antagonists of E- and P-selectins; inhibitors of VCAM-1 and ICAM-1 interactions; prostaglandins and analogs thereof, including prostaglandins such as PGE1 and PGI2; prostacyclin analogs (e.g., ciprostene, epoprostenol, carbacyclin, iloprost, beraprost); macrophage activation preventers (e.g., bisphosphonates); HMG-CoA reductase inhibitors (e.g., lovastatin, pravastatin, fluvastatin, simvastatin, cerivastatin); fish oils and omega-3-fatty acids; free-radical scavengers/antioxidants (e.g., probucol, vitamins C and E, ebselen, retinoic acid (e.g., trans-retinoic acid), SOD mimics); agents affecting various growth factors including FGF pathway agents (e.g., bFGF antibodies, chimeric fusion proteins), PDGF receptor antagonists (e.g., trapidil), IGF pathway agents (e.g., somatostatin analogs such as angiopeptin and ocreotide), TGF-β pathway agents such as polyanionic agents (heparin, fucoidin), decorin, and TGF-β antibodies, EGF pathway agents (e.g., EGF antibodies, receptor antagonists, chimeric fusion proteins), TNF-α pathway agents (e.g., thalidomide and analogs thereof), thromboxane A2 (TXA2) pathway modulators (e.g., sulotroban, vapiprost, dazoxiben, ridogrel), protein tyrosine kinase inhibitors (e.g., tyrphostin, genistein, and quinoxaline derivatives); MMP pathway inhibitors (e.g., marimastat, ilomastat, metastat), and cell motility inhibitors (e.g., cytochalasin B); antiproliferative/antineoplastic agents including antimetabolites such as purine analogs (e.g., 6-mercaptopurine), pyrimidine analogs (e.g., cytarabine and 5-fluorouracil) and methotrexate, nitrogen mustards, alkyl sulfonates, ethylenimines, antibiotics (e.g., daunorubicin, doxorubicin, daunomycin, bleomycin, mitomycin, penicillins, cephalosporins, ciprofalxin, vancomycins, aminoglycosides, quinolones, polymyxins, erythromycins, tertacyclines, chloramphenicols, clindamycins, linomycins, sulfonamides, and their homologs, analogs, fragments, derivatives, and pharmaceutical salts), nitrosoureas (e.g., carmustine, lomustine) and cisplatin, agents affecting microtubule dynamics (e.g., vinblastine, vincristine, colchicine, paclitaxel, epothilone), caspase activators, proteasome inhibitors, angiogenesis inhibitors (e.g., endostatin, angiostatin and squalamine), and rapamycin, cerivastatin, flavopiridol and suramin; matrix deposition/organization pathway inhibitors (e.g., halofuginone or other quinazolinone derivatives, tranilast); endothelialization facilitators (e.g., VEGF and RGD peptide); and blood rheology modulators (e.g., pentoxifylline).

Other examples of therapeutic agents include anti-tumor agents, such as docetaxel, alkylating agents (e.g., mechlorethamine, chlorambucil, cyclophosphamide, melphalan, ifosfamide), plant alkaloids (e.g., etoposide), inorganic ions (e.g., cisplatin), biological response modifiers (e.g., interferon), and hormones (e.g., tamoxifen, flutamide), as well as their homologs, analogs, fragments, derivatives, and pharmaceutical salts.

Additional examples of therapeutic agents include organic-soluble therapeutic agents, such as mithramycin, cyclosporine, and plicamycin. Further examples of therapeutic agents include pharmaceutically active compounds, anti-sense genes, viral, liposomes and cationic polymers (e.g., selected based on the application), biologically active solutes (e.g., heparin), prostaglandins, prostcyclins, L-arginine, nitric oxide (NO) donors (e.g., lisidomine, molsidomine, NO-protein adducts, NO-polysaccharide adducts, polymeric or oligomeric NO adducts or chemical complexes), enoxaparin, Warafin sodium, dicumarol, interferons, chymase inhibitors (e.g., Tranilast), ACE inhibitors (e.g., Enalapril), serotonin antagonists, 5-HT uptake inhibitors, and beta blockers, and other antitumor and/or chemotherapy drugs, such as BiCNU, busulfan, carboplatinum, cisplatinum, cytoxan, DTIC, fludarabine, mitoxantrone, velban, VP-16, herceptin, leustatin, navelbine, rituxan, and taxotere.

Therapeutic agents are described, for example, in DiMatteo et al., U.S. Patent Application Publication No. U.S. 2004/0076582 A1, published on Apr. 22, 2004, and entitled "Agent Delivery Particle", in Pinchuk et al., U.S. Pat. No. 6,545,097, and in Schwarz et al., U.S. Pat. No. 6,368,658, all of which are incorporated herein by reference.

EXAMPLES

The following examples are illustrative and not intended to be limiting.

Example 1

Nine embolic coils were prepared. The following procedure was used for preparing each coil.

A platinum helical coil (a GDC®-18 Standard coil, UPN M00335083040, from Boston Scientific Corp.) having an outer diameter of 0.015 inch (0.381 millimeter) in its primary shape, an outer diameter of six millimeters in its secondary shape, and a length of 200 millimeters in its primary shape, was cut so that its primary shape length was about 100 millimeters. The coil from a VortX®-18 Diamond-Shaped Fibered Platinum Coil system (UPN M0013822030, from Boston Scientific Corp.) was removed from the introducer sheath of the system. The GDC®-18 Standard coil was then inserted into the distal end of the introducer sheath.

A polymer solution including eight percent by weight polyvinyl alcohol (from Sigma-Aldrich) and two percent by weight sodium alginate (from FMC Biopolymer, Philadelphia, Pa.) in deionized water was prepared. The polymer solution was then autoclaved using a benchtop autoclave (from Tuttnauer Co. Ltd., Hauppauge, N.Y.). The polymer solution was autoclaved for one standard cycle of 121° C. for 30 minutes.

The polymer solution was allowed to cool to room temperature (25° C.), and then was aspirated into a syringe (from Becton Dickinson).

The syringe was attached to the luer fitting of the coil introducer sheath, and the polymer solution was gently injected so that it filled the interstitial space of the coil introducer sheath, thereby surrounding the coil.

The distal end of the coil introducer sheath was inserted into a beaker containing a calcium chloride solution including one percent by weight calcium chloride in deionized water.

The polymer solution was forcefully injected into the calcium chloride solution from the syringe. The forceful ejection also caused the coil to be injected into the calcium chloride solution.

The polymer solution formed a coating around the coil when the polymer solution contacted the calcium chloride solution. Without wishing to be bound by theory, it is believed that the coating was formed of cross-linked alginate and polyvinyl alcohol.

A reaction solution of including four percent by weight formaldehyde (from EMD Chemicals Inc. (formerly EM Industries, Inc. and EM Science), Gibbstown, N.J.) and 20 percent by weight sulfuric acid (from EMD Chemicals Inc. (formerly EM Industries, Inc. and EM Science), Gibbstown, N.J.) in deionized water was prepared.

The reaction solution, which was contained in a flask, was heated with shaking in a water shaker bath at 65° C. The shaker bath was an orbital shaker bath that restrained the reaction flask during shaking.

The coated coil was removed from the calcium chloride solution and placed in the flask containing the reaction solution, which was located in the shaker bath. The shaker bath was an orbital shaker bath that restrained the reaction flask during shaking. The coated coil remained in the flask for 20 minutes at 65° C., as the flask was being shaken by the orbital shaker bath, until the coating in the coil turned white. Without wishing to be bound by theory, it is believed that when the coating on the coil turns white, the formaldehyde in the reaction solution has cross-linked the polyvinyl alcohol in the coil coating.

The coated coil was then removed from the flask and was rinsed in deionized water two times, for 15 minutes each time.

The coated coil was stirred in a solution including deionized water and five percent sodium hexametaphosphate, at room temperature (25° C.) for 30 minutes.

The coated coil was then removed from the sodium hexametaphosphate solution, and was rinsed in deionized water two times, for 15 minutes each time.

The above process was repeated to produce a total of nine embolic coils.

Figure 12:
FIGS. 12-16 are micrographs of embodiments of embolic coils.
Figure 13:
Figure 14:
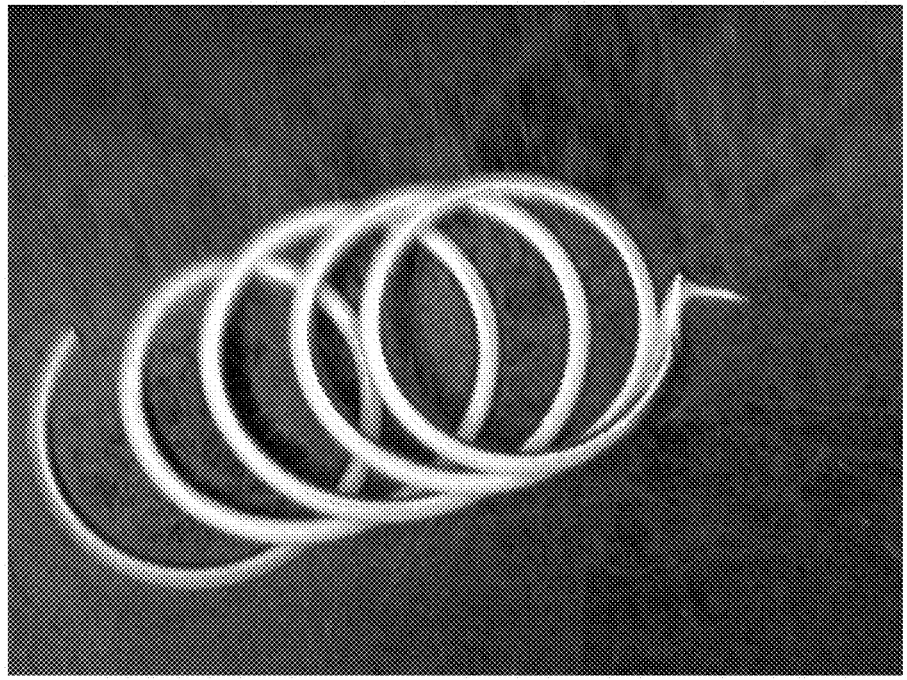
Figure 15:
Figure 16:
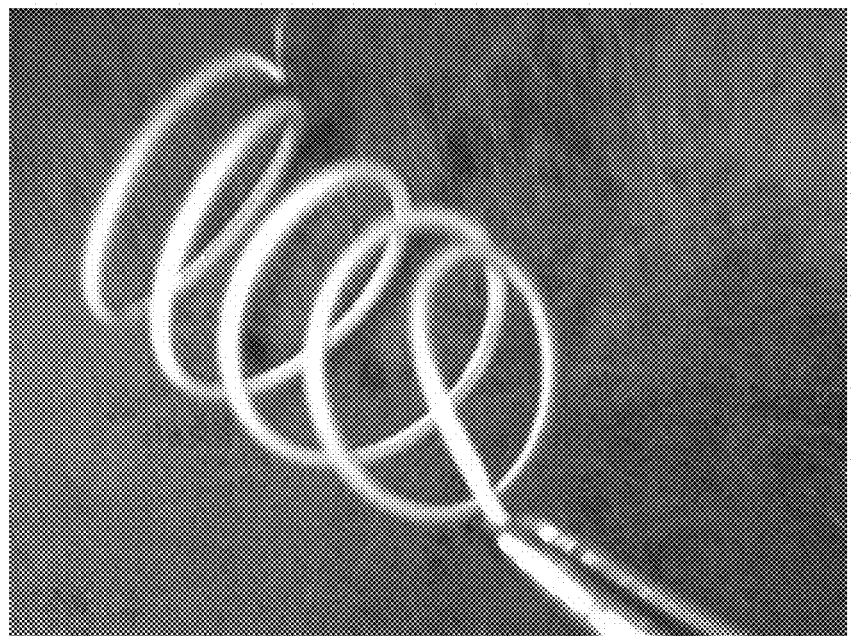

FIGS. 12-16 are micrographs of some of the embolic coils produced by the above method, taken using a microscope. FIG. 12 is a micrograph of an embolic coil at 10× magnification, FIG. 13 is a micrograph of an embolic coil at 30× magnification, FIG. 14 is a micrograph of an embolic coil at 10× magnification, FIG. 15 is a micrograph of an embolic coil at 10× magnification, and FIG. 16 is a micrograph of an embolic coil at 10× magnification.

Figure 17:
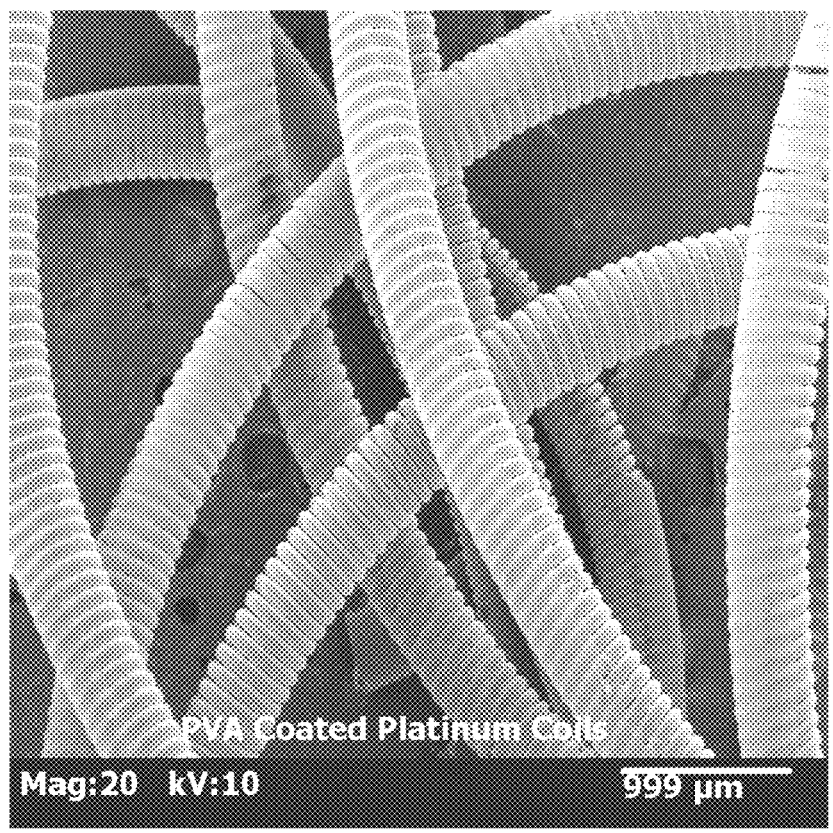
FIG. 17 is a scanning electron microscope (SEM) image of embodiments of embolic coils.

FIG. 17 is an SEM image, at 20× magnification, of some of the embolic coils produced by the above method.

Figure 18A:
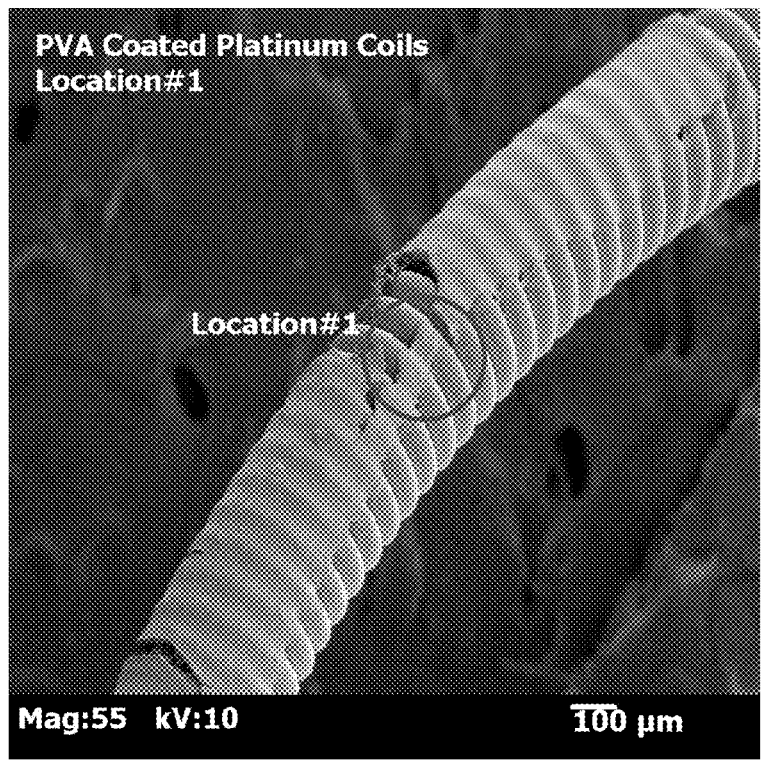
FIGS. 18A-18F are SEM images of a location on one of the embolic coils of FIG. 17, taken at different levels of magnification.
Figure 18B:
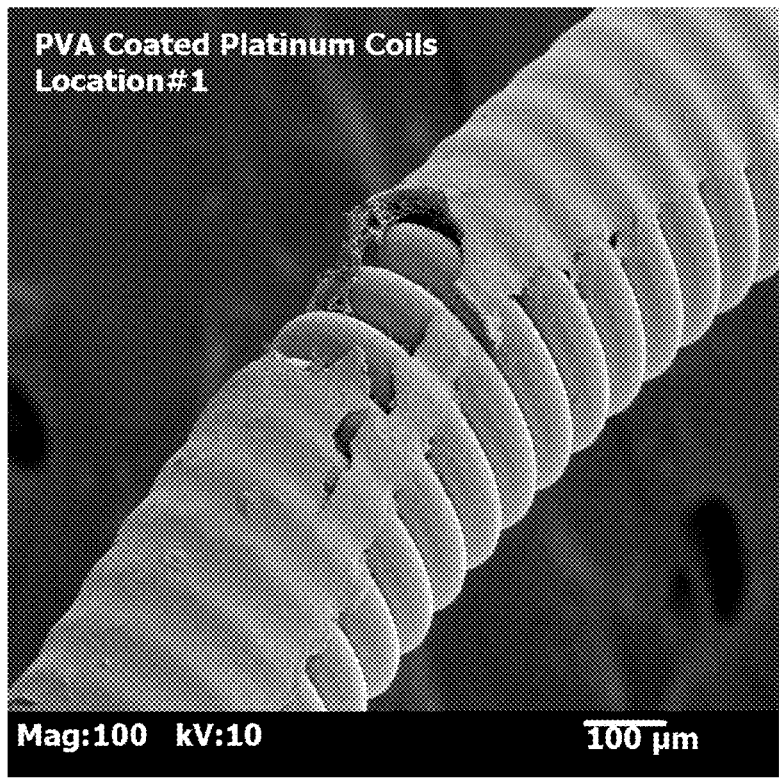
Figure 18C:
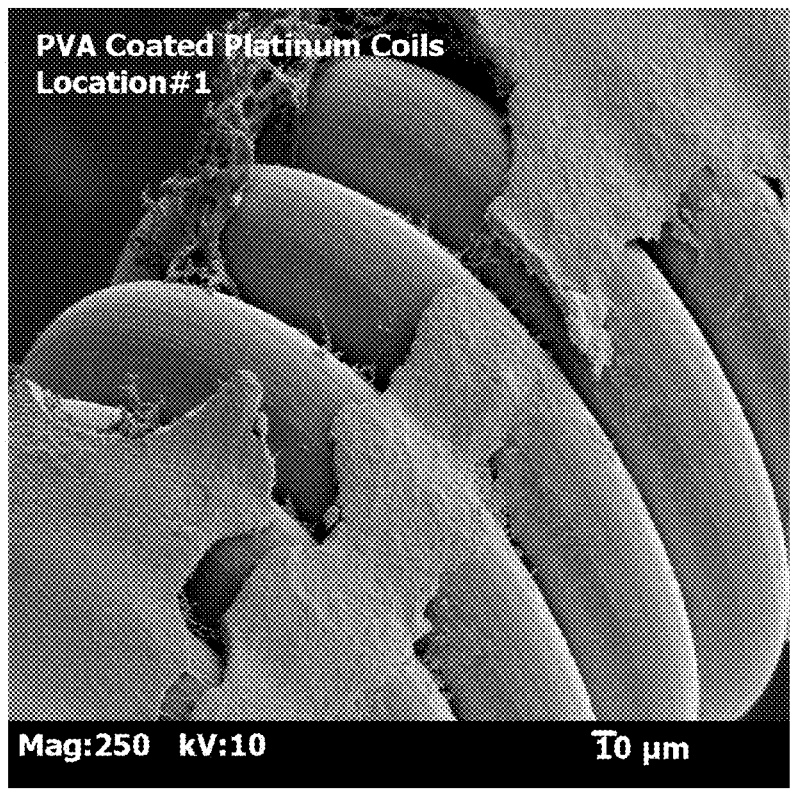
Figure 18D:
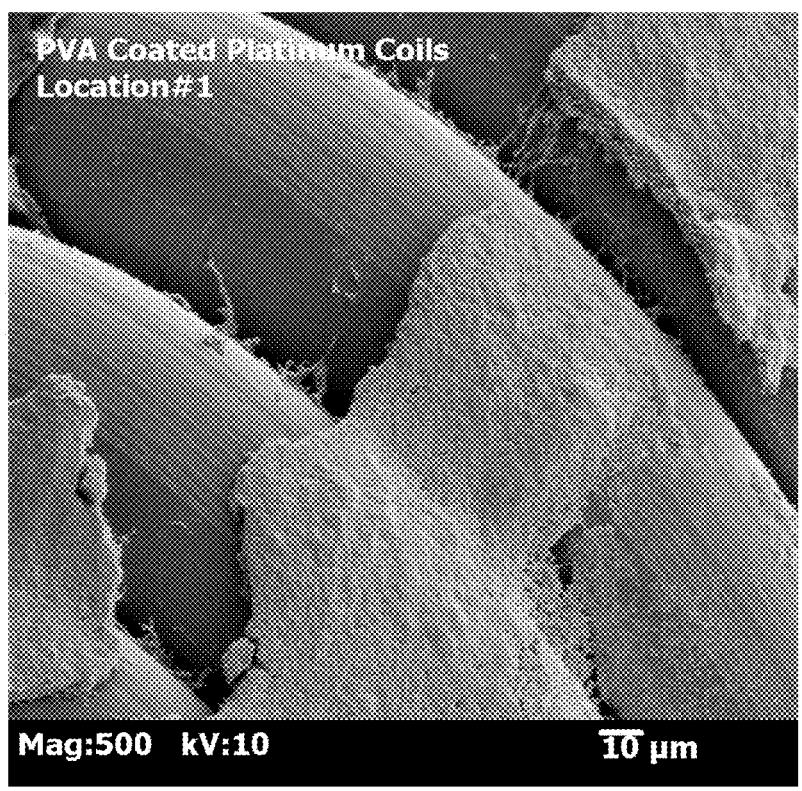
Figure 18E:
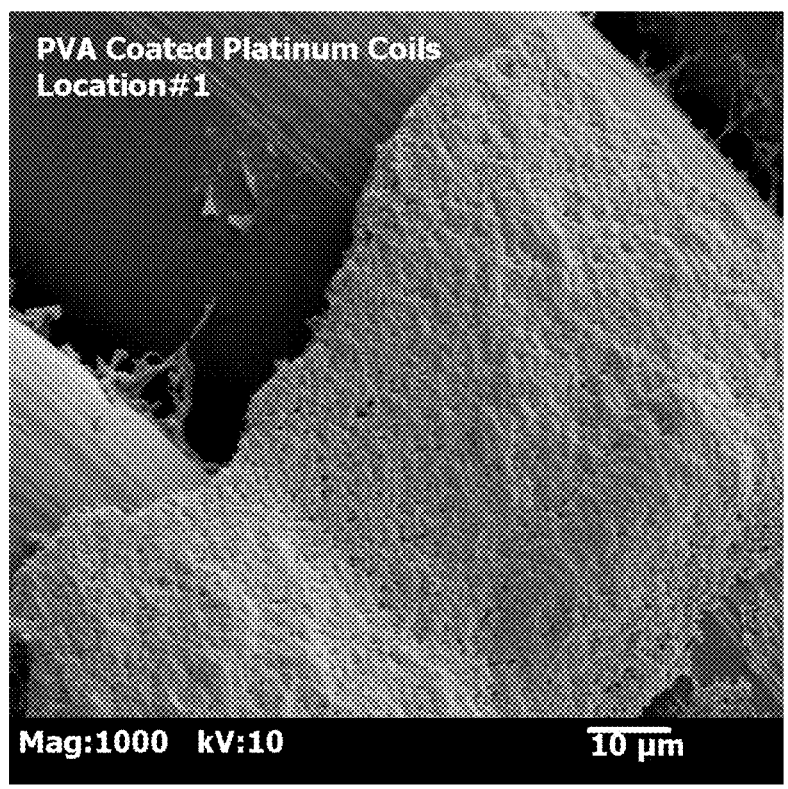
Figure 18F:
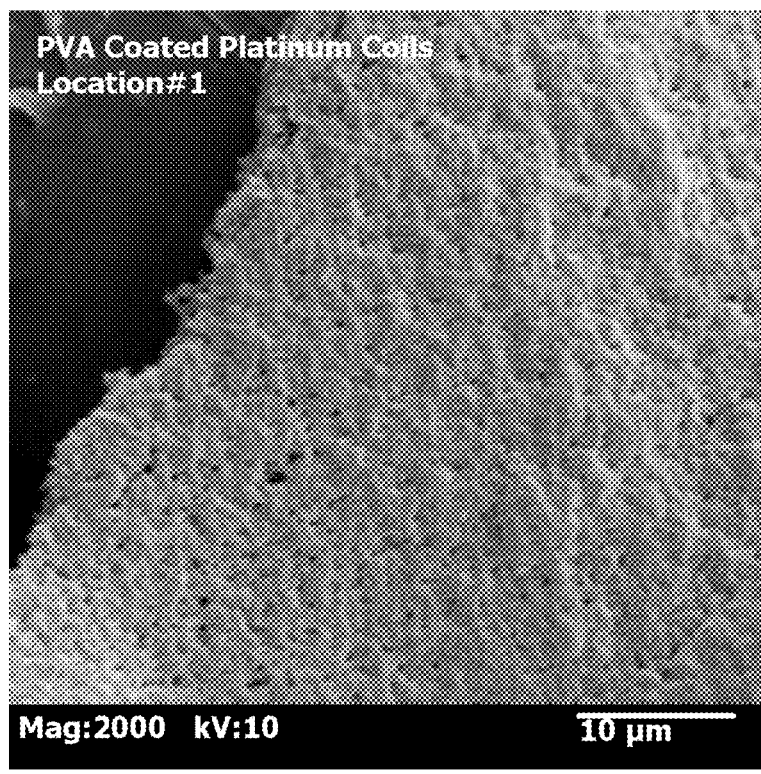

FIGS. 18A-18F are SEM images of a location ("Location #1") on one of the embolic coils of FIG. 17, at 55× magnification (FIG. 18A), 100× magnification (FIG. 18B), 250× magnification (FIG. 18C), 500× magnification (FIG. 18D), 1000× magnification (FIG. 18E), and 2000× magnification (FIG. 18F).

Figure 19A:
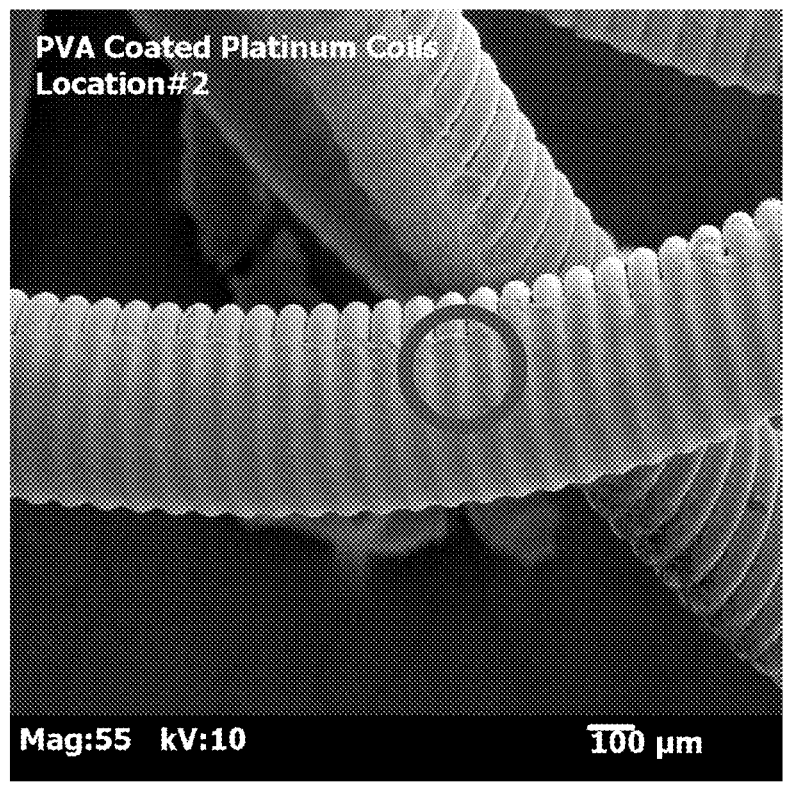
FIGS. 19A-19E are SEM images of a location on one of the embolic coils of FIG. 17, taken at different levels of magnification.
Figure 19B:
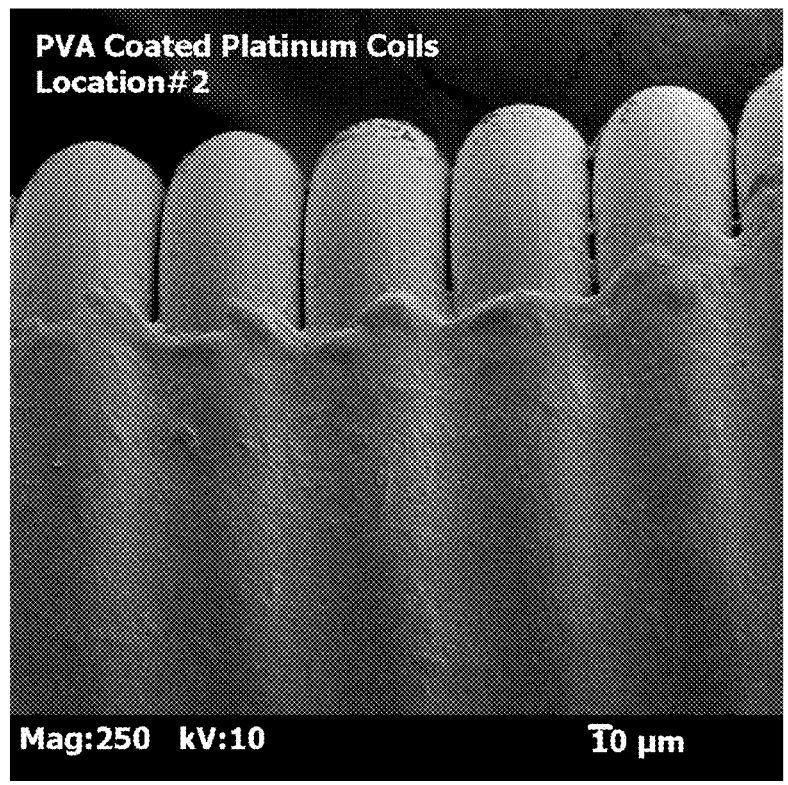
Figure 19C:
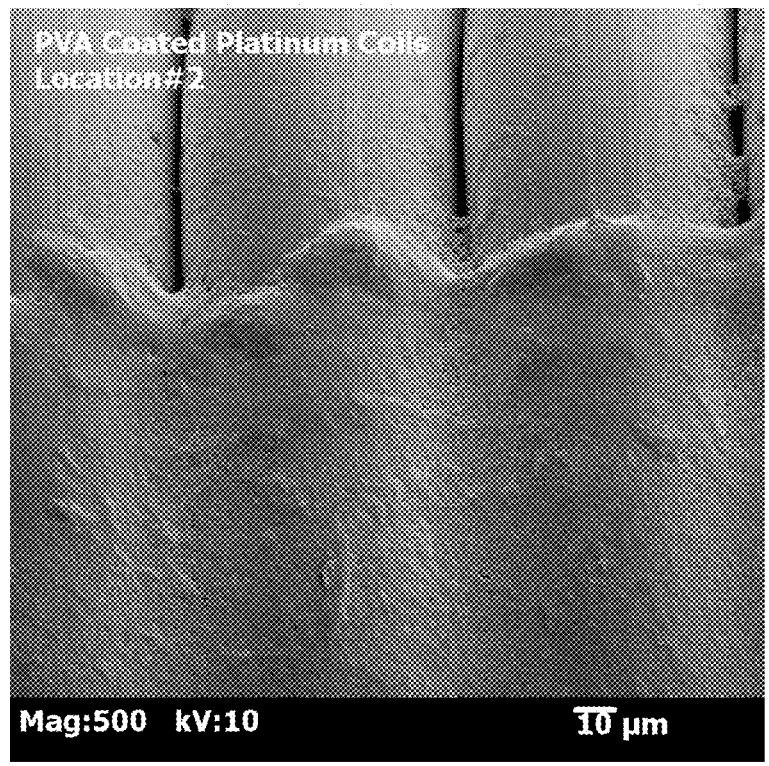
Figure 19D:
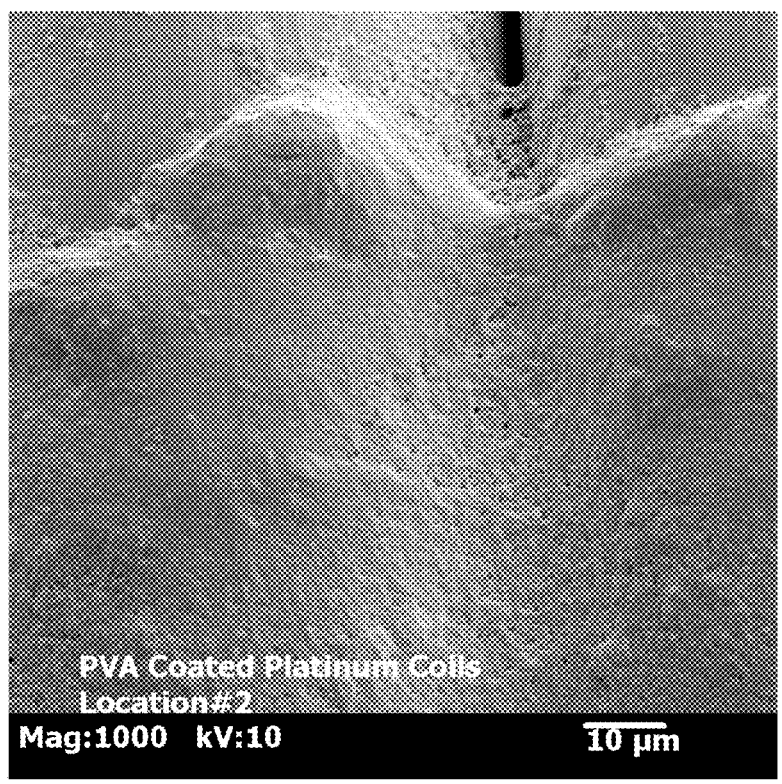
Figure 19E:
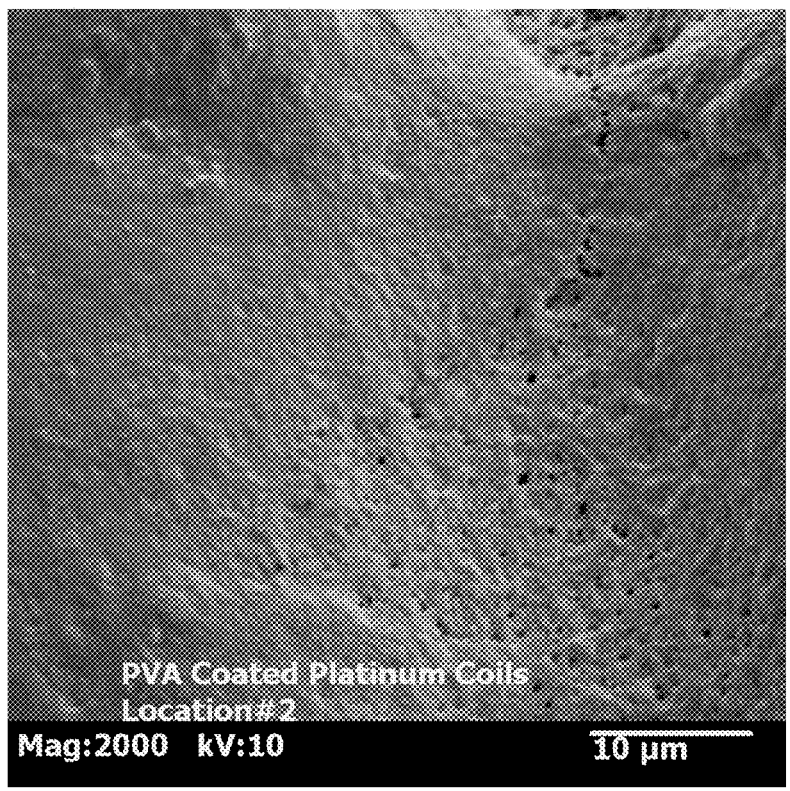

FIGS. 19A-19E are SEM images of a location ("Location #2") on one of the embolic coils of FIG. 17, at 55× magnification (FIG. 19A), 250× magnification (FIG. 19B), 500× magnification (FIG. 19C), 1000× magnification (FIG. 19D), and 2000× magnification (FIG. 19E).

Figure 20A:
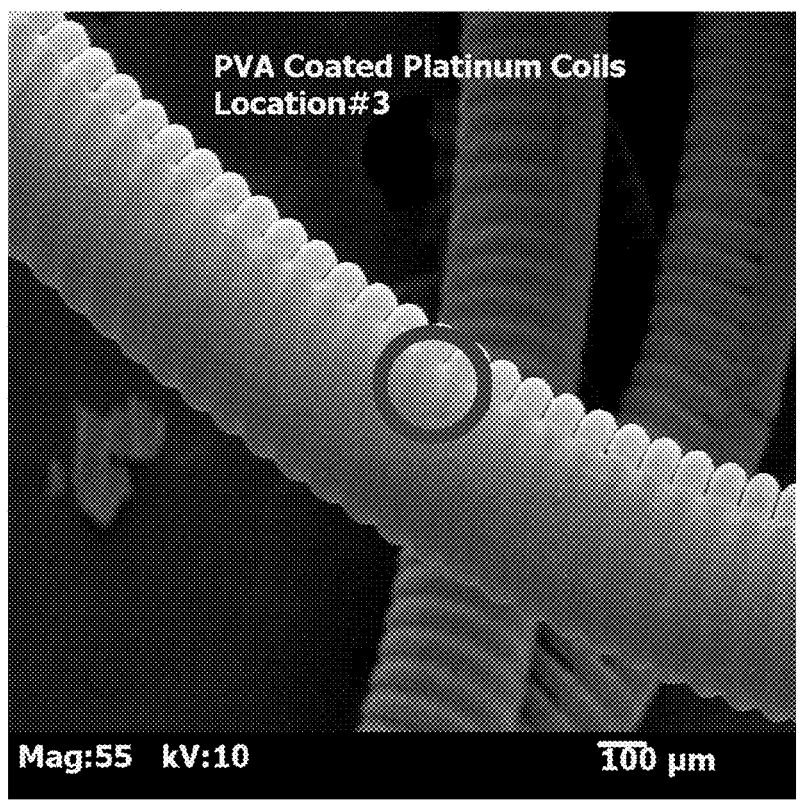
FIGS. 20A-20E are SEM images of a location on one of the embolic coils of FIG. 17, taken at different levels of magnification.
Figure 20B:
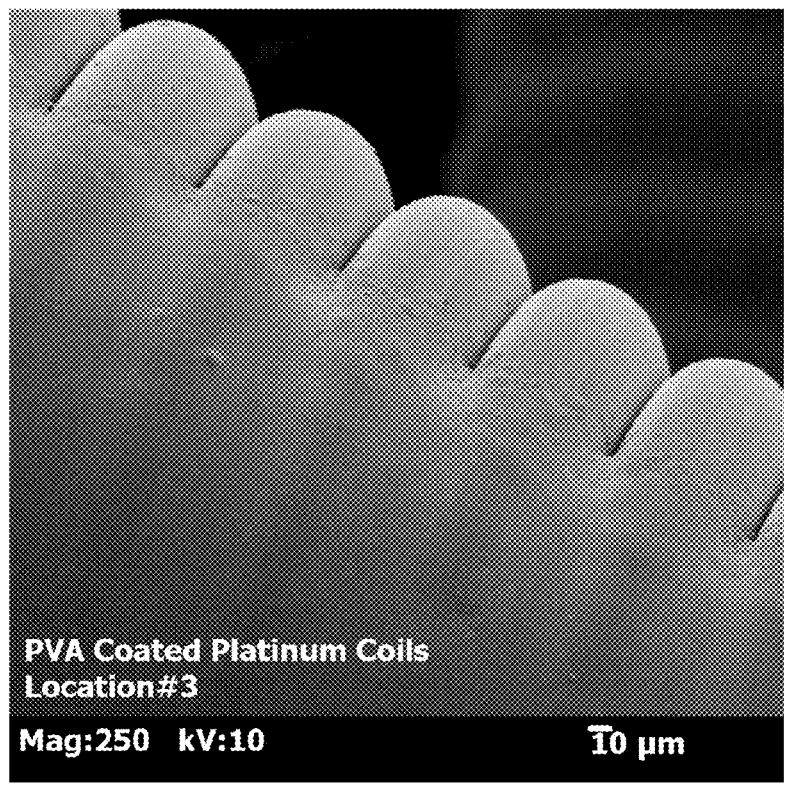
Figure 20C:
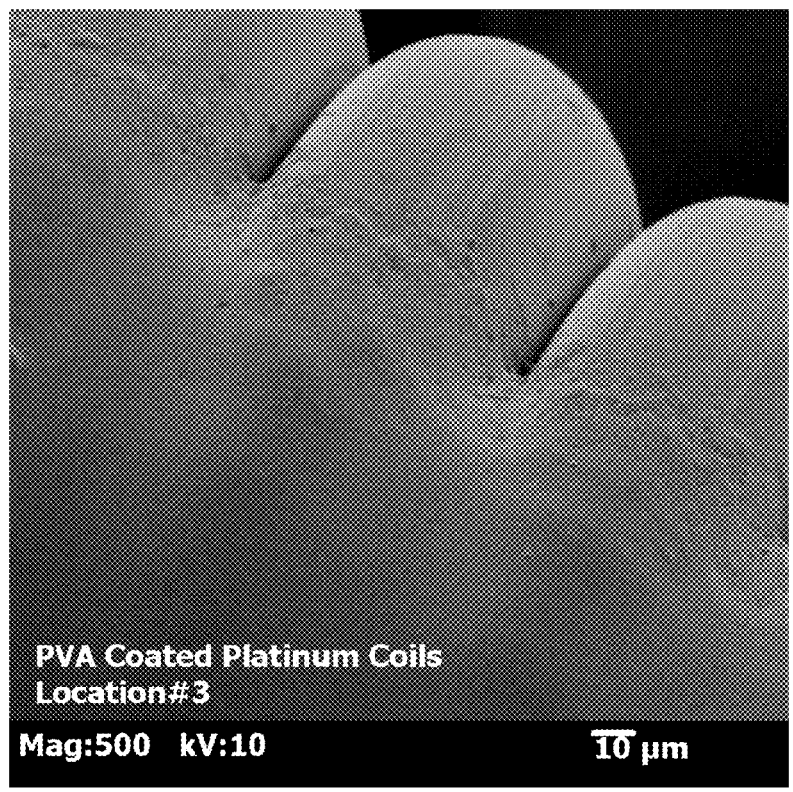
Figure 20D:
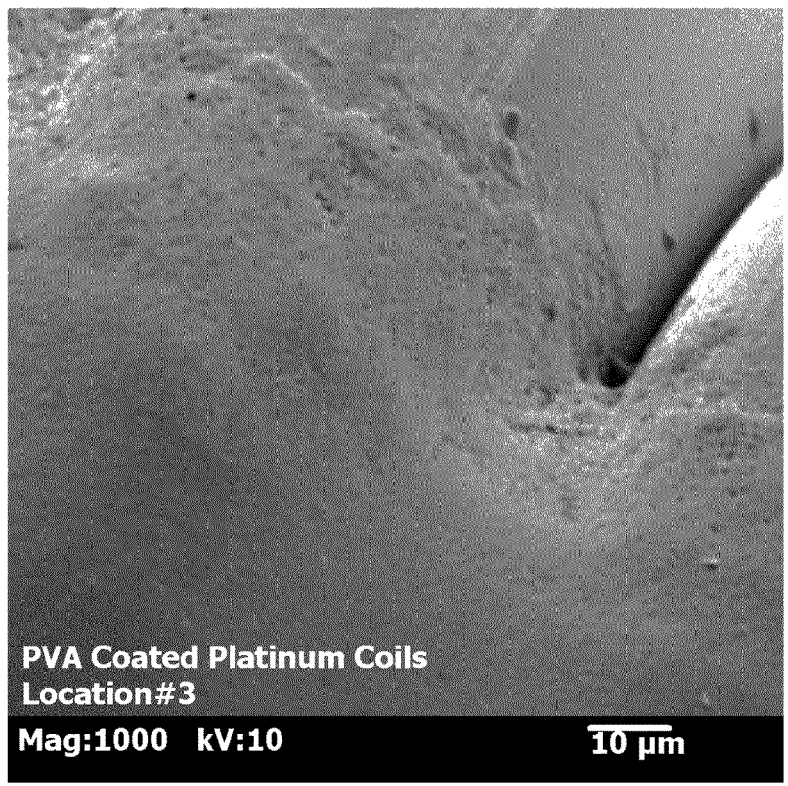
Figure 20E:
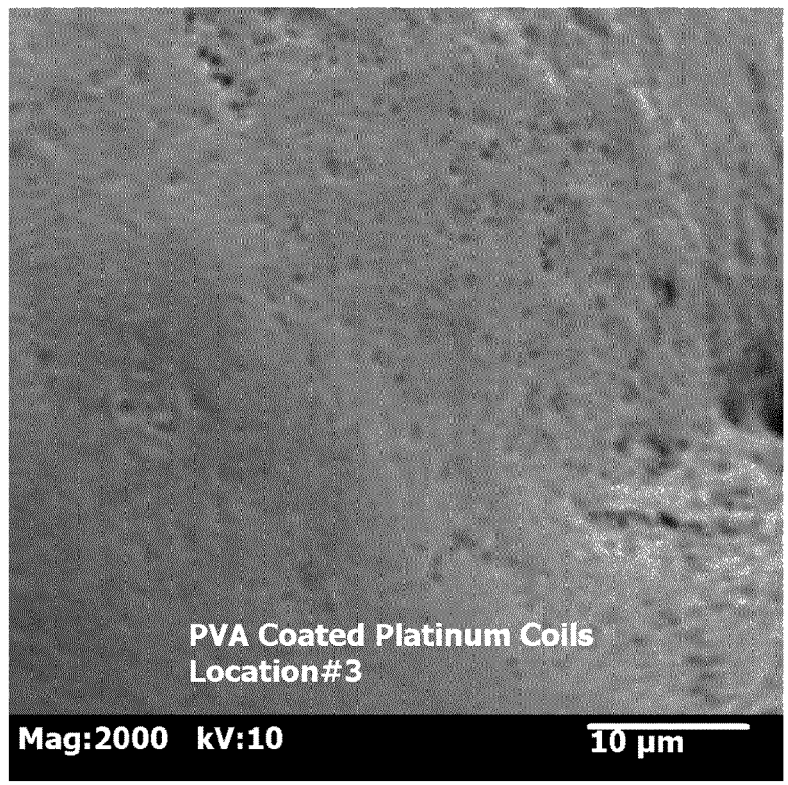

FIGS. 20A-20E are SEM images of a location ("Location #3") on one of the embolic coils of FIG. 17, at 55× magnification (FIG. 20A), 250× magnification (FIG. 20B), 500× magnification (FIG. 20C), 1000× magnification (FIG. 20D), and 2000× magnification (FIG. 20E).

Figure 21A:
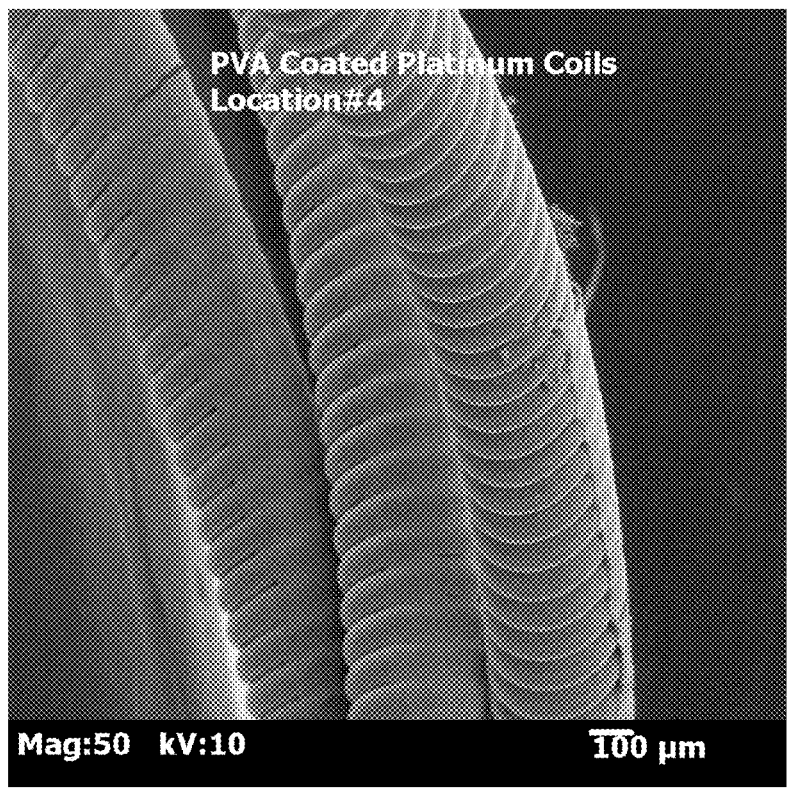
FIGS. 21A-21D are SEM images of a location on one of the embolic coils of FIG. 17, taken at different levels of magnification.
Figure 21B:
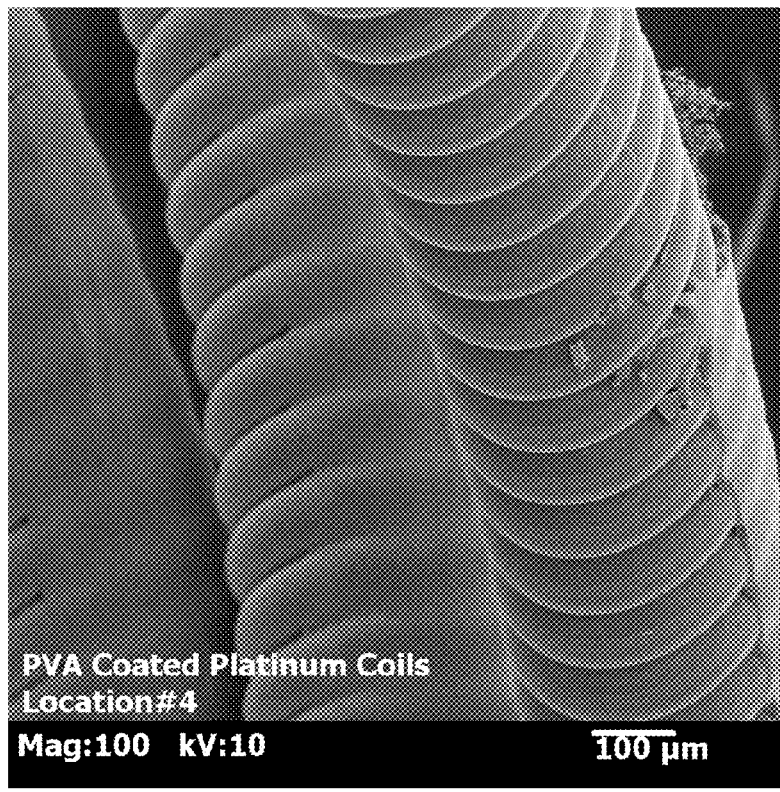
Figure 21C:
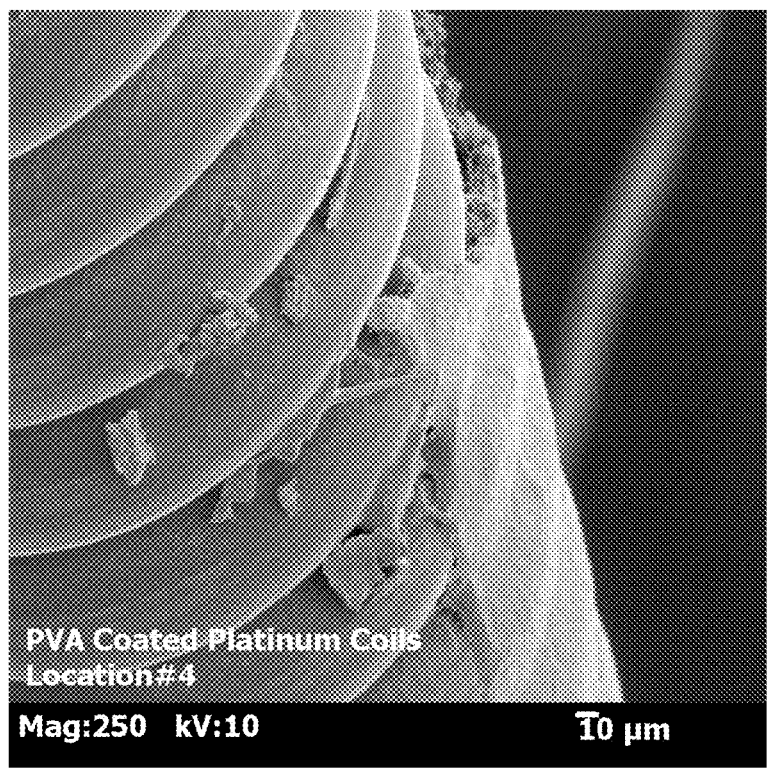
Figure 21D:
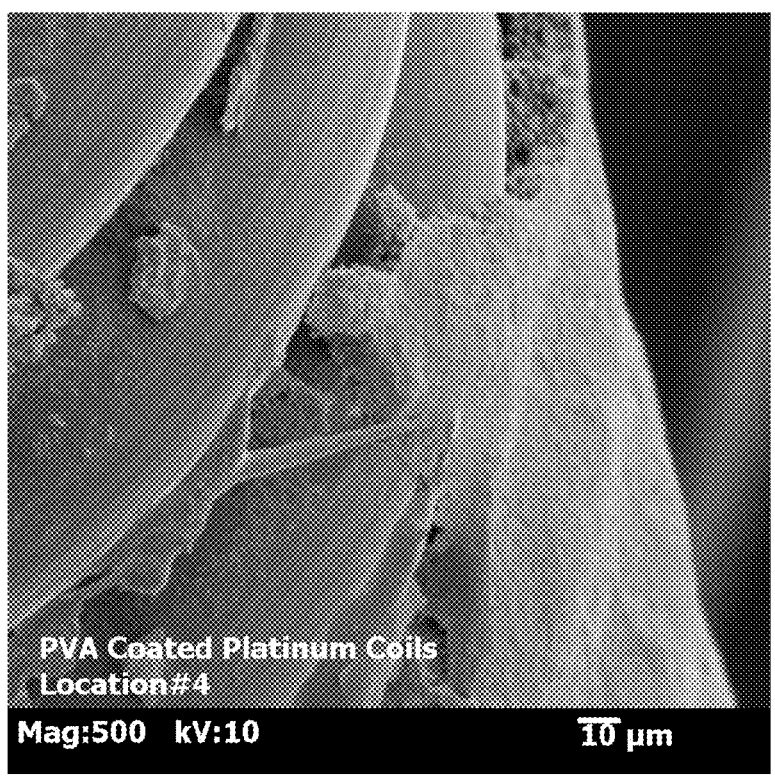

FIGS. 21A-21D are SEM images of a location ("Location #4") on one of the embolic coils of FIG. 17, at 50× magnification (FIG. 21A), 100× magnification (FIG. 21B), 250× magnification (FIG. 21C), and 500× magnification (FIG. 21D).

Example 2

One embolic coil was prepared according to the following procedure.

A bare coil (a GDC®-18 Standard coil, UPN M00335083040, from Boston Scientific Corp.) was dip-coated in a solution including two percent by weight alginate (from FMC Biopolymer, Philadelphia, Pa.), at 25° C. The coil remained in the alginate solution for 10 seconds.

The coil was then dip-coated in a solution including one percent by weight calcium chloride (from EMD Chemicals Inc. (formerly EM Industries, Inc. and EM Science), Gibbstown, N.J.), at 25° C. The coil remained in the calcium chloride solution for 10 seconds.

The resulting coated coil had an uneven coating including beads of gelled alginate.

Example 3

Five embolic coils were prepared. The following procedure was used for preparing each coil.

The coil from a VortX®-18 Diamond-Shaped Fibered Platinum Coil system (UPN M0013822030, from Boston Scientific Corp.) was removed from the introducer sheath of the system. A GDC®-18 Standard coil (UPN M00335083040, from Boston Scientific Corp.) was then inserted into the distal end of the introducer sheath, which included a luer lock on its proximal end.

A syringe containing a solution including deionized water and two percent by weight alginate (from FMC Biopolymer, Philadelphia, Pa.) was used to inject the alginate solution through the luer lock and into the introducer sheath, thereby surrounding the coil with the alginate solution.

The tip of the introducer sheath was then submerged into a bath of a solution including deionized water and one percent by weight calcium chloride (from EMD Chemicals Inc. (formerly EM Industries, Inc. and EM Science), Gibbstown, N.J.).

The syringe was then used to inject the alginate solution forcefully, thereby forcing both the coil and the alginate solution into the calcium chloride solution.

The above process was repeated to produce a total of five embolic coils.

The resulting coated coils had relatively uniform coatings, each of which had an outer diameter that was equal to the inner diameter of the introducer sheath (0.024 inch).

Other Embodiments

While certain embodiments have been described, other embodiments are possible.

Figure 22:
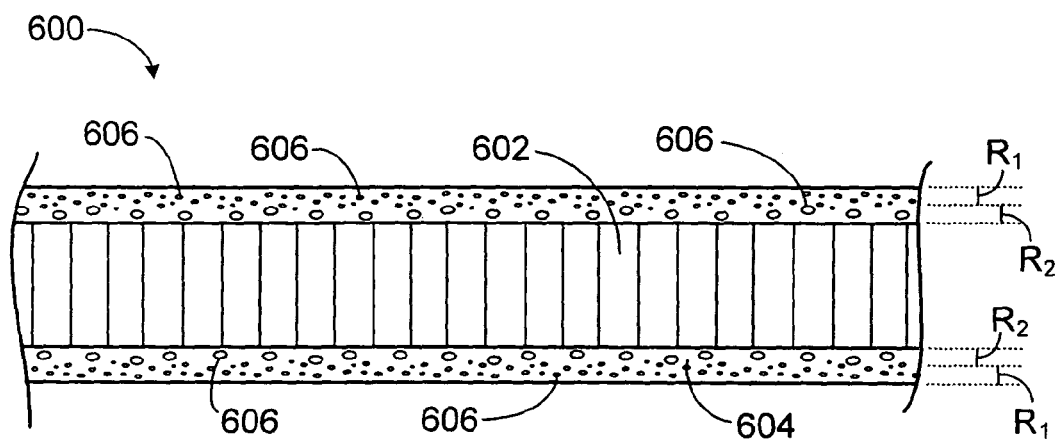
FIG. 22 is a side cross-sectional view of an embodiment of an embolic coil.

As an example, in some embodiments, an embolic coil can include a coating having a certain pore structure. For example, FIG. 22 shows an embolic coil 600 including a coil body 602 and a coating 604 including pores 606. Coating 604 includes an exterior region R1 with a thickness that is about 50 percent of the thickness of coating 604, and an interior region R2 with a thickness that is about 50 percent of the thickness of coating 604. In some embodiments, the density of pores 606 (the number of pores 606 per unit volume) in region R1 can be higher than the density of pores 606 in region R2. In certain embodiments, the average size of pores 606 in region R2 can be higher than the average size of pores 606 in region R1.

Figure 23A:
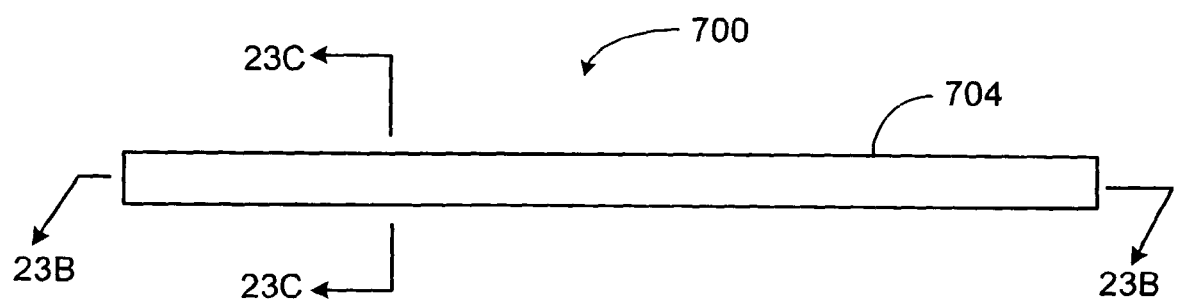
FIG. 23A is a side view of an embodiment of an embolic coil.
Figure 23B:
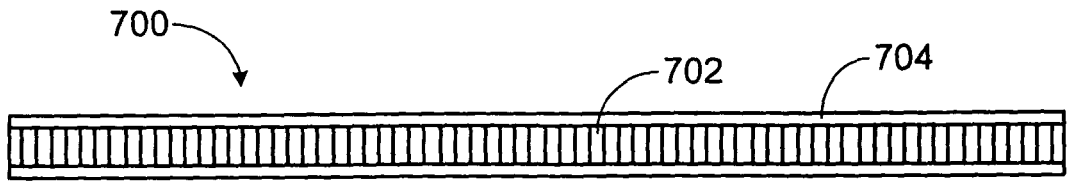
FIG. 23B is a cross-sectional view of the embolic coil of FIG. 23A, taken along line 23B-23B.
Figure 23C:
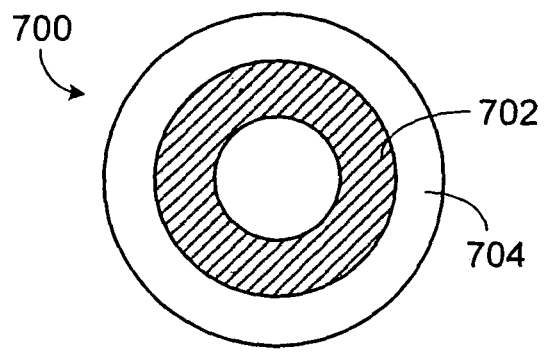
FIG. 23C is a cross-sectional view of the embolic coil of FIG. 23A, taken along line 23C-23C.

As another example, in some embodiments, an embolic coil can include a non-porous coating. For example, FIGS. 23A-23C show an embolic coil 700 including a coil body 702 and a non-porous coating 704.

Figure 24A:
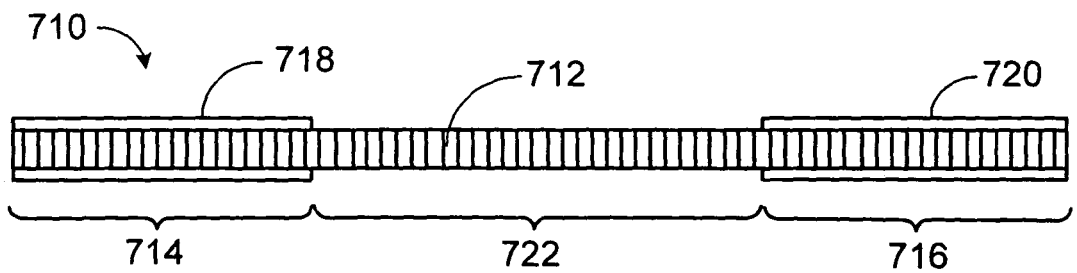
FIG. 24A is a side cross-sectional view of an embodiment of an embolic coil.
Figure 24B:
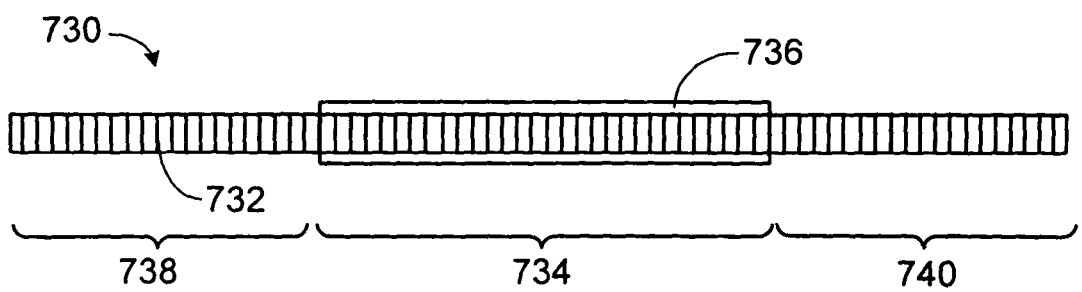
FIG. 24B is a side cross-sectional view of an embodiment of an embolic coil.

As a further example, in certain embodiments, an embolic coil can include a coil body that is coated in certain portions and that is not coated in other portions. As an example, FIG. 24A shows an embolic coil 710 including a coil body 712. Two portions 714 and 716 of embolic coil 710 include coatings 718 and 720, respectively, while a middle portion 722 of embolic coil 710 does not include any coatings. As another example, FIG. 24B shows an embolic coil 730 including a coil body 732. A middle portion 734 of embolic coil 730 includes a coating 736 while two other portions 738 and 740 of embolic coil 730 do not include any coatings.

As another example, in some embodiments, an embolic coil can include multiple (e.g., two, three, four, five, 10, 20) coatings.

As a further example, in certain embodiments, an embolic coil, coil body, and/or wire can be coated by spraying the embolic coil, coil body, and/or wire with one or more compositions (e.g., solutions). In some embodiments, an embolic coil, coil body, and/or wire can be coated by dipping the embolic coil, coil body, and/or wire into one or more compositions, such as described above in Example 2. In certain embodiments, an embolic coil, coil body, and/or wire can be coated by disposing the embolic coil, coil body, and/or wire in a container (e.g., an introducer sheath), and placing the container into a vessel containing a composition (e.g., a polymer solution, a gelling precursor solution). In some embodiments, an embolic coil, coil body, and/or wire can be coated by forming a sheath of a coating material and placing the sheath around the embolic coil, coil body, and/or wire. In certain embodiments, the sheath can be shrunk (e.g., heat-shrunk) around the embolic coil, coil body, and/or wire.

Figure 25A:
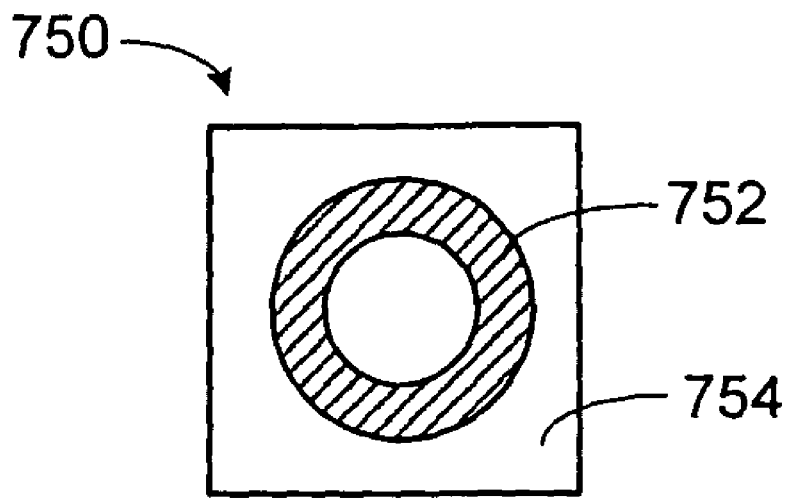
FIG. 25A is a cross-sectional view of an embodiment of an embolic coil.
Figure 25B:
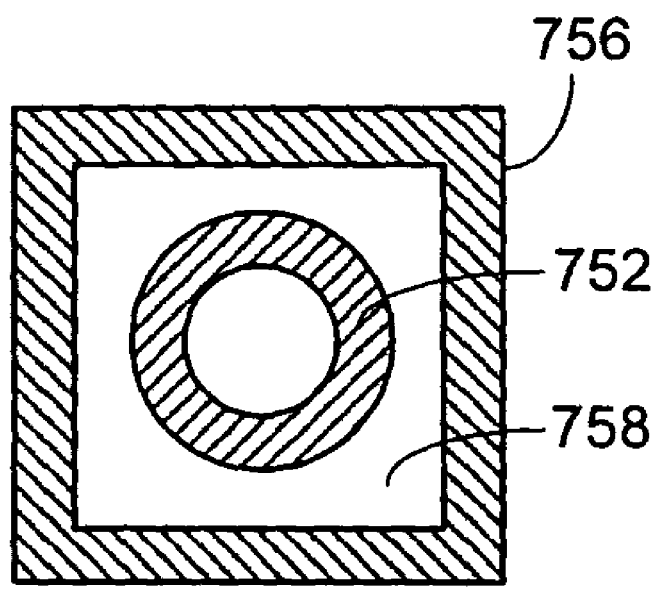
FIG. 25B is a cross-sectional view of an embodiment of a device for coating a coil body.

As an additional example, a coated embolic coil can have a circular cross-section and/or a non-circular cross-section. For example, a coated embolic coil can have a polygonal cross-section (a non-circular cross-section that is a closed plane figure bounded by straight lines). As an example, FIG. 25A shows a coated embolic coil 750 including a coil body 752 and a coating 754. Coated embolic coil 750 has a square cross-section. As shown in FIG. 25B, a coated embolic coil such as coated embolic coil 750 can be formed, for example, by coating coil body 752 while coil body 752 is disposed within a lumen 758 of a container 756 (e.g., a sheath) having a square cross-section.

As a further example, in some embodiments, an embolic coil including a coil body and a coating can be stored in saline and/or deionized water, which can hydrate the coating.

As another example, in certain embodiments, a coated coil can be dried. Examples of methods that can be used to dry a coated coil include lyophilization, freeze-drying, and allowing the coil to dry in the air. A coated coil can be dried, for example, to enhance the attachment of a delivery wire to the coil, and/or to enhance loading of the coil into a sheath and/or other delivery device (e.g., a catheter).

As an additional example, while methods of coating a coil using an introducer sheath have been described, in some embodiments, a coil can be coated while the coil is disposed within a different type of container. For example, a coil can be coated while the coil is disposed within a lumen of a catheter.

As a further example, while methods of coating a coil body by delivering certain solutions into a container (e.g., an introducer sheath) containing the coil body have been described, in some embodiments, a coil body can be coated by delivering one or more other materials into the container. As an example, in certain embodiments, a coil body can be coated by delivering a cross-linking agent into a container containing the coil body. As another example, in some embodiments, a coil body can be coated by delivering a therapeutic agent into a container containing the coil body.

As another example, in certain embodiments, a mixture (e.g., a solution, such as a solution including polyvinyl alcohol and alginate) can be contacted with a porosity-enhancing agent, such as starch, sodium chloride, or calcium chloride. Porosity-enhancing agents can increase the number and/or sizes of pores in coatings that are formed from the mixture.

As a further example, in some embodiments, an embolic coil can have at least two (e.g., three, four, five, 10, 15, 20) different outer diameters. Embolic coils with different outer diameters are described, for example, in Elliott et al., U.S. patent application Ser. No. 11/000,741, filed on Dec. 1, 2004, and entitled "Embolic Coils", which is incorporated herein by reference.

As an additional example, while embodiments have been shown in which the pitch of a coil body is substantially the same in different regions of the coil body, in certain embodiments, the pitch of a coil body can differ in different regions of the coil body. For example, some regions of a coil body can have a pitch of 0.002 inch, while other regions of an embolic coil can have a pitch of 0.004 inch.

As a further example, in some embodiments, an embolic coil can be a pushable embolic coil. The embolic coil can be delivered, for example, by pushing the embolic coil out of a delivery device (e.g., a catheter) using a pusher wire. Pushable embolic coils are described, for example, in Elliott et al., U.S. patent application Ser. No. 11/000,741, filed on Dec. 1, 2004, and entitled "Embolic Coils", which is incorporated herein by reference.

As another example, while an electrolytically detachable embolic coil has been shown, in some embodiments, an embolic coil can alternatively or additionally be a chemically detachable embolic coil and/or a mechanically detachable embolic coil. In certain embodiments, an embolic coil can be a Guglielmi Detachable Coil (GDC) or an Interlocking Detachable Coil (IDC). In some embodiments, an embolic coil can be a thermally detachable coil. As an example, in certain embodiments, an embolic coil can be attached to a pusher wire by a plastic loop. At a target site, a heating element can be used to heat the plastic loop, thereby melting the loop and releasing the coil into the target site. In some embodiments, an embolic coil can be a hydraulically detachable coil. As an example, in certain embodiments, a proximal end of an embolic coil can be attached to a holder on a pusher wire using an interference fit. Once the embolic coil is at a target site, saline can be injected into the holder under high pressure, thereby causing the embolic coil to become detached from the holder and delivered into the target site. Detachable embolic coils are described, for example, in Twyford, Jr. et al., U.S. Pat. No. 5,304,195, and Guglielmi et al., U.S. Pat. No. 5,895,385, both of which are incorporated herein by reference.

As an additional example, while detachable embolic coils have been described, in some embodiments, an embolic coil can be injectable. In certain embodiments, an injectable embolic coil can be disposed within a delivery device (e.g., a catheter) that is used to deliver the embolic coil to a target site. Once at the target site, the injectable embolic coil can be delivered into the target site using a high-pressure saline flush that pushes the embolic coil out the of the delivery device. In some embodiments, a pusher wire can be used in conjunction with a saline flush to deliver an embolic coil to a target site. In certain embodiments, a pusher wire may not be used in conjunction with a saline flush to deliver an embolic coil to a target site.

As a further example, in certain embodiments, a coil can be at least partially delivered from a delivery device, and then can be retracted back into the delivery device.

Figure 26:
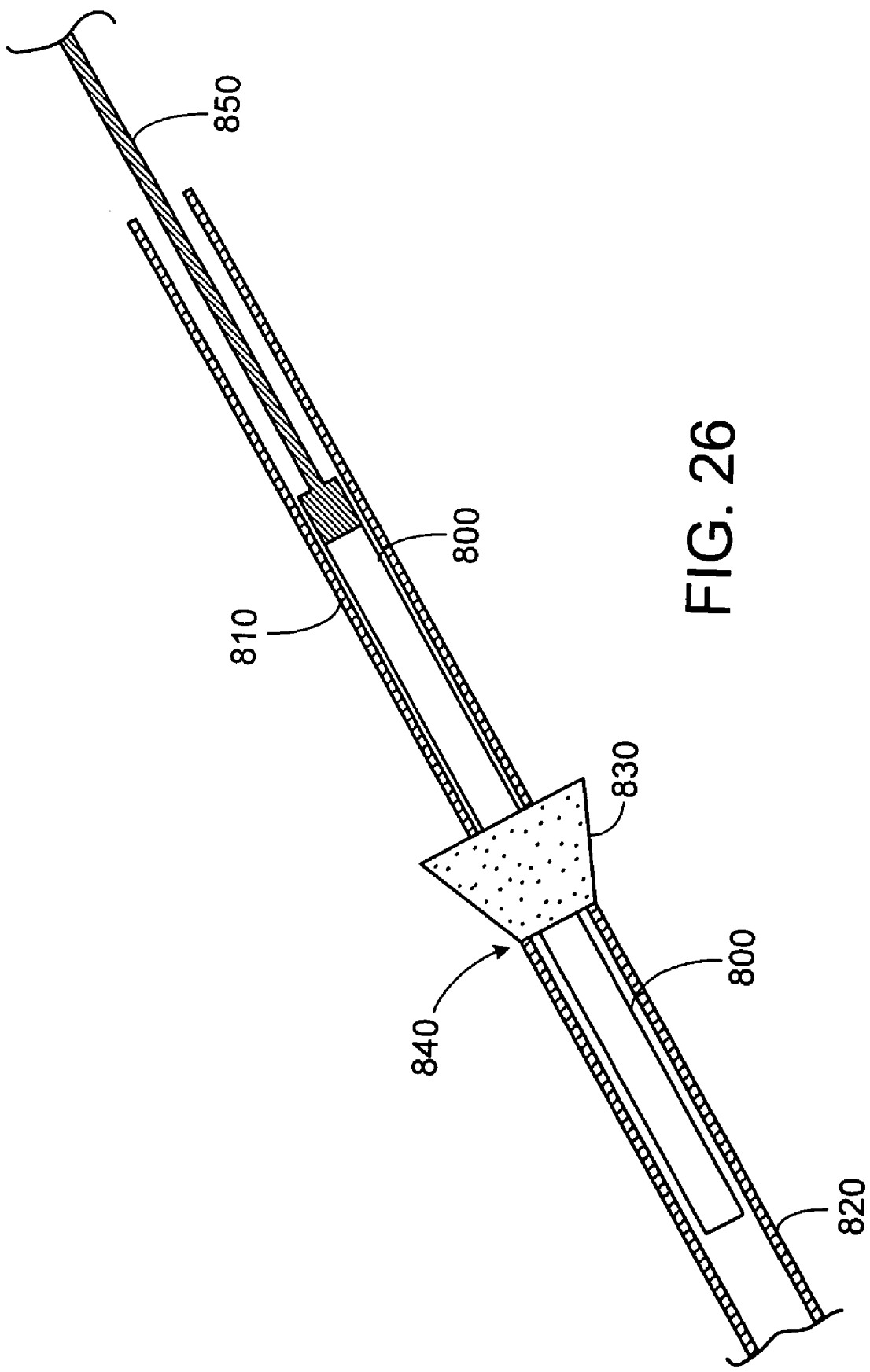
FIG. 26 illustrates the delivery of an embodiment of an embolic coil from an introducer sheath into a delivery device.

As another example, in certain embodiments, an embolic coil can be loaded into a delivery device using an introducer sheath. For example, FIG. 26 illustrates the transfer of a coated embolic coil 800 from an introducer sheath 810 into a catheter 820. A hub 830 located at the proximal end 840 of catheter 820 directs the placement of introducer sheath 810. After introducer sheath 810 has been placed in hub 830, a pusher 850 is used to push embolic coil 800 out of introducer sheath 810 and into catheter 820.

As an additional example, in some embodiments, multiple (e.g., two, three, four) embolic coils can be delivered using one delivery device.

As a further example, in certain embodiments, a treatment site can be occluded by using embolic coils in conjunction with other occlusive devices. For example, embolic coils can be used with embolic particles, such as those described in Buiser et al., U.S. Patent Application Publication No. U.S. 2003/0185896 A1, published on Oct. 2, 2003, and in Lanphere et al., U.S. Patent Application Publication No. U.S. 2004/0096662 A1, published on May 20, 2004, both of which are incorporated herein by reference. In some embodiments, embolic coils can be used in conjunction with one or more embolic gels. Embolic gels are described, for example, in Richard et al., U.S. patent application Ser. No. 10/927,868, filed on Aug. 27, 2004, and entitled "Embolization", which is incorporated herein by reference.

As an additional example, in some embodiments, an embolic coil can include one or more radiopaque markers. The radiopaque markers can, for example, be attached to one or more windings of the embolic coil.

Figure 27A:
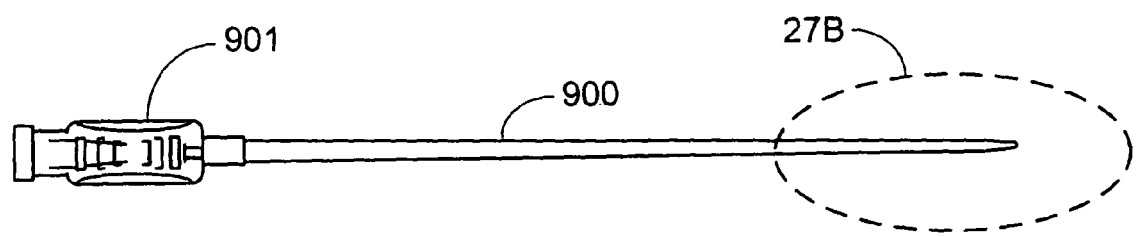
FIG. 27A is an illustration of an embodiment of an introducer sheath.
Figure 27B:
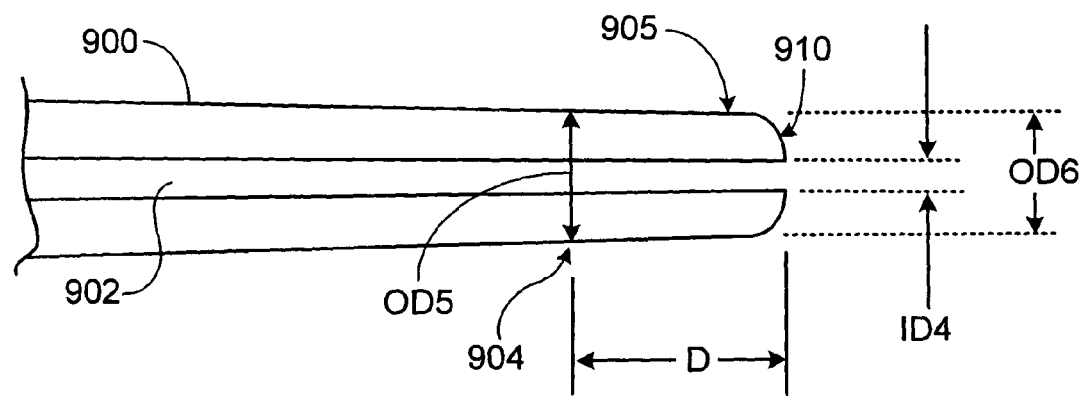
FIG. 27B is an enlarged view of region 27B of FIG. 27A.

As a further example, in certain embodiments, a tapered introducer sheath can be used to form a coated coil, and/or to deliver a coil (e.g., a coated coil). For example, FIGS. 27A and 27B show a tapered introducer sheath 900 with a lumen 902. Introducer sheath 900 is attached to a hub 901. As shown in FIG. 27B, introducer sheath 900 has an inner diameter ID4, an outer diameter OD5 in one region 904 of introducer sheath 900, and an outer diameter OD6 in another region 905 of introducer sheath 900. Region 904 is located at a distance D from the distal end 910 of introducer sheath 900. In certain embodiments, distance D can be about 0.1 inch. In some embodiments, inner diameter ID4 can be at least 0.008 inch and/or at most 0.038 inch (e.g., 0.023 inch). In certain embodiments, outer diameter OD5 can be at least 0.01 inch and/or at most 0.06 inch (e.g., 0.0385 inch). In some embodiments, outer diameter OD6 can be at least 0.01 inch and/or at most 0.059 inch (e.g., 0.0335 inch). An introducer sheath can include a tapered inner diameter, a tapered outer diameter, or both a tapered inner diameter and a tapered outer diameter.

As another example, in some embodiments, an embolic coil coating can have a relatively smooth surface. An embolic coil coating with a relatively smooth surface can be formed, for example, by placing an embolic coil into the lumen of an introducer sheath having a relatively smooth interior surface, and coating the embolic coil while the embolic coil is in the introducer sheath.

As an additional example, in some embodiments, an embolic coil coating can have a relatively rough surface. In certain embodiments, as the roughness of the surface of an embolic coil coating increases, the embolic coil coating can become more thrombogenic. In some embodiments, an embolic coil coating with a relatively rough surface can be formed by placing an embolic coil into the lumen of an introducer sheath having a relatively rough interior surface, and coating the embolic coil while the embolic coil is in the introducer sheath. The interior surface of an introducer sheath can be roughened using, for example, a file to file material away from the interior surface, and/or a microblasting method. In certain embodiments, the surface of an embolic coating can be roughened after the coating has been formed. For example, a microblasting method and/or a filing method can be used to roughen the surface of the coating.

Other embodiments are in the claims.

What is claimed is:

1. A method of coating a coil, the method comprising:
    injecting a material comprising a first polymer and a gelling precursor into a container containing the coil;
    gelling the gelling precursor to provide a first coating on the coil, the coating comprising the first polymer and the gelled precursor;
    cross-linking the first polymer in the first coating to provide a second coating on the coil, the second coating comprising the cross-linked first polymer and the gelled precursor; and
    removing the gelled precursor from the second coating to provide a third coating on the coil, the third coating comprising the cross-linked first polymer having pores therein.

2. The method of claim 1, wherein the coil is an embolic coil.

3. The method of claim 1, wherein the first polymer comprises a polysaccharide.

4. The method of claim 1, wherein the first polymer comprises alginate.

5. The method of claim 1, wherein the first polymer comprises polyvinyl alcohol.

6. The method of claim 1, wherein the material further comprises a second polymer different from the first polymer.

7. The method of claim 1, wherein gelling the gelling precursor comprises contacting the material with a gelling agent.

8. The method of claim 7, wherein contacting the material with the gelling agent comprises delivering the gelling agent into the container.

9. The method of claim 1, wherein cross-linking the first polymer comprises contacting the material with a cross-linking agent.

10. The method of claim 1, further comprising contacting the third coating with a therapeutic agent.

11. The method of claim 1, wherein the material comprises a therapeutic agent.

12. The method of claim 1, wherein the container comprises a tubular member.

13. The method of claim 1, further comprising removing the coil from the container.

14. The method of claim 13, wherein the container comprises a bioerodible or bioabsorbable material, and removing the coil from the container comprises eroding or absorbing the container.

* * * * *